(12) United States Patent
Hasegawa et al.

(10) Patent No.: US 7,833,694 B2
(45) Date of Patent: Nov. 16, 2010

(54) LACTONE-CONTAINING COMPOUND, POLYMER, RESIST COMPOSITION, AND PATTERNING PROCESS

(75) Inventors: Koji Hasegawa, Joetsu (JP); Satoshi Shinachi, Joetsu (JP); Katsuhiro Kobayashi, Joetsu (JP); Tsunehiro Nishi, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/403,317

(22) Filed: Mar. 12, 2009

(65) Prior Publication Data

US 2009/0233242 A1 Sep. 17, 2009

(30) Foreign Application Priority Data

Mar. 13, 2008 (JP) .............................. 2008-064337

(51) Int. Cl.
G03F 7/004 (2006.01)
G03F 7/30 (2006.01)
C08F 28/06 (2006.01)
C07D 407/04 (2006.01)
C07C 69/74 (2006.01)

(52) U.S. Cl. .................. 430/270.1; 430/273.1; 430/296; 430/326; 430/330; 430/907; 430/910; 526/256; 526/257; 526/282; 549/45; 549/300; 560/220

(58) Field of Classification Search ............... 430/270.1, 430/273.1, 296, 326, 330, 907, 910; 526/256, 526/257, 282; 549/45, 300; 560/220
See application file for complete search history.

(56) References Cited

U.S. PATENT DOCUMENTS

| | | | |
|---|---|---|---|
| 6,280,898 B1 | 8/2001 | Hasegawa et al. |
| 6,312,867 B1 | 11/2001 | Kinsho et al. |
| 6,329,125 B2 | 12/2001 | Takechi et al. |
| 6,448,420 B1 | 9/2002 | Kinsho et al. |
| 6,830,866 B2 | 12/2004 | Kobayashi et al. |
| 2005/0048402 A1 | 3/2005 | Mizutani et al. |
| 2005/0227174 A1 | 10/2005 | Hatakeyama et al. |
| 2005/0260525 A1 | 11/2005 | Takemoto et al. |
| 2007/0128555 A1 | 6/2007 | Harada et al. |
| 2007/0160929 A1 | 7/2007 | Hasegawa et al. |
| 2007/0218401 A1 | 9/2007 | Ando et al. |
| 2008/0026331 A1 | 1/2008 | Hasegawa et al. |
| 2008/0090173 A1 | 4/2008 | Harada et al. |
| 2009/0023878 A1 | 1/2009 | Maeda et al. |

FOREIGN PATENT DOCUMENTS

| | | |
|---|---|---|
| JP | 4-39665 A | 2/1992 |
| JP | 9-90637 A | 4/1997 |
| JP | 2000-26446 A | 1/2000 |
| JP | 2000-159758 A | 6/2000 |
| JP | 2000-327633 A | 11/2000 |
| JP | 2000-336121 A | 12/2000 |
| JP | 2001-188346 A | 7/2001 |
| JP | 2002-169289 A | 6/2002 |
| JP | 2003-66612 A | 3/2003 |
| JP | 2005-321785 A | 11/2005 |
| JP | 2005-352466 A | 12/2005 |
| JP | 2006-1102 A | 1/2006 |
| JP | 2007-153982 A | 6/2007 |
| JP | 2007-249192 A | 9/2007 |
| JP | 2008-31298 A | 2/2008 |
| JP | 2008-43501 A | 2/2008 |
| JP | 200888343 A | 4/2008 |
| WO | 2009/107327 A1 | 9/2009 |

OTHER PUBLICATIONS

Koji Arimitsu et al., "Sensitivity Enhancement of Chemical-Amplification-Type Photoimaging Materials by Acetoacetic Acid Derivatives", Journal of Photopolymer Science and Technology, vol. 8, No. 1, pp. 43-44 (1995).

(Continued)

Primary Examiner—John S Chu
(74) Attorney, Agent, or Firm—Birch, Stewart, Kolasch & Birch, LLP

(57) ABSTRACT

Lactone-containing compounds having formula (1) are novel wherein $R^1$ is H, F, methyl or trifluoromethyl, $R^2$ and $R^3$ are H or monovalent hydrocarbon groups, or $R^2$ and $R^3$ may together form an aliphatic hydrocarbon ring, $R^4$ is H or $CO_2R^5$, $R^5$ is a monovalent hydrocarbon group, W is $CH_2$, O or S, and $k^1$ is 3, 4 or 5. They are useful as monomers to produce polymers which are transparent to radiation ≦500 nm. Radiation-sensitive resist compositions comprising the polymers as base resin exhibit excellent properties including resolution, LER, pattern density dependency and exposure margin.

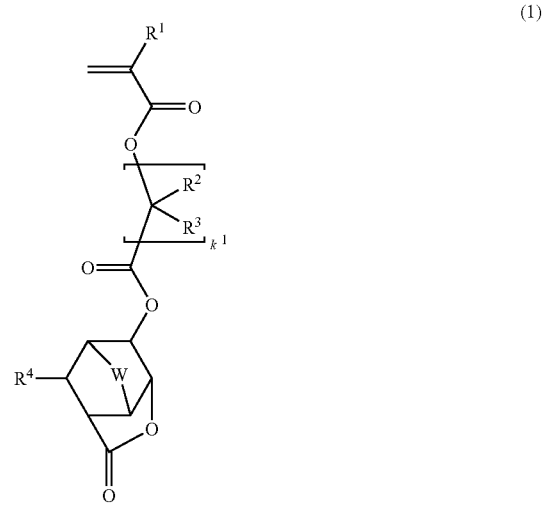

8 Claims, No Drawings

OTHER PUBLICATIONS

Kazuaki Kudo et al., "Enhancement of the Senesitivity of Chemical-Amplification-Type Photoimaging Materials by β-Tosyloxyketone Acetals", Journal of Photopolymer Science and Technology, vol. 8, No. 1, pp. 45-46 (1995).

Koji Arimitsu et al., "Effect of Phenolic Hydroxyl Residues on the Improvement of Acid-Proliferation-Type Photoimaging Materials", Journal of Photopolymer Science and Technology, vol. 9, No. 1, pp. 29-30, (1996).

M. Maenhoudt et al., Double Patterning scheme for sub-0.25 k1 single damascene structures at NA=0.75, λ=193nm, Proceedings of SPIE, vol. 5754, pp. 1508, (2005).

Masato Shibuya et al., "Performance of Resolution Enhancement Technique Using Both Multiple Exposure and Nonlinear Resist", Jpn. J. Phys. vol. 33, 6874-6877, (1994).

Search Report mailed Jun. 8, 2009 in connection with corresponding European Application No. 09003396.0.

LACTONE-CONTAINING COMPOUND, POLYMER, RESIST COMPOSITION, AND PATTERNING PROCESS

CROSS-REFERENCE TO THE RELATED APPLICATION

This non-provisional application claims priority under 35 U.S.C. §119(a) on Patent Application No. 2008-064337 filed in Japan on Mar. 13, 2008, the entire contents of which are hereby incorporated by reference.

This application is related to the co-pending and commonly-assigned U.S. patent application Ser. No. 11/878,759 (US 20080026331 A1, JP-A 2008-031298, inventors: Hasegawa, Nishi, Kinsho, and Tachibana).

TECHNICAL FIELD

This invention relates to (1) novel lactone-containing compounds useful as raw materials for the synthesis of functional materials, pharmaceutical and agricultural chemicals, (2) polymers comprising recurring units derived from the lactone-containing compounds, (3) resist compositions comprising the polymers, and (4) a patterning process using the resist compositions.

BACKGROUND ART

The recent drive for higher integration and operating speeds in LSI devices makes it necessary to further reduce the pattern rule. Deep-ultraviolet lithography was developed as an essential technology for micropatterning to a feature size of 0.3 µm or less. Among others, the KrF excimer laser lithography has been fully recognized as a commercial scale production technology.

With respect to chemically amplified resist compositions adapted for the photolithography using ArF excimer laser light of 193 nm wavelength as a light source, the primary requirement is, of course, a high transparency at that wavelength. They are also required to meet a high etch resistance sufficient to comply with film thickness reduction, a high sensitivity sufficient to minimize the burden to expensive optical materials, and among others, a high resolution sufficient to form an exact fine pattern. The key toward these requirements is to develop a base resin featuring high transparency, high rigidity and high reactivity. Active efforts have been devoted for such development.

Typical resins known to be highly transparent to ArF excimer laser light are copolymers of acrylic or methacrylic acid derivatives as disclosed in JP-A 4-39665.

One of the (meth)acrylic resins proposed thus far is a combination of (meth)acrylic units having methyladamantane ester as acid labile group units with (meth)acrylic units having lactone ring ester as adhesive group units as disclosed in JP-A 9-90637. Acid labile groups of exo form are described in U.S. Pat. No. 6,448,420 (JP-A 2000-327633). These groups have so high an acid elimination ability and require a low level of activation energy for acid elimination, affording a high resolution and low dependence on post-exposure bake (PEB). Norbornane lactone is also proposed as an adhesive group having enhanced etching resistance as disclosed in JP-A 2000-26446 and JP-A 2000-159758. These studies have achieved significant improvements in the resolution of ArF resists.

However, in an attempt to form a fine pattern having a pitch of less than 200 nm, prior art resist materials are difficult to form patterns and the patterns, if formed, have insufficient rectangularity and substantial roughness on their surface and sidewalls, and are hardly believed to clear the practically acceptable level. Of the problems associated with prior art resist materials, the most serious problem is the unevenness of fine line size, which is generally referred to as "line edge roughness" (LER). Since the LER has a substantial impact on the performance of semiconductor devices being fabricated, it is strongly desired to overcome this problem. If it is merely required to form a pattern in a smooth finish, that purpose may be attained to a more or less extent by selecting a resin with a lower molecular weight and/or a photoacid generator which generates a more mobile acid. With this approach, however, not only properties such as exposure dose dependency, pattern density dependency, and mask fidelity are extremely exacerbated, but also the line size itself rather becomes uneven because minute fluctuations at the mask are enlarged. This approach does not lead to a reduction of LER. Under the continuing demand for a further reduction of the pattern rule, the resist is required to provide good performance with respect to sensitivity, substrate adhesion and etch resistance and additionally, to find an essential solution to improve LER without sacrifice of resolution.

Citation List
Patent Document 1: JP-A H4-39665
Patent Document 2: JP-A H9-90637
Patent Document 3: U.S. Pat. No. 6,448,420 (JP-A 2000-327633)
Patent Document 4: JP-A 2000-26446
Patent Document 5: JP-A 2000-159758

SUMMARY OF THE INVENTION

An object of the present invention is to provide lactone-containing compounds useful as monomers for the synthesis of polymers, polymers comprising recurring units derived from the lactone-containing compounds, and resist compositions comprising the polymers, the resist compositions exhibiting a high resolution and minimized pattern edge roughness when processed by photolithography using high-energy radiation such as ArF excimer laser radiation as a light source. Another object is to provide a patterning process using the resist compositions.

The inventors have found that a lactone-containing compound of the general formula (1) shown below can be readily prepared in high yields, and that a resist composition comprising a polymer derived from the lactone-containing compound as a base resin exhibits satisfactory properties including exposure dose dependency, pattern density dependency, and mask fidelity as well as minimized pattern edge roughness when processed by photolithography, so that the polymer is advantageously used in resist form for precise micropatterning.

Accordingly, the present invention provides a lactone-containing compound, polymer, resist composition, and patterning process, as defined below.

[1] A lactone-containing compound having the general formula (1).

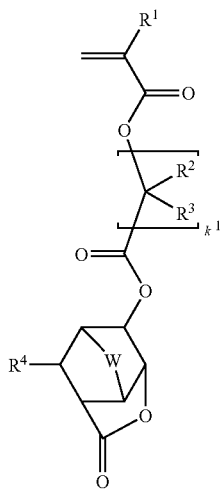

Herein $R^1$ is hydrogen, fluorine, methyl or trifluoromethyl, $R^2$ and $R^3$ are each independently hydrogen or a straight, branched or cyclic monovalent hydrocarbon group of 1 to 10 carbon atoms, or $R^2$ and $R^3$ may bond together to form an aliphatic hydrocarbon ring with the carbon atom to which they are attached, $R^4$ is hydrogen or $CO_2R^5$, $R^5$ is a straight, branched or cyclic monovalent hydrocarbon group of 1 to 15 carbon atoms which may have a halogen or oxygen atom, W is $CH_2$, O or S, with the proviso that $R^4$ is $CO_2R^5$ when W is $CH_2$, and $R^4$ is hydrogen or $CO_2R^5$ when W is O or S, and $k^1$ is an integer of 3 to 5.

[2] A polymer comprising recurring units derived from the lactone-containing compound of [1].

[3] A polymer comprising recurring units having the general formula (2).

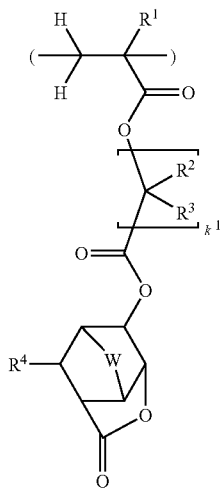

Herein $R^1$ is hydrogen, fluorine, methyl or trifluoromethyl, $R^2$ and $R^3$ are each independently hydrogen or a straight, branched or cyclic monovalent hydrocarbon group of 1 to 10 carbon atoms, or $R^2$ and $R^3$ may bond together to form an aliphatic hydrocarbon ring with the carbon atom to which they are attached, $R^4$ is hydrogen or $CO_2R^5$, $R^5$ is a straight, branched or cyclic monovalent hydrocarbon group of 1 to 15 carbon atoms which may have a halogen or oxygen atom, W is $CH_2$, O or S, with the proviso that $R^4$ is $CO_2R^5$ when W is $CH_2$, and $R^4$ is hydrogen or $CO_2R^5$ when W is O or S, and $k^1$ is an integer of 3 to 5.

[4] The polymer of [2] or [3], further comprising recurring units having at least one of the general formulas (3) to (6).

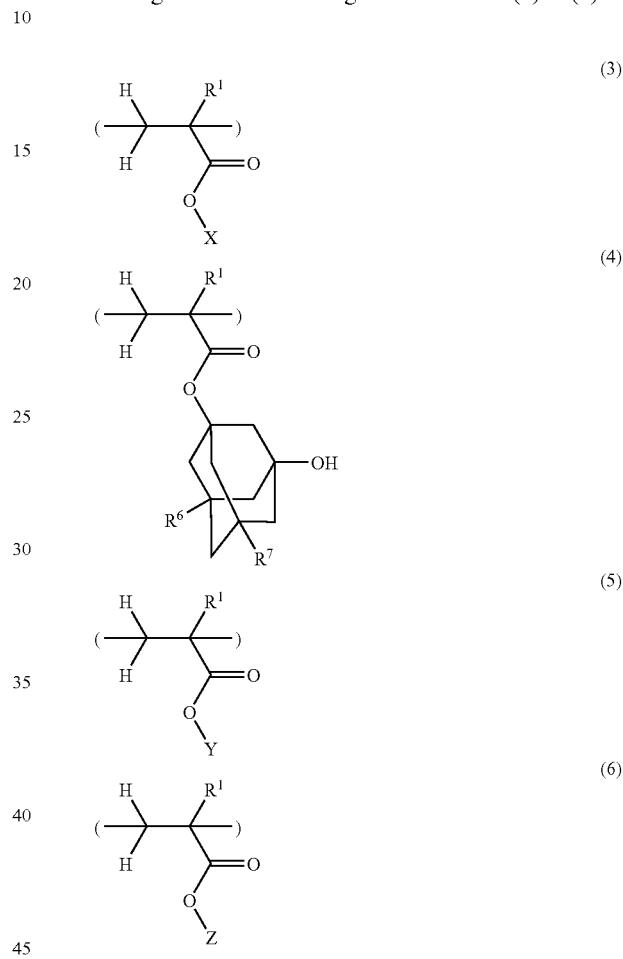

Herein $R^1$ is as defined above, $R^6$ and $R^7$ are each independently hydrogen or hydroxyl, X is an acid labile group, Y is a substituent group having a lactone structure different from formula (1), and Z is hydrogen, a fluoroalkyl group of 1 to 15 carbon atoms or a fluoroalcohol-containing substituent group of 1 to 15 carbon atoms.

[5] A resist composition comprising the polymer of any one of [2] to [4] as a base resin.

[6] A process for forming a pattern comprising the steps of applying the resist composition of [5] onto a substrate to form a resist coating, heat treating the resist coating, exposing the resist coating to high-energy radiation or electron beam through a photomask, optionally heat treating the exposed coating, and developing it with a developer.

[7] A process for forming a pattern comprising the steps of applying the resist composition of [5] onto a substrate to form a resist coating, heat treating the resist coating, exposing the resist coating to high-energy radiation or electron beam through a photomask, heat treating the exposed coating, and developing it with a developer, said exposing step being performed by immersion lithography including holding a liquid having a refractive index of at least 1.0 between the resist coating and a projection lens.

[8] A process for forming a pattern comprising the steps of applying the resist composition of [5] onto a substrate to form a resist coating, heat treating the resist coating, forming a protective film on the resist coating, exposing the resist coating to high-energy radiation or electron beam through a photomask, heat treating the exposed coating, and developing it with a developer, said exposing step being performed by immersion lithography including holding a liquid having a refractive index of at least 1.0 between the protective film and a projection lens.

ADVANTAGEOUS EFFECTS OF INVENTION

The lactone-containing compounds of the invention are useful as raw materials for the synthesis of functional materials, pharmaceutical and agricultural chemicals. They are most useful as monomers to produce polymers for the manufacture of radiation-sensitive resist compositions which have high transparency to radiation having a wavelength of up to 500 nm, especially up to 300 nm, and exhibit good development properties. Radiation-sensitive resist compositions comprising the polymers as base resin exhibit high resolution and are improved in pattern edge roughness, pattern density dependency and exposure margin when processed by photolithography. The polymers are advantageously used in resist form for precise micropatterning.

DESCRIPTION OF THE PREFERRED EMBODIMENT

The singular forms "a," "an" and "the" include plural referents unless the context clearly dictates otherwise.

The notation (Cn-Cm) means a group containing from n to m carbon atoms per group.

It is understood that for many structures represented by chemical formulae, there can exist enantiomers and diastereomers. Unless otherwise stated, a single formula collectively represents all such stereoisomers. The stereoisomers may be used alone or in admixture.

Lactone-Containing Compound

The lactone-containing compounds of the invention have the general forma (1).

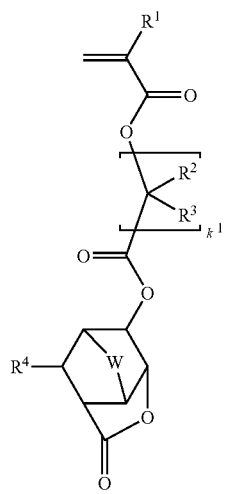

(1)

Herein $R^1$ is a hydrogen atom, fluorine atom, methyl group or trifluoromethyl group. $R^2$ and $R^3$ are each independently a hydrogen atom or a straight, branched or cyclic monovalent hydrocarbon group of 1 to 10 carbon atoms, or $R^2$ and $R^3$ may bond together to form an aliphatic hydrocarbon ring with the carbon atom to which they are attached. $R^4$ is a hydrogen atom or $CO_2R^5$ wherein $R^5$ is a straight, branched or cyclic monovalent hydrocarbon group of 1 to 15 carbon atoms which may have one or more halogen or oxygen atoms. W is $CH_2$, O or S, with the proviso that $R^4$ is $CO_2R^5$ when W is $CH_2$, and $R^4$ is hydrogen or $CO_2R^5$ when W is O or S. The subscript $k^1$ is an integer of 3 to 5.

Examples of the straight, branched or cyclic monovalent $C_1$-$C_{10}$ hydrocarbon group represented by $R^2$ and $R^3$ include, but are not limited to, methyl, ethyl, n-propyl, isopropyl, n-butyl, sec-butyl, isobutyl, tert-butyl, cyclopentyl, cyclohexyl, 2-ethylhexyl, and n-octyl. $R^2$ and $R^3$ may be the same or different. The aliphatic hydrocarbon rings that $R^2$ and $R^3$ together form with the carbon atom to which they are attached are preferably those of 3 to 20 carbon atoms, more preferably 4 to 15 carbon atoms, and examples include cyclopropane, cyclobutane, cyclopentane, cyclohexane, bicyclo[2.2.1]heptane, bicyclo[2.2.2]octane, bicyclo[3.3.1]nonane, bicyclo[4.4.0]decane, and adamantane.

Examples of $R^5$ include, but are not limited to, methyl, ethyl, n-propyl, isopropyl, n-butyl, sec-butyl, isobutyl, tert-butyl, cyclopentyl, cyclohexyl, 1-methylcyclopentyl, 1-ethylcyclopentyl, 1-isopropylcyclopentyl, 1-(tert-butyl)cyclopentyl, 1-methylcyclohexyl, 1-ethylcyclohexyl, 2-ethylhexyl, n-octyl, 2-methyl-2-bicyclo[2.2.1]heptyl, 2-ethyl-2-bicyclo[2.2.1]heptyl, 2-methyl-2-adamantyl, 2-ethyl-2-adamantyl, 2-isopropyl-2-adamantyl, 2-(1-adamantyl)-2-propyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, 3-ethyl-3-tetracyclo[4.4.0.1$^{2,5}$.1$^{7,10}$] dodecyl, methoxymethyl, ethoxymethyl, methoxyethyl, ethoxyethyl, and methoxyethoxyethyl, as well as the groups shown below.

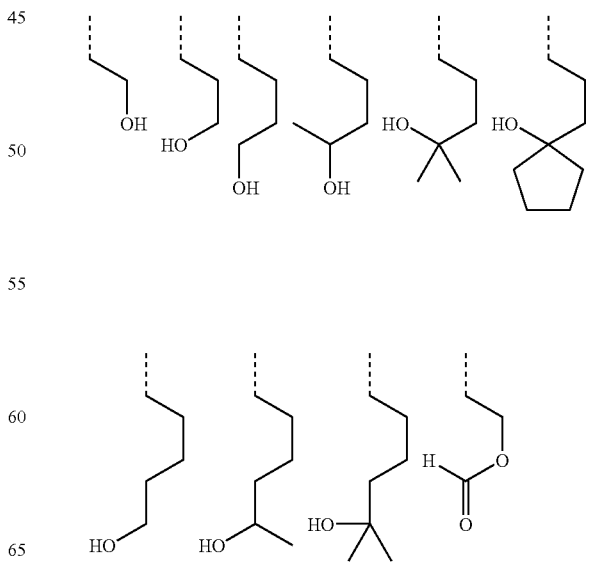

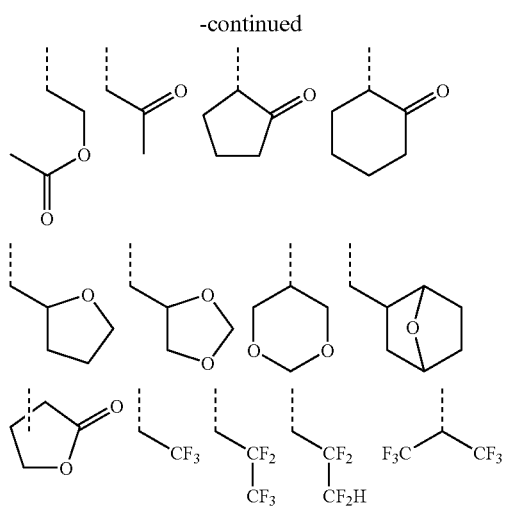
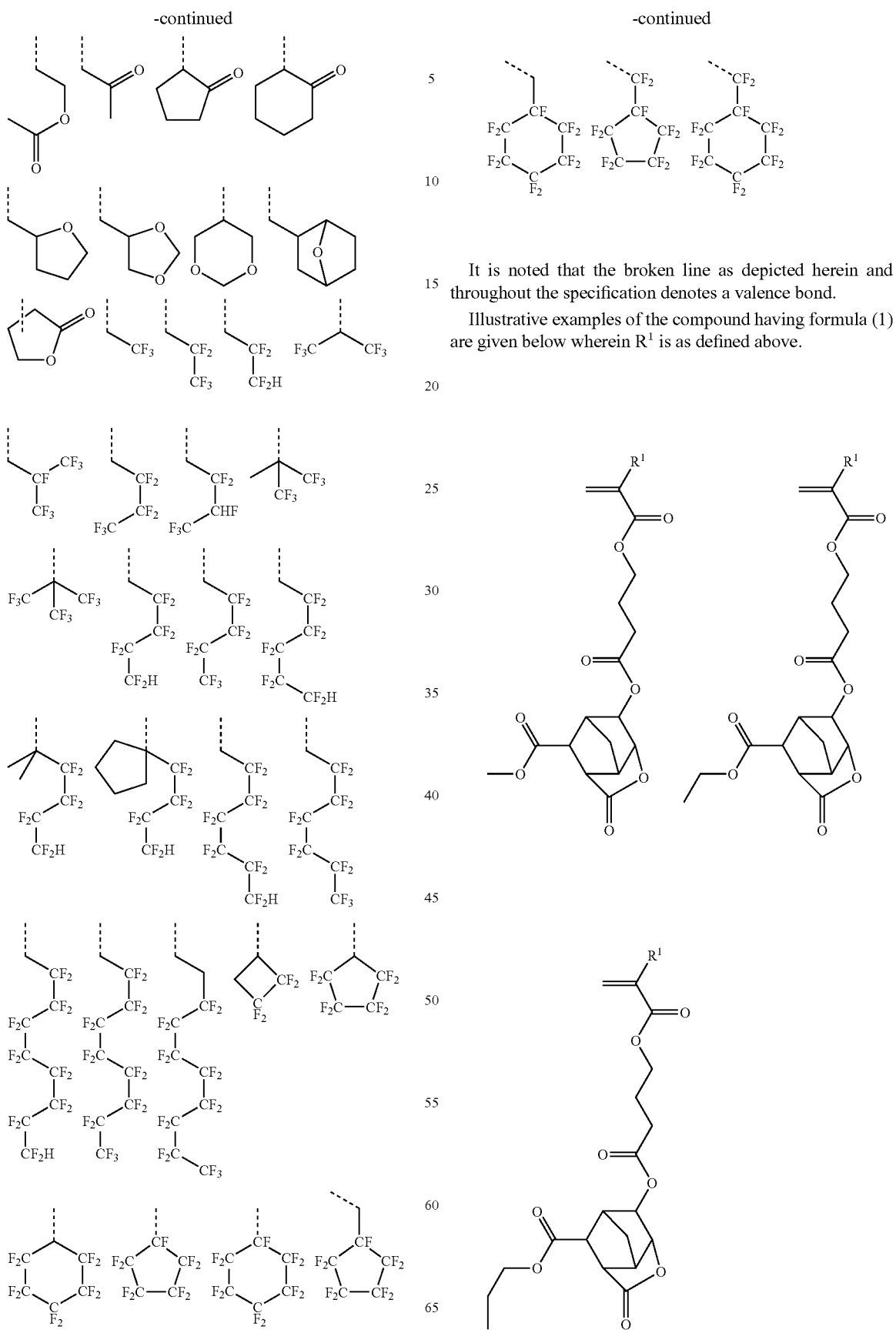
It is noted that the broken line as depicted herein and throughout the specification denotes a valence bond.
Illustrative examples of the compound having formula (1) are given below wherein $R^1$ is as defined above.

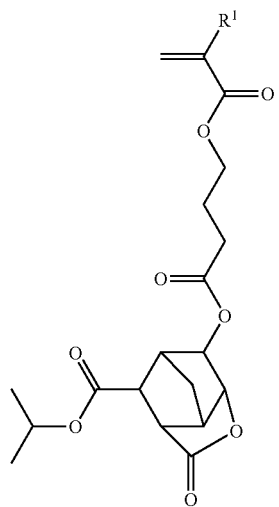
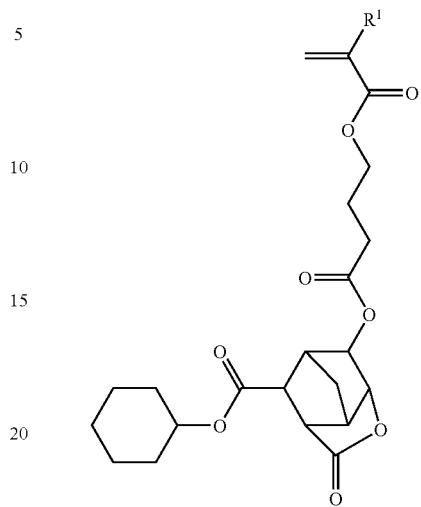
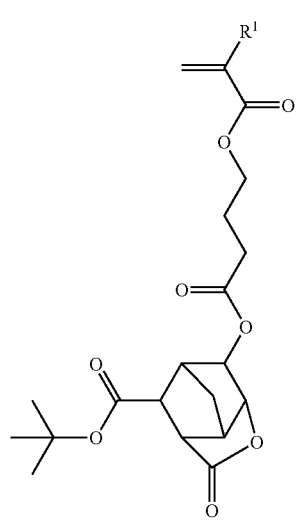
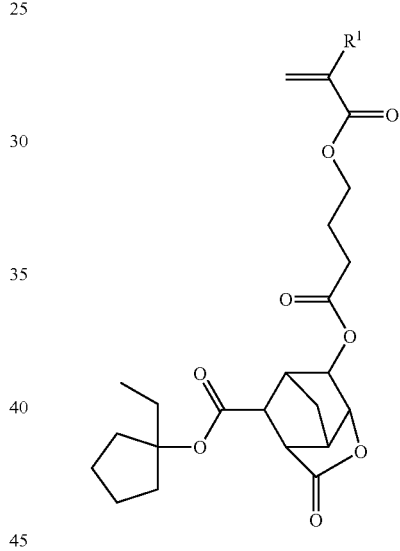
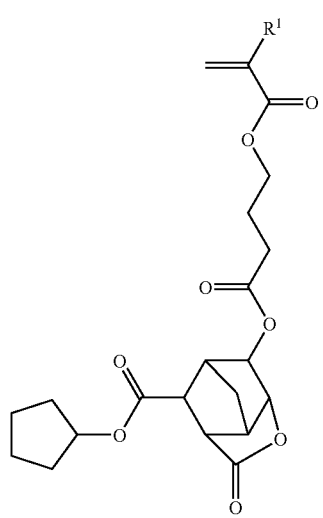
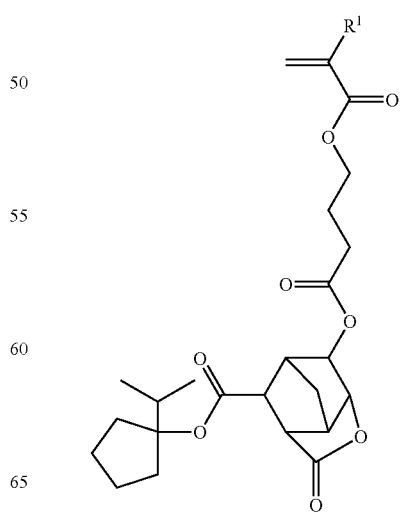

-continued
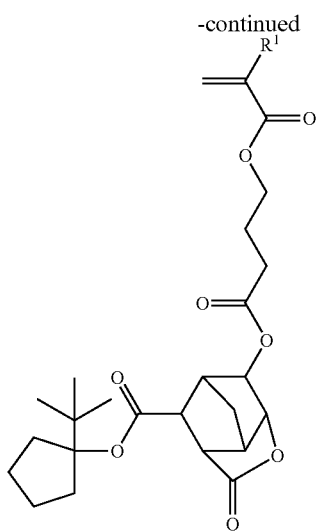
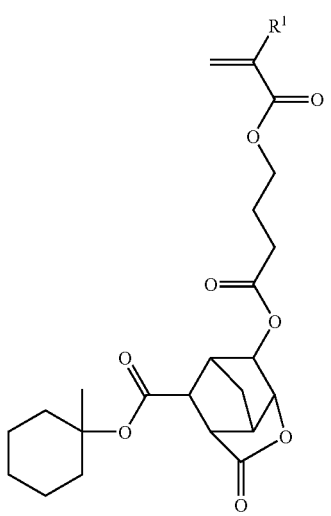
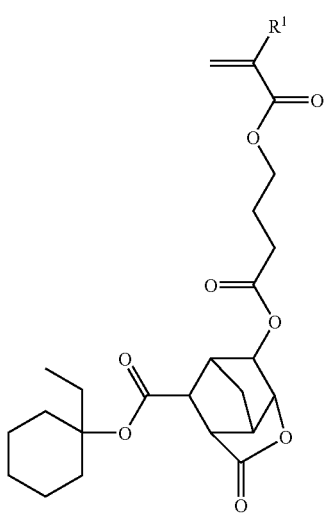
-continued
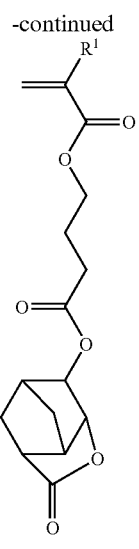
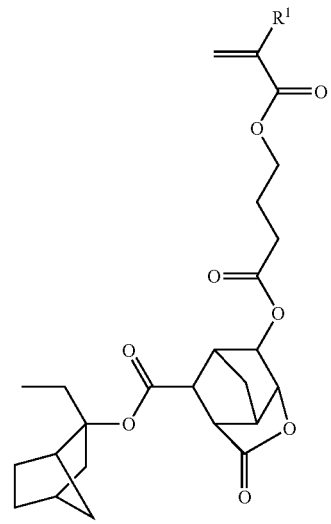
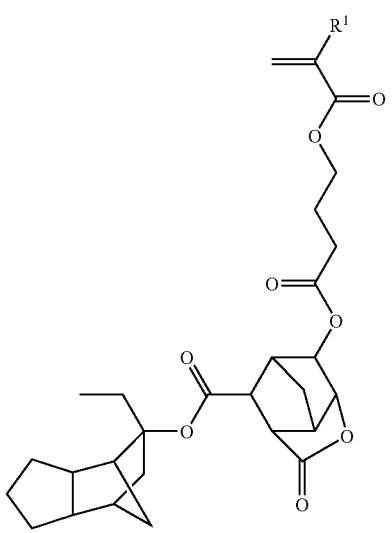

-continued
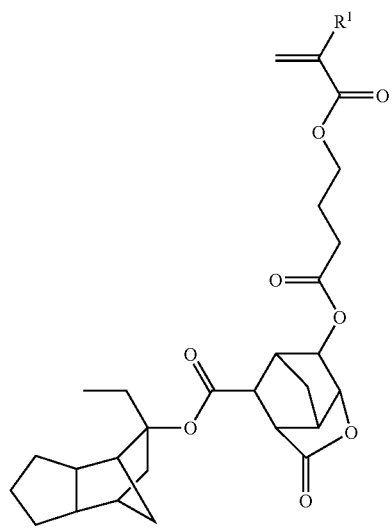
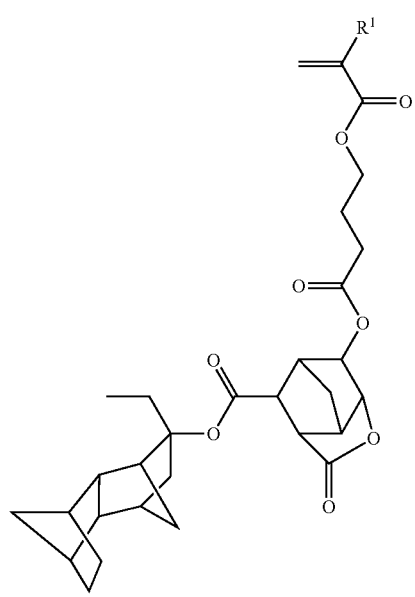
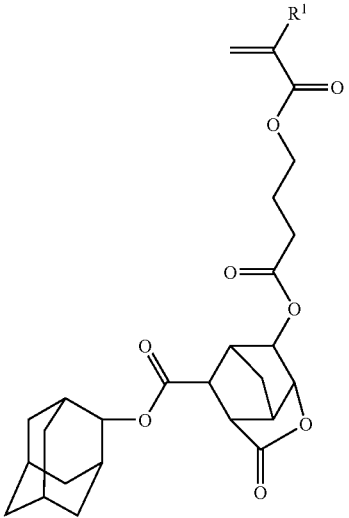
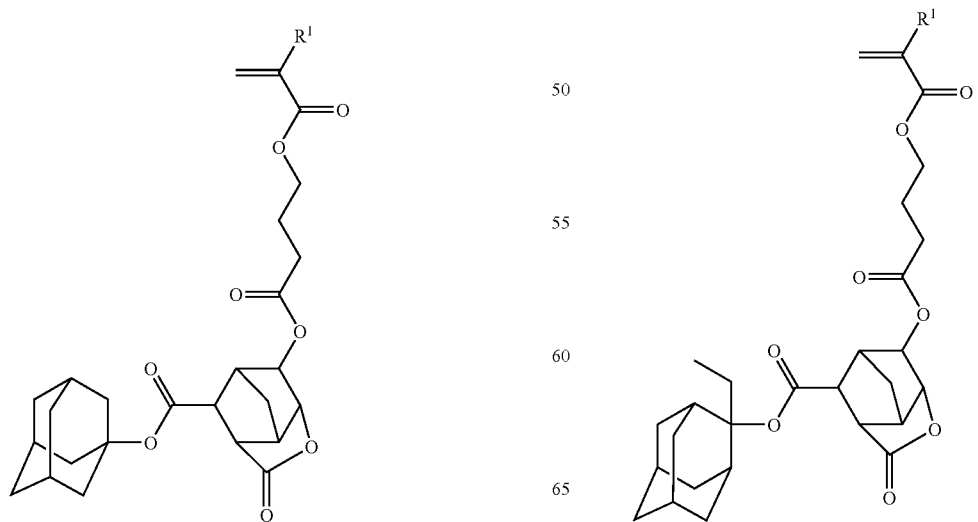

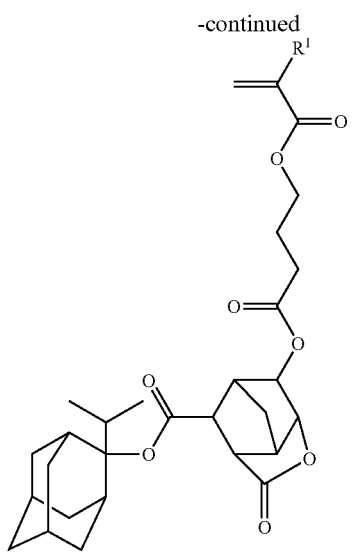
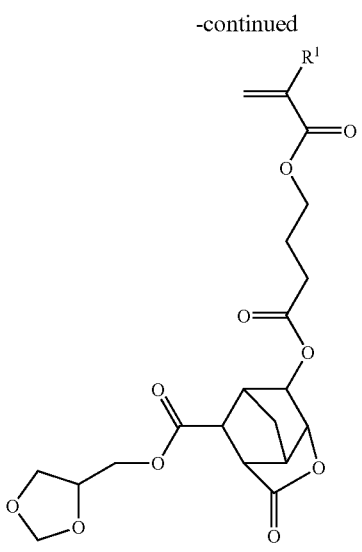
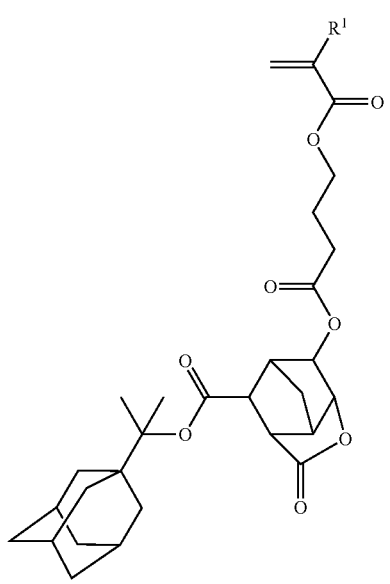
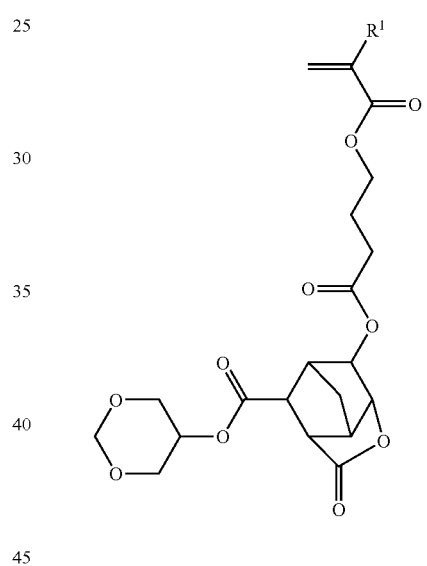
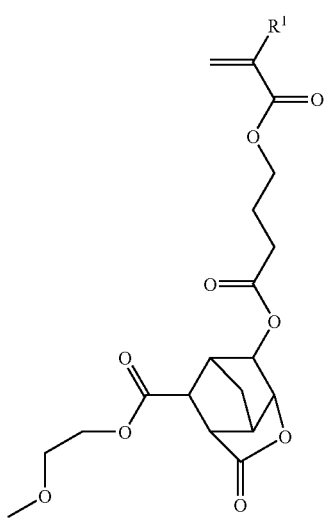
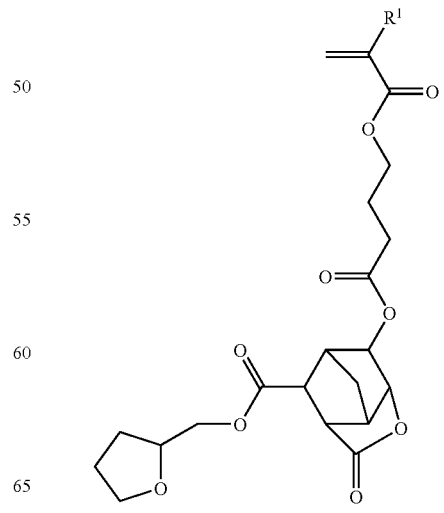

-continued
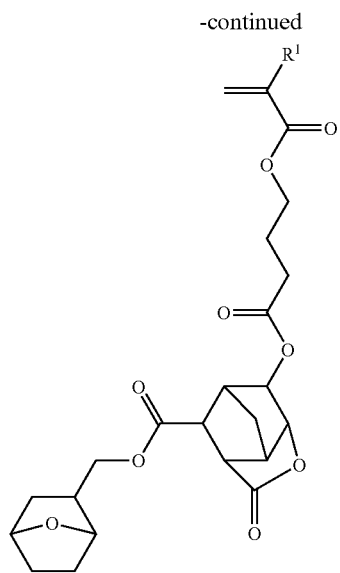
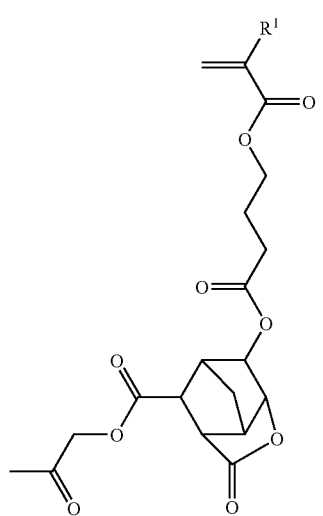
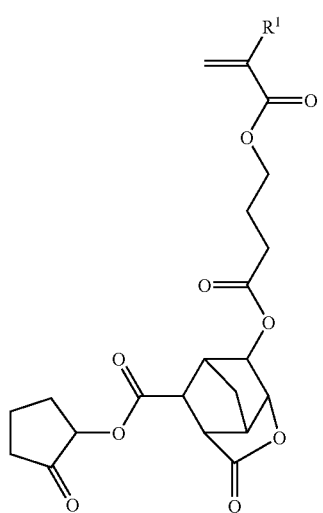
-continued
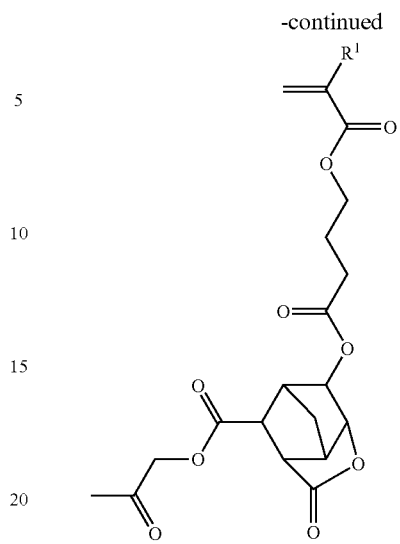
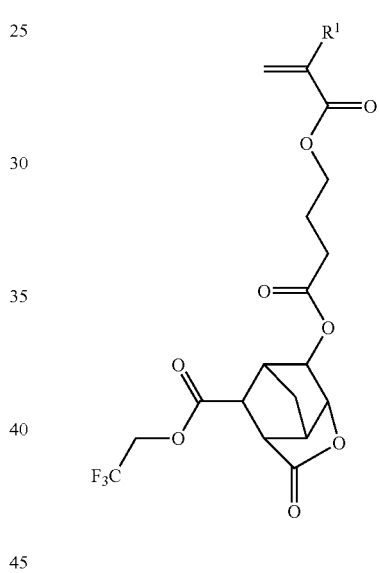
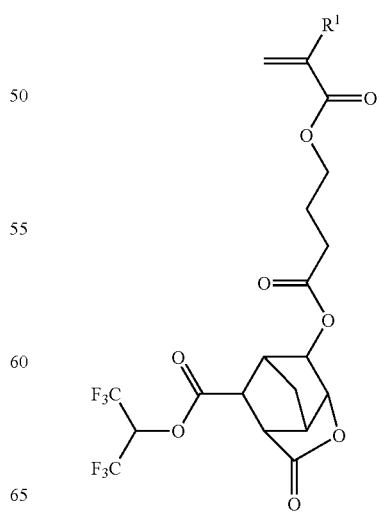

-continued
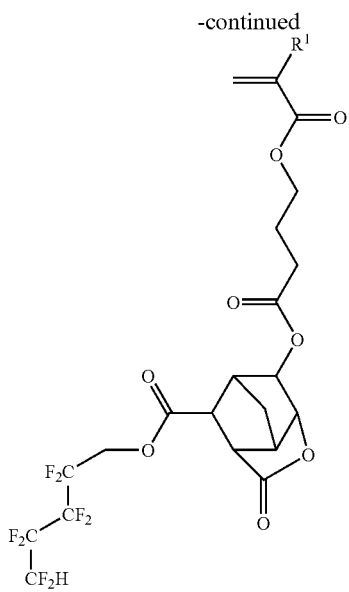
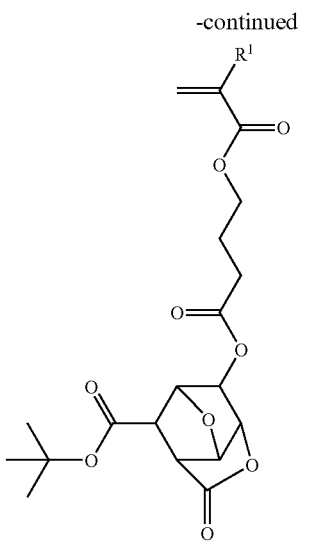
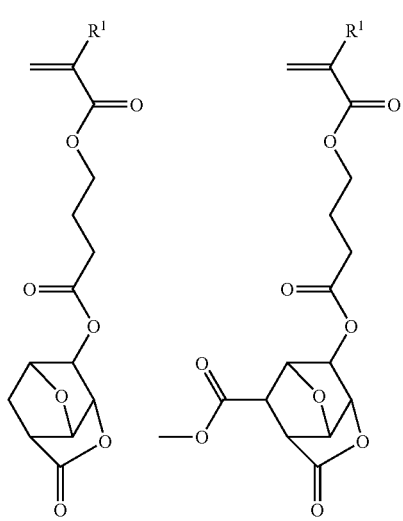
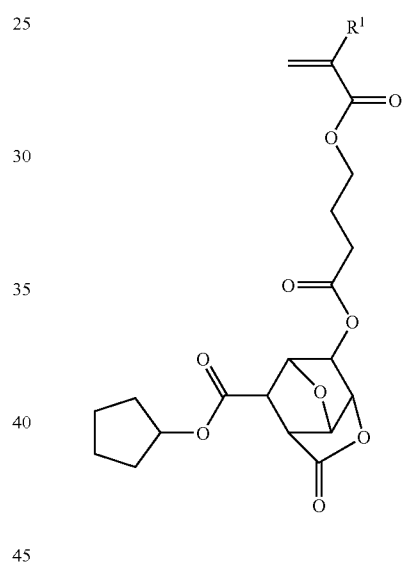
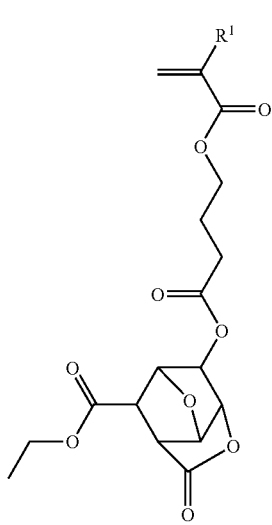
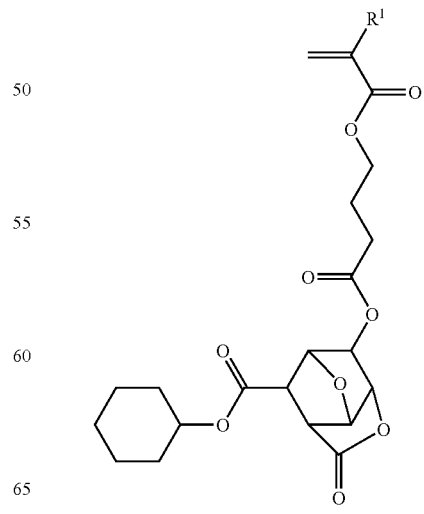

-continued
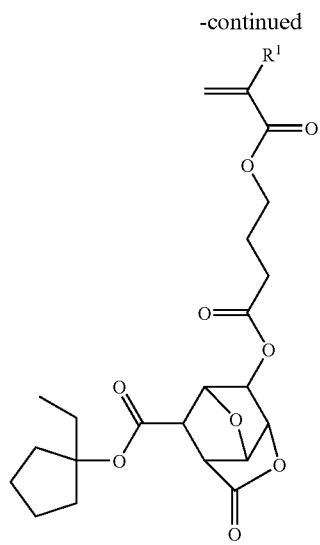
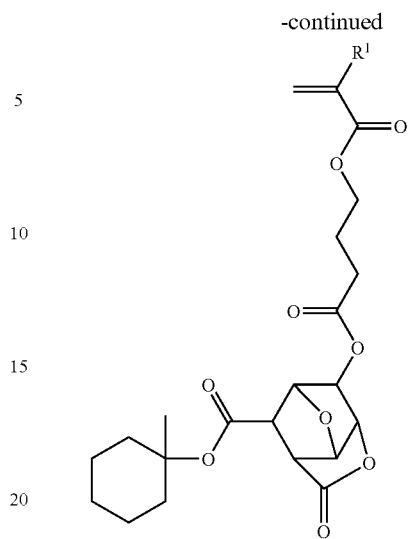
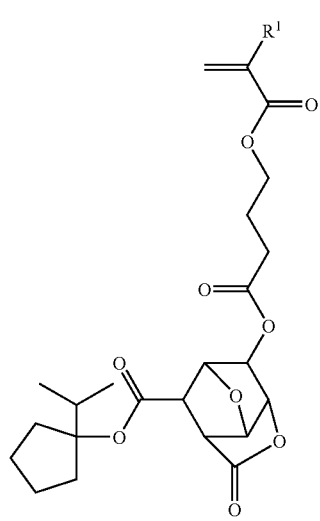
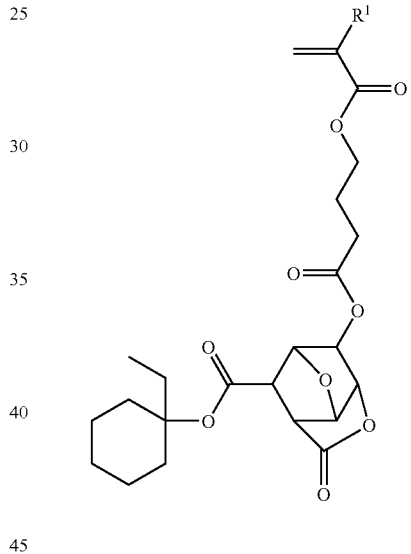
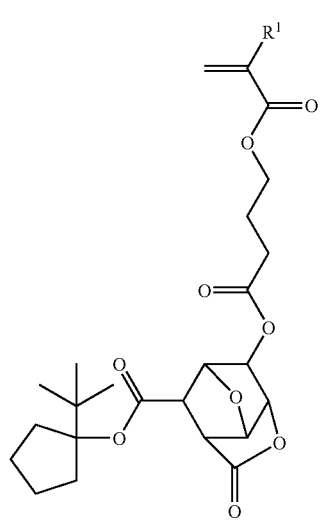
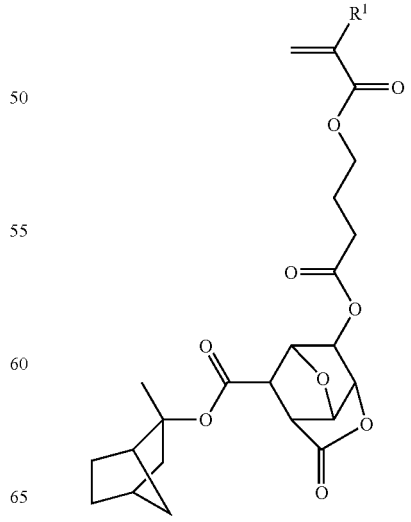

-continued
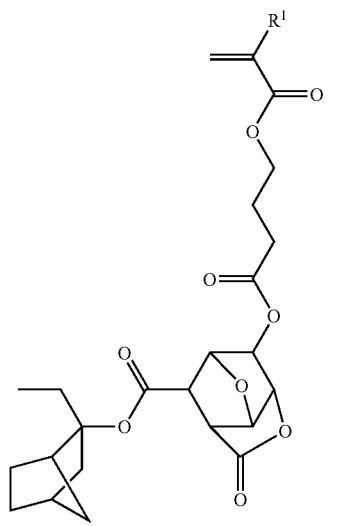
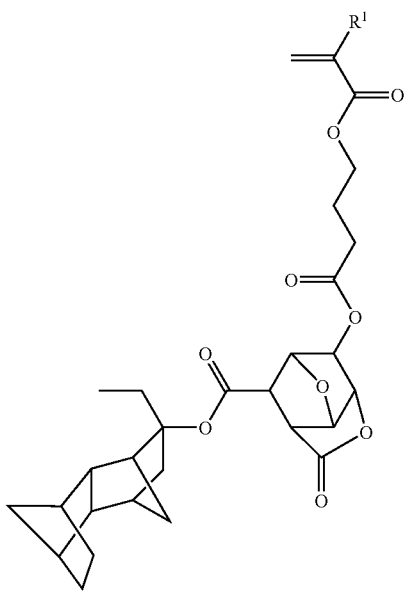
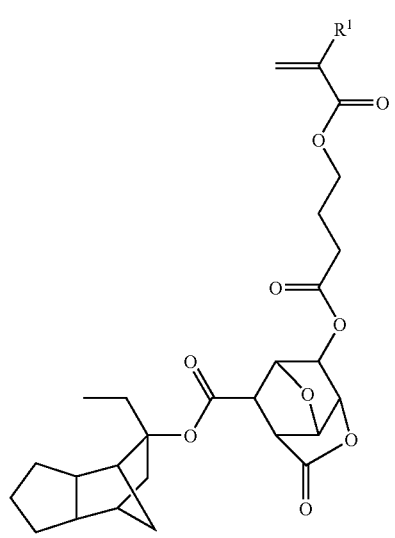
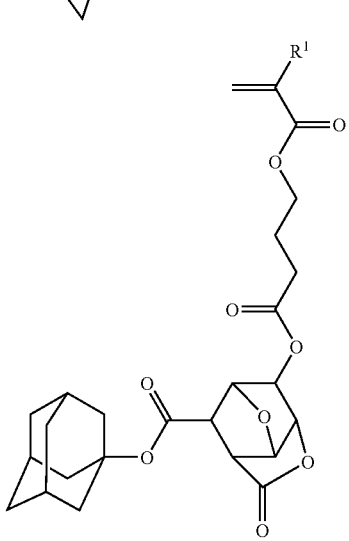
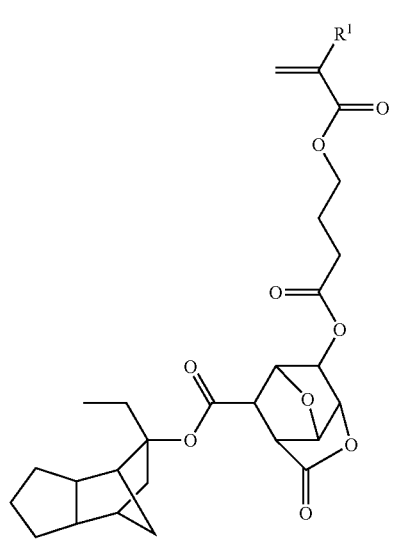
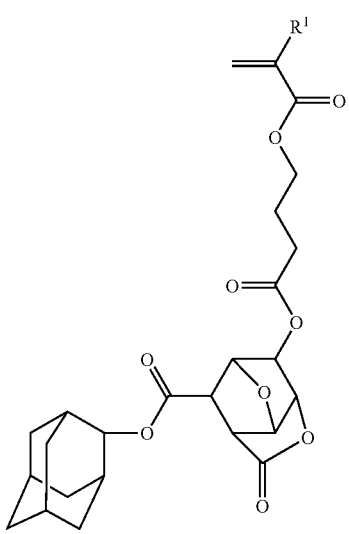

-continued
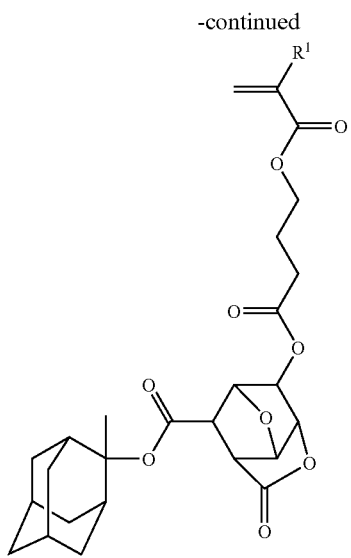
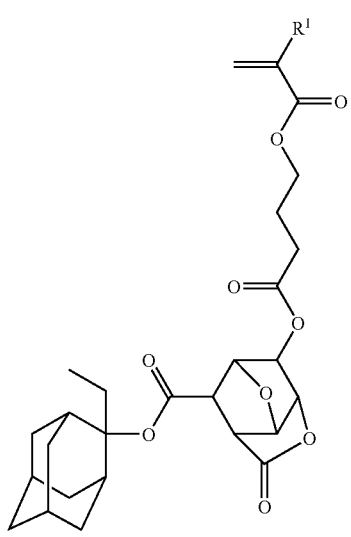
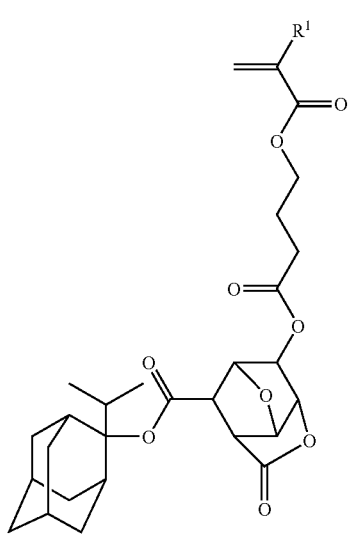
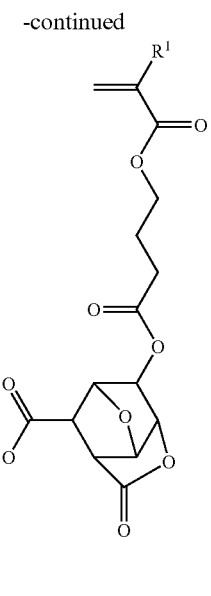
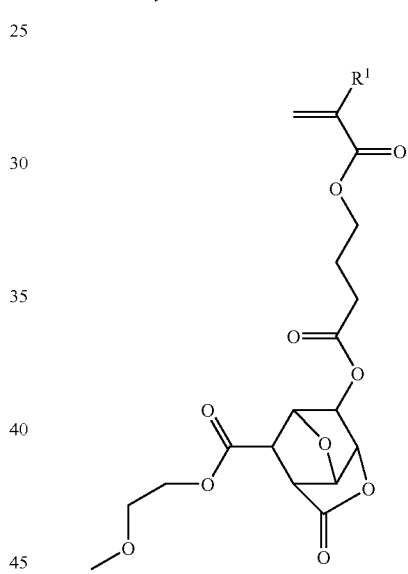
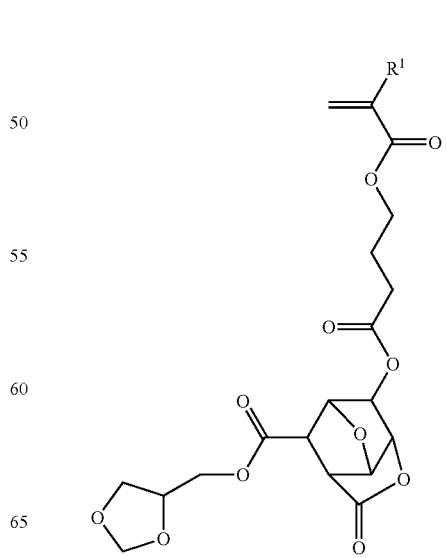

-continued
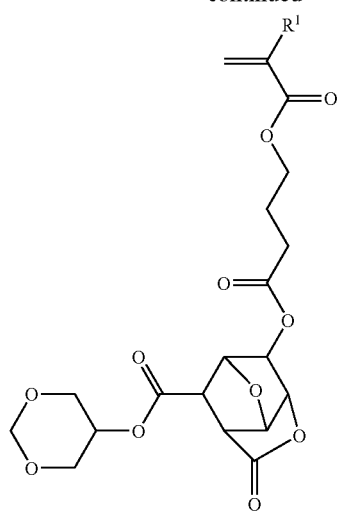
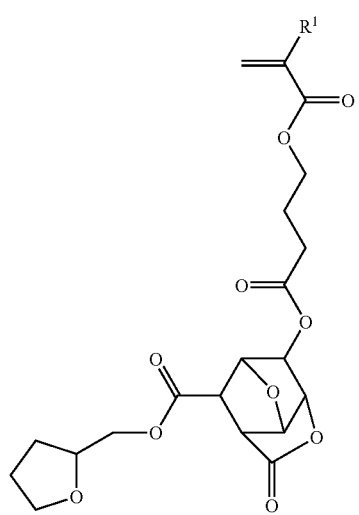
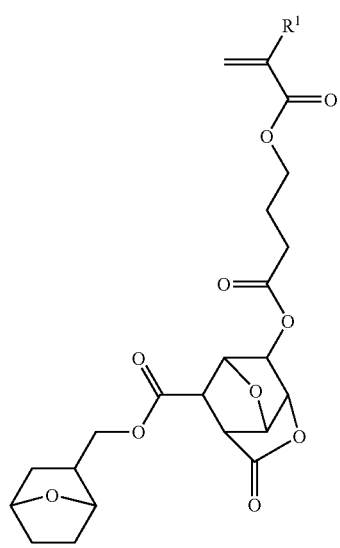
-continued
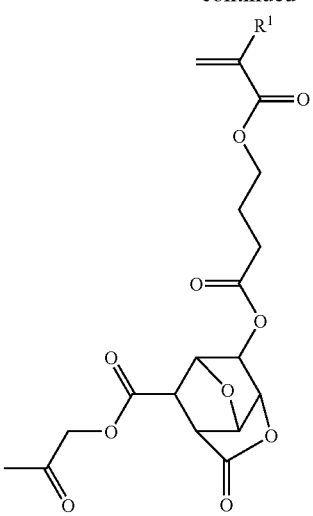
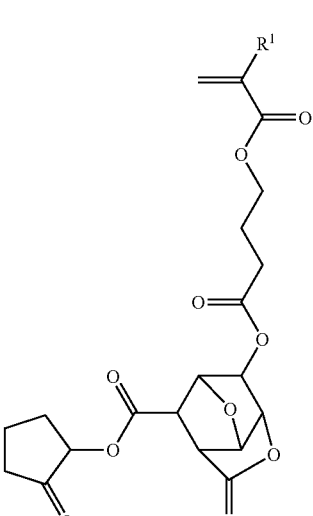
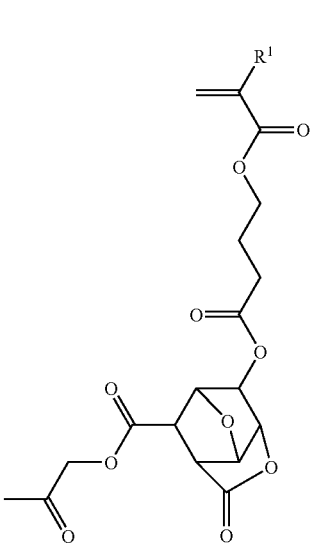

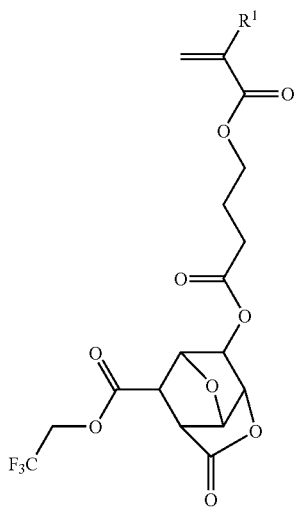
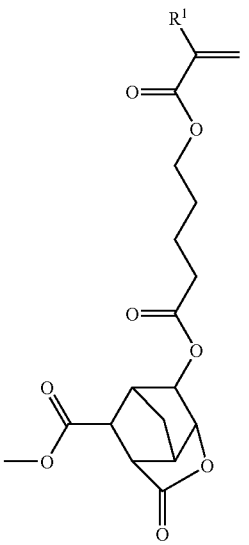
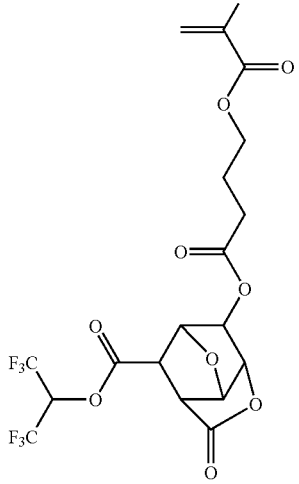
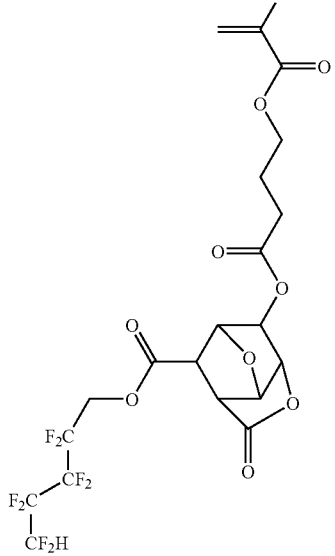

31
-continued
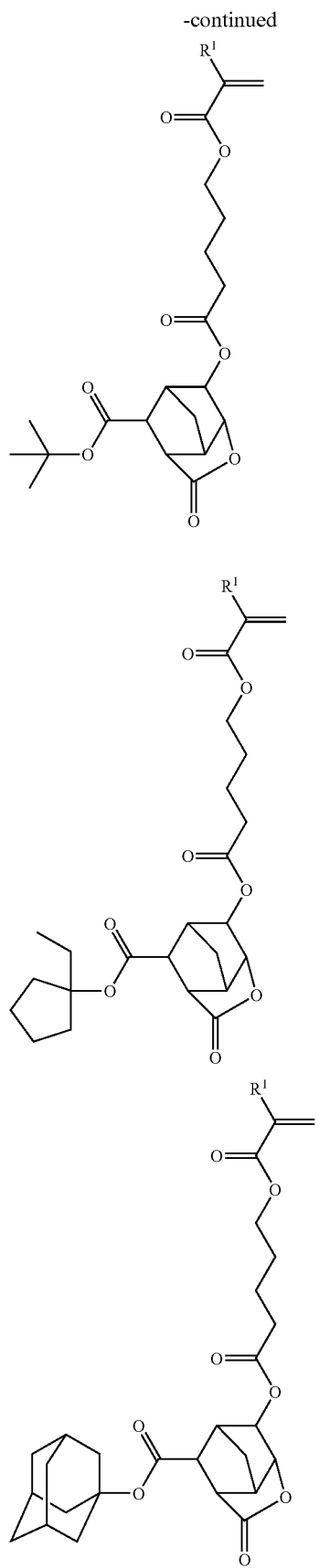
32
-continued
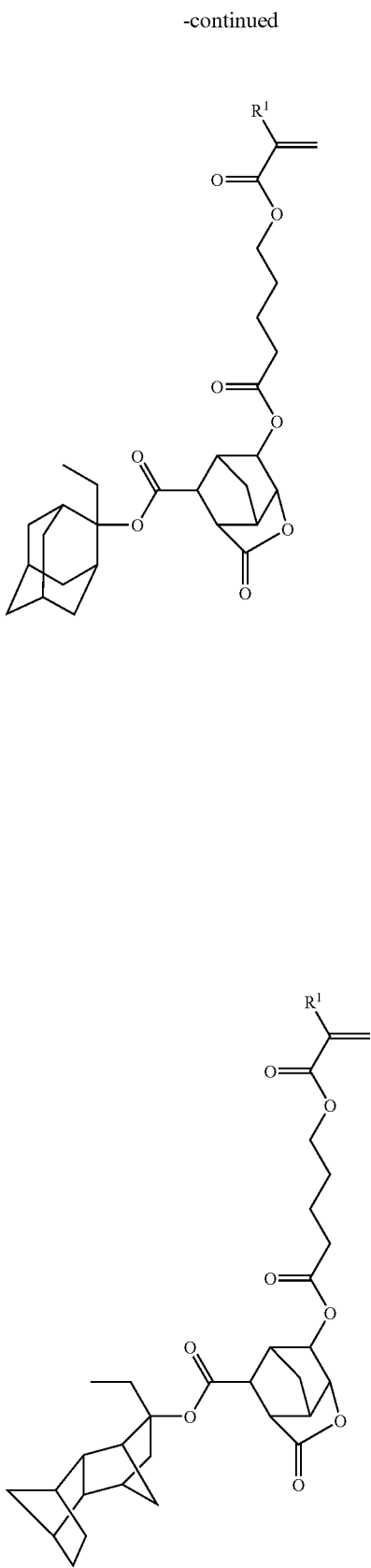

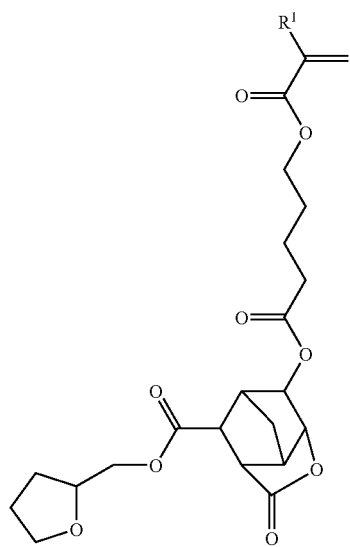
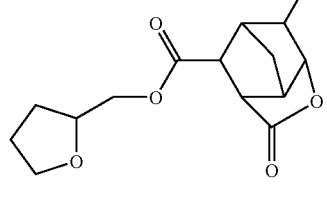
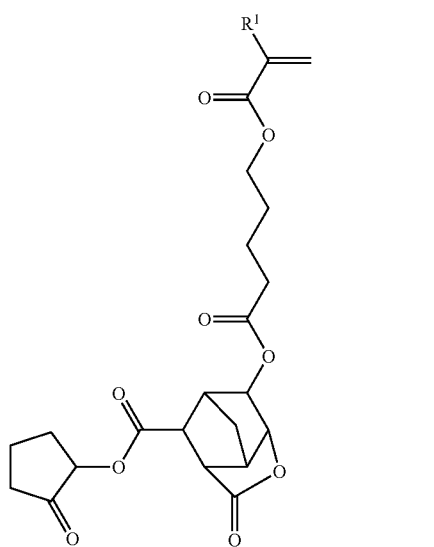
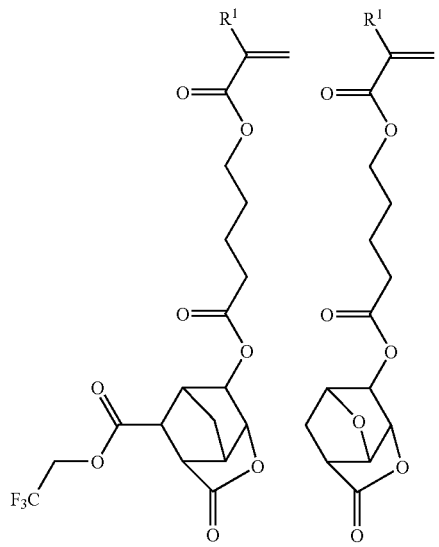
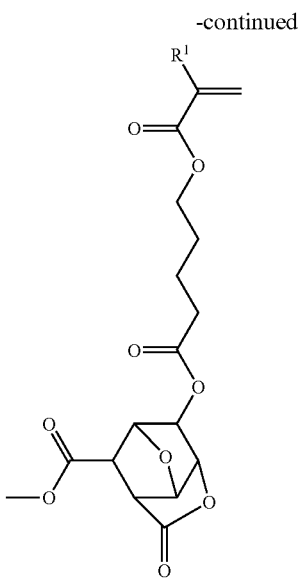
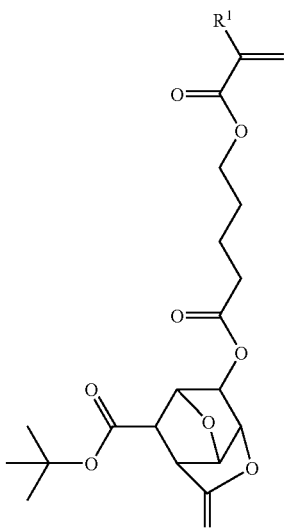
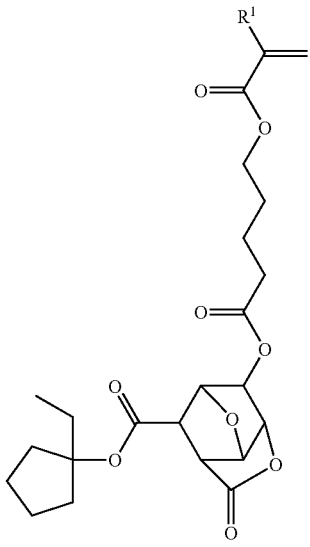

-continued
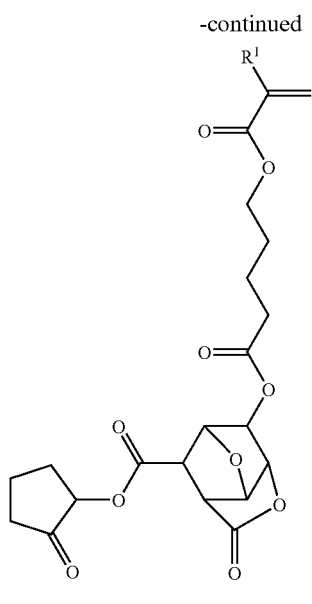
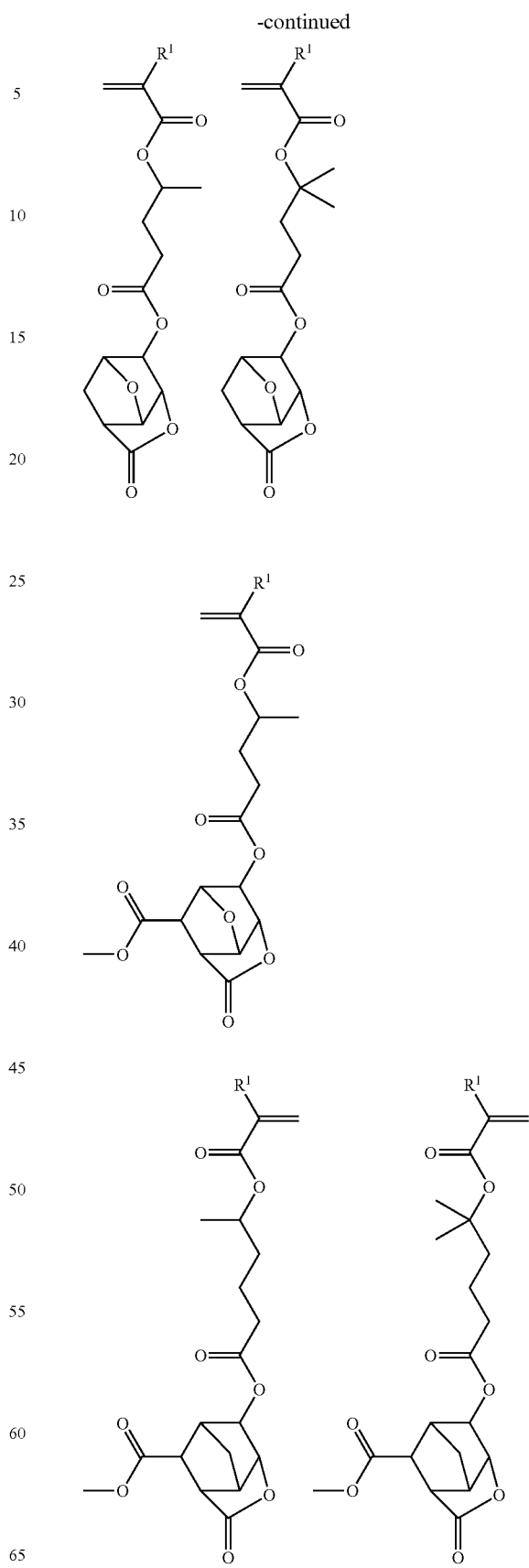

-continued
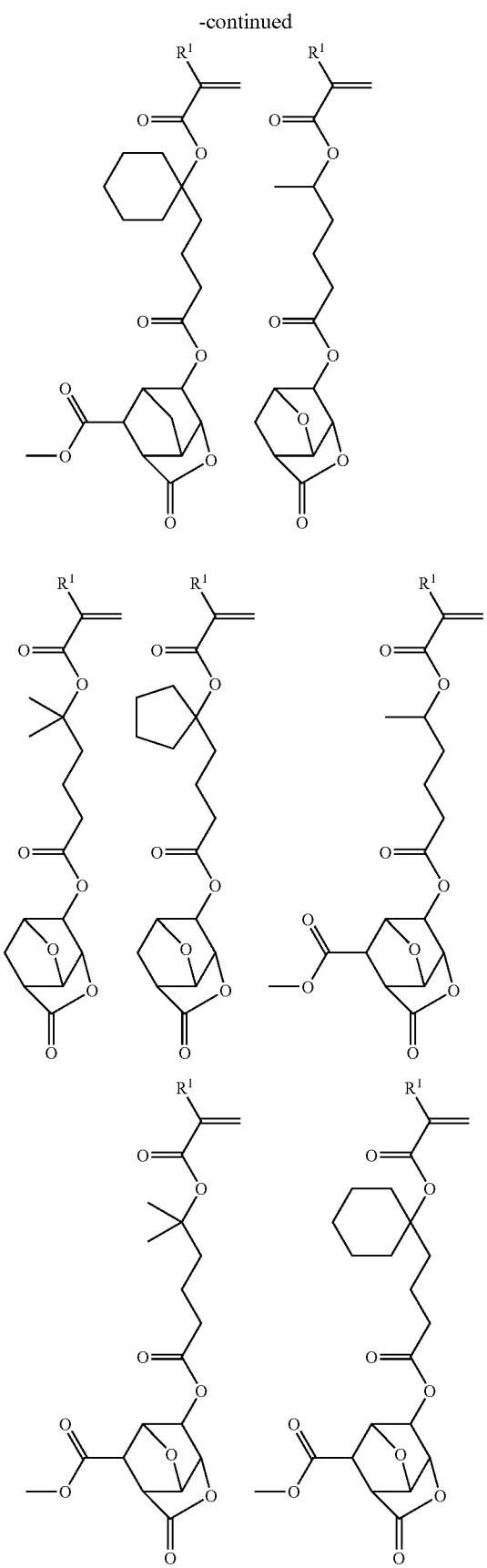
-continued
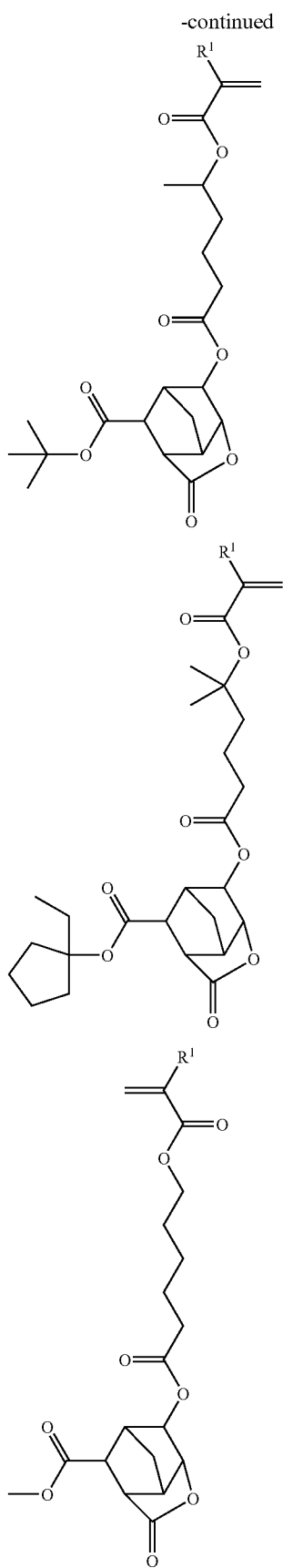

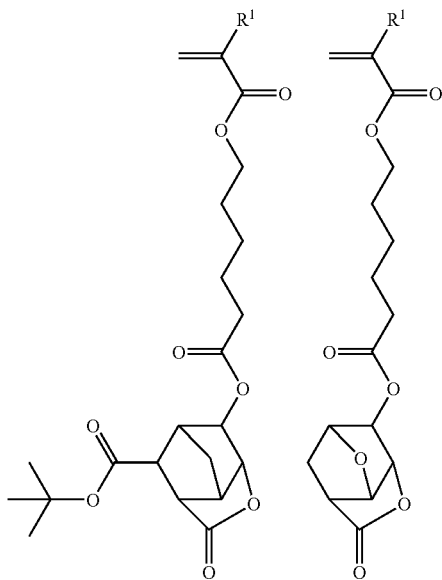
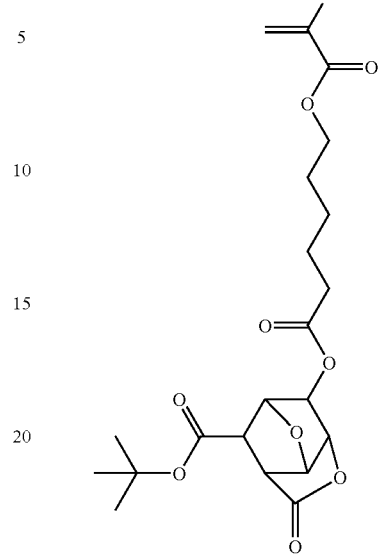
The lactone-containing compounds of formula (1) can be produced by the reaction scheme A shown below, for example, but the invention is not limited thereto.
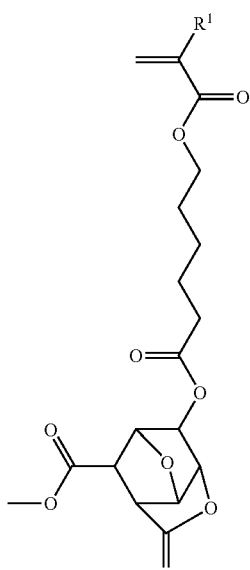
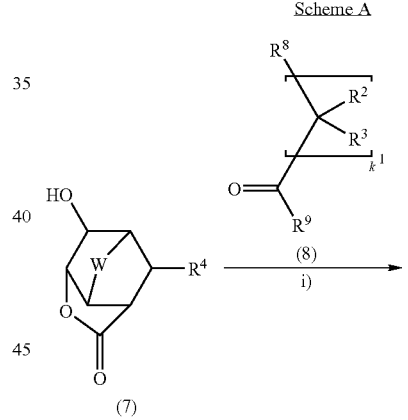
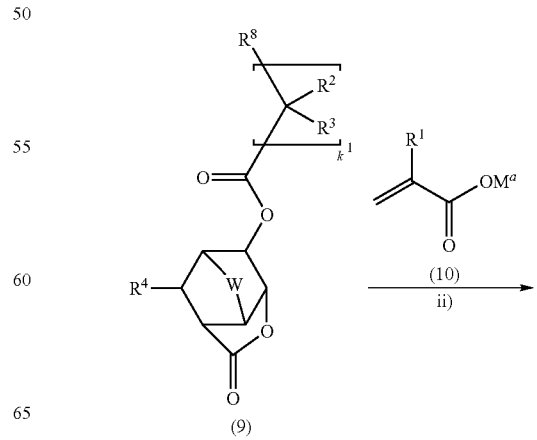

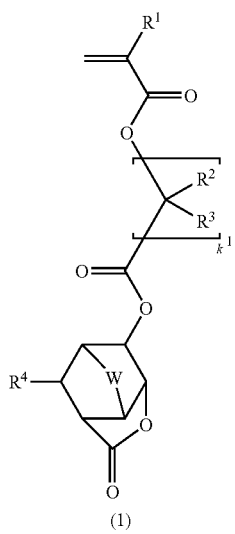

(1)

Herein, $R^1$ to $R^4$, W, and $k^1$ are as defined above. $R^8$ is a halogen atom. $R^9$ is a halogen atom, hydroxyl group or —$OR^{10}$. $R^{10}$ is methyl, ethyl or a group of the formula:

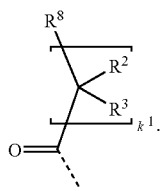

$M^a$ is Li, Na, K, $Mg_{1/2}$, $Ca_{1/2}$ or a substituted or unsubstituted ammonium.

More particularly, scheme A includes step (i) which is a reaction of a hydroxylactone compound (7) with an esterifying agent (8) into a halo-ester compound (9).

Notably, the synthesis of hydroxylactone compound (7) is described in JP-A 2000-159758 and U.S. Ser. No. 11/649,251 (Japanese Patent Application No. 2006-001102). For example, hydroxylactone compound (7) wherein $R^4$ is $CO_2R$ can be synthesized according to the following formula.

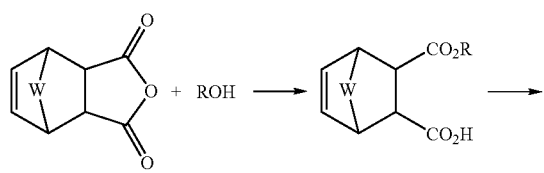

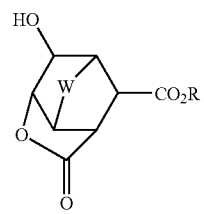

The reaction may be readily conducted by a well-known technique. The preferred esterifying agent (8) is an acid chloride (corresponding to formula (8) wherein $R^9$ is chlorine) or a carboxylic acid (corresponding to formula (8) wherein $R^9$ is hydroxyl). When an acid chloride is used as the esterifying agent, the reaction may be conducted in a solventless system or in a solvent such as methylene chloride, toluene, hexane, diethyl ether, tetrahydrofuran or acetonitrile, by sequentially or simultaneously adding hydroxylactone compound (7), a corresponding acid chloride such as 4-chlorobutyric acid chloride or 4-bromobutyric acid chloride, and a base such as triethylamine, pyridine or 4-dimethylaminopyridine, and optionally cooling or heating. When a carboxylic acid is used as the esterifying agent, the reaction may be conducted in a solvent such as toluene or hexane, by heating hydroxylactone compound (7) and a corresponding carboxylic acid such as 4-chlorobutyric acid or 4-bromobutyric acid, in the presence of an acid catalyst, and optionally removing the water formed during reaction from the system. Examples of the acid catalyst used herein include mineral acids such as hydrochloric acid, sulfuric acid, nitric acid and perchloric acid, and organic acids such as p-toluenesulfonic acid and benzenesulfonic acid.

Step (ii) is a reaction of a halo-ester compound (9) (formula (9) wherein $R^8$ is a halogen atom) with a carboxylate salt (10) into a lactone-containing compound (1).

The reaction may be conducted by a standard technique. The carboxylic acid salt (10) used herein may be any of commercially available carboxylic acid salts such as metal salts of carboxylic acids, or may be prepared in a reaction system using a corresponding carboxylic acid such as methacrylic acid or acrylic acid and a base. The amount of carboxylic acid salt (10) used is preferably 0.5 to 10 moles, and more preferably 1.0 to 3.0 moles per mole of the reactant, halo-ester (9). With less than 0.5 mole of the carboxylic acid salt, a large proportion of the reactant may be left unreacted, leading to a substantial drop of yield. Using more than 10 moles of the carboxylic acid salt may be uneconomical because of an increased cost of the salt and decreased pot yields. When the carboxylic acid salt is prepared in a reaction system using a corresponding carboxylic acid and a base, the base used herein may be selected from among amines such as ammonia, triethylamine, pyridine, lutidine, collidine, and N,N-dimethylaniline; hydroxides such as sodium hydroxide, potassium hydroxide, and tetramethylammonium hydroxide; carbonates such as potassium carbonate and sodium hydrogen carbonate; metals such as sodium; metal hydrides such as sodium hydride; metal alkoxides such as sodium methoxide and potassium t-butoxide; organometallic compounds such as butyllithium and ethylmagnesium bromide; and metal amides such as lithium diisopropylamide, and mixtures thereof. The amount of the base used is preferably 0.2 to 10 moles, and more preferably 0.5 to 2.0 moles per mole of the carboxylic acid. With less than 0.2 mole of the base, a large proportion of the carboxylic acid may run to waste, leading to a cost deficiency. With more than 10 moles of the base, substantial side reactions may occur, resulting in a substantial drop of yield.

A solvent may be used in the reaction of step (ii). Suitable solvents include hydrocarbons such as toluene, xylene, hexane and heptane; chlorinated solvents such as methylene chloride, chloroform and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide, and dimethyl sulfoxide; and water, which may be used alone or in admixture. To the reaction system, a phase transfer catalyst such as tetrabutylammonium hydrogen sulfate may be added. An appropriate amount of the phase transfer catalyst added is 0.0001 to 1.0 mole, and more preferably 0.001 to 0.5 mole per mole of the reactant, alcohol compound. Less than 0.0001 mole of the catalyst may exert little or no addition effect whereas more than 1.0 mole may be uneconomical because of an increased expense.

For the esterification reaction described above, the reaction temperature may be selected as appropriate in accordance with other reaction conditions and is preferably in the range from −70° C. to approximately the boiling point of the solvent, and more preferably in the range from 0° C. to approximately the boiling point of the solvent. The higher the reaction temperature, the more outstanding become side reactions. It is then important in attaining high yields that the reaction be carried out at as low a temperature as possible in the range for the reaction to proceed at a practically acceptable rate. Preferably the reaction time is determined so as to attain increased yields by monitoring the reaction process by thin-layer chromatography (TLC) or gas chromatography (GC). Usually, the reaction time is about 30 minutes to about 40 hours. From the reaction mixture, the lactone-containing compound (1) is recovered through an ordinary aqueous workup. If necessary, the compound may be purified by a standard technique such as distillation, recrystallization or chromatography.

It is to be noted that US 20080026331 A1 (JP-A 2008-031298) discloses analogous lactone-containing compounds of formula (1) wherein $k^1$ is 1 or 2, referred to as "short-chain lactone compounds," hereinafter. In the synthesis of a polymer from this short-chain lactone compound, the polarity of an overall polymer is sometimes biased extremely to the hydrophilic side so that the polymer may experience a loss of solubility in organic solvents, depending on a particular proportion of this monomer incorporated. In contrast, the use of the lactone compound of the invention permits a polymer to be improved in organic solvent solubility by a choice of $k^1$ in formula (1) so as to provide a properly controlled polarity. Those compounds of formula (1) wherein $k^1$ is equal to or more than 6 are undesirable because inversely an overall polymer derived therefrom is increased in fat-solubility at the sacrifice of solvent solubility.

Polymer

In the second aspect, the invention provides a polymer comprising recurring units derived from the lactone-containing compound of formula (1).

Specifically, the recurring units derived from the lactone-containing compound of formula (1) include recurring units having the general formula (2).

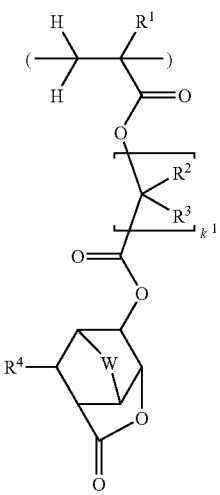

(2)

Herein $R^1$ to $R^4$, W and $k^1$ are as defined above.

In addition to the recurring units derived from the compounds having formula (1), specifically recurring units having formula (2), the polymers of the invention may further comprise recurring units having at least one of the general formulas (3) to (6).

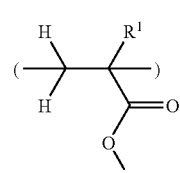

(3)

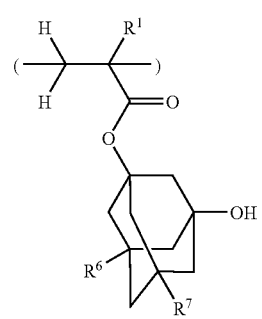

(4)

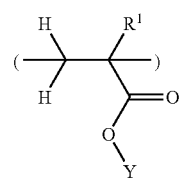

(5)

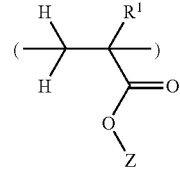

(6)

Herein $R^1$ is as defined above, $R^6$ and $R^7$ are each independently a hydrogen atom or hydroxyl group, X is an acid labile group, Y is a substituent group having a lactone structure different from formula (1), and Z is a hydrogen atom, a fluoroalkyl group of 1 to 15 carbon atoms or a fluoroalcohol-containing substituent group of 1 to 15 carbon atoms.

Under the action of acid, a polymer comprising recurring units of formula (3) is decomposed to generate carboxylic acid, turning to be an alkali soluble polymer. The acid labile group represented by X may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

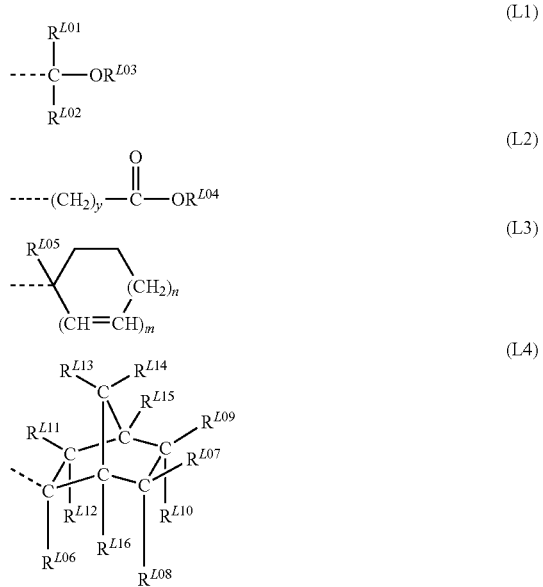

In these formulae, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, n-propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples of the substituted alkyl groups are shown below.

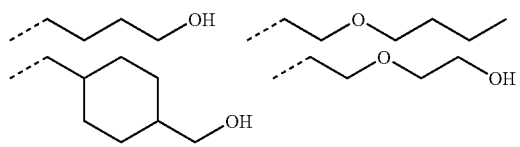

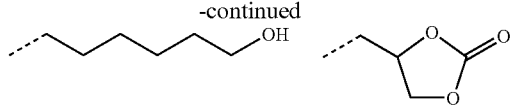

A pair of $R^{L01}$ and $R^{L02}$, $R^{L01}$ and $R^{L03}$, or $R^{L02}$ and $R^{L03}$ may form a ring with carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is a substituted or unsubstituted, straight, branched or cyclic alkyl group of 1 to 8 carbon atoms or a substituted or unsubstituted aryl group of 6 to 20 carbon atoms. Examples of the optionally substituted alkyl group include straight, branched or cyclic alkyl groups such as methyl, ethyl, propyl, isopropyl, n-butyl, sec-butyl, tert-butyl, tert-amyl, n-pentyl, n-hexyl, cyclopentyl, and cyclohexyl, and substituted forms of such groups in which some hydrogen atoms are substituted by hydroxyl, alkoxy, carboxy, alkoxycarbonyl, oxo, amino, alkylamino, cyano, mercapto, alkylthio, sulfo or other groups. Examples of the optionally substituted aryl groups include phenyl, methylphenyl, naphthyl, anthryl, phenanthryl, and pyrenyl. Letter m is equal to 0 or 1, n is equal to 0, 1, 2 or 3, and 2m+n is equal to 2 or 3.

In formula (L4), $R^{L06}$ is a substituted or unsubstituted, straight, branched or cyclic alkyl group of 1 to 8 carbon atoms or a substituted or unsubstituted aryl group of 6 to 20 carbon atoms. Examples of these groups are the same as exemplified for $R^{L05}$. $R^{L07}$ to $R^{L16}$ independently represent hydrogen or monovalent hydrocarbon groups of 1 to 15 carbon atoms. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

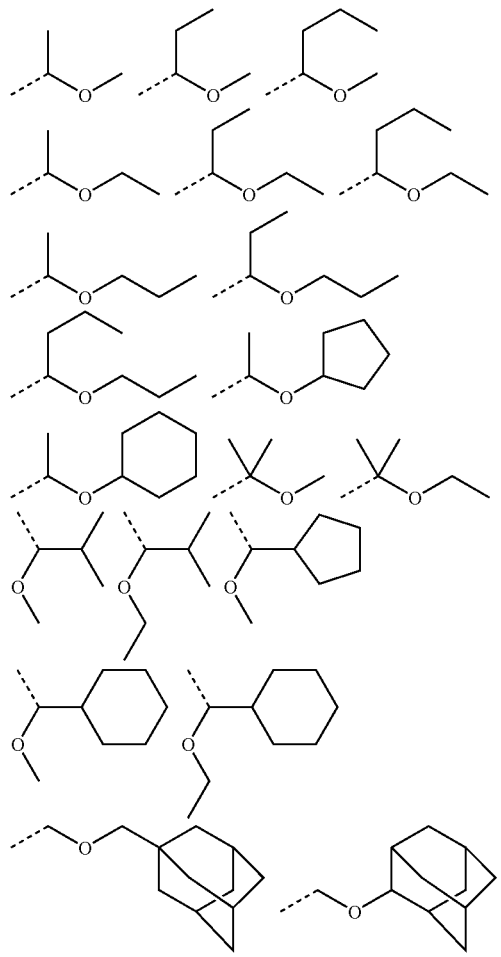

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

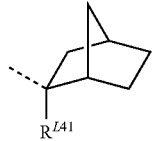
(L4-1)

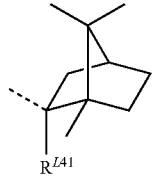
(L4-2)

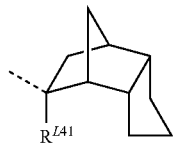
(L4-3)

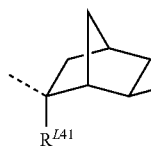
(L4-4)

In formulas (L4-1) to (L4-4), the broken line denotes a bonding site and direction. $R^{L41}$ is each independently a monovalent hydrocarbon group, typically a straight, branched or cyclic alkyl group of 1 to 10 carbon atoms, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

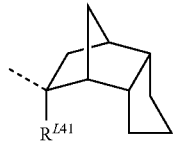
(L4-3-1)

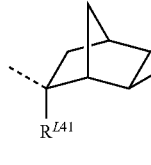
(L4-3-2)

Similarly, the general formula (L4-4) represents one or a mixture of two or more selected from groups having the following general formulas (L4-4-1) to (L4-4-4).

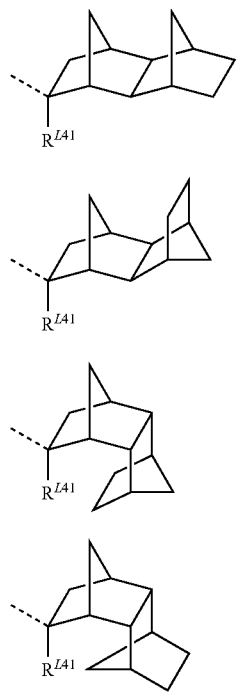

(L4-4-1)

(L4-4-2)

(L4-4-3)

(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50% is preferred, with an exo proportion of at least 80% being more preferred.

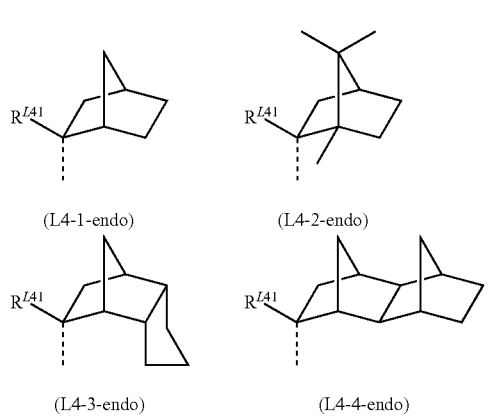

(L4-1-endo)   (L4-2-endo)

(L4-3-endo)   (L4-4-endo)

See JP-A 2000-336121.

Illustrative examples of the acid labile group of formula (L4) are given below

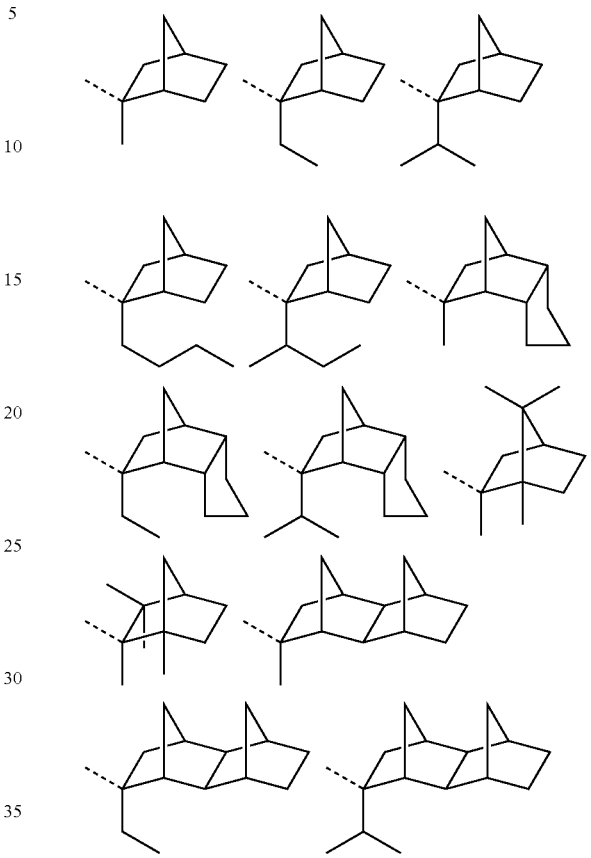

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{L04}$.

Illustrative examples of the recurring units of formula (3) are given below, but not limited thereto.

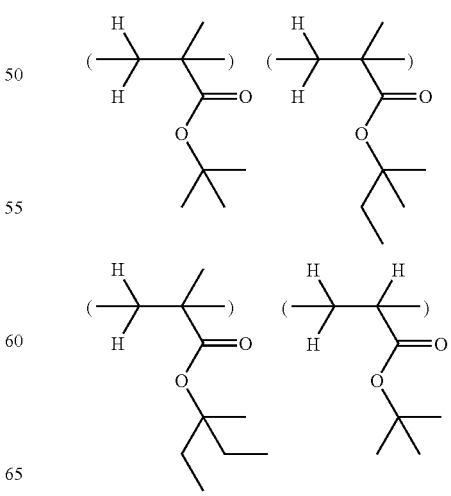

-continued
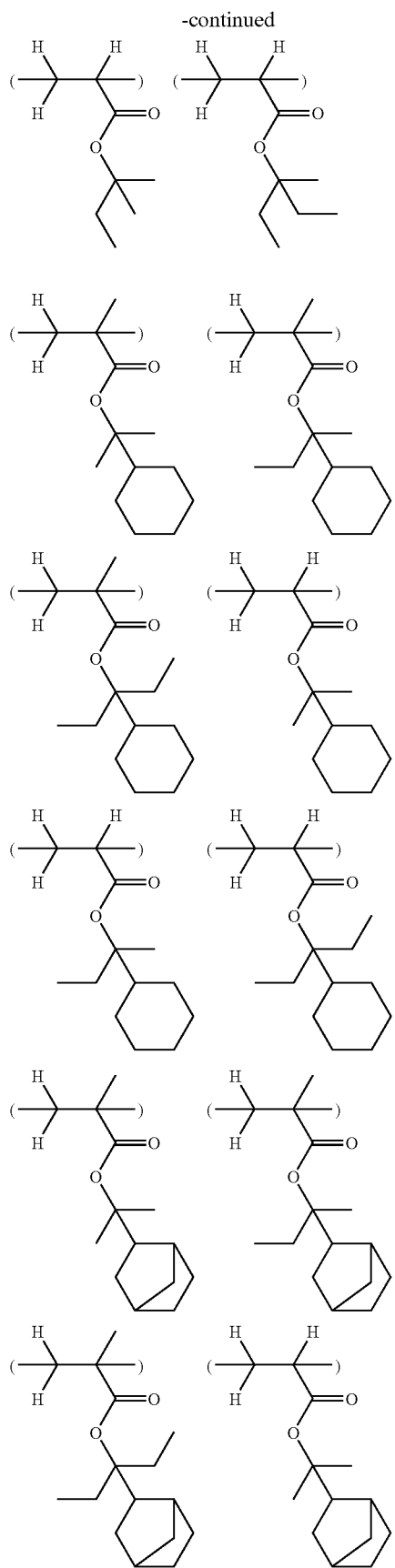
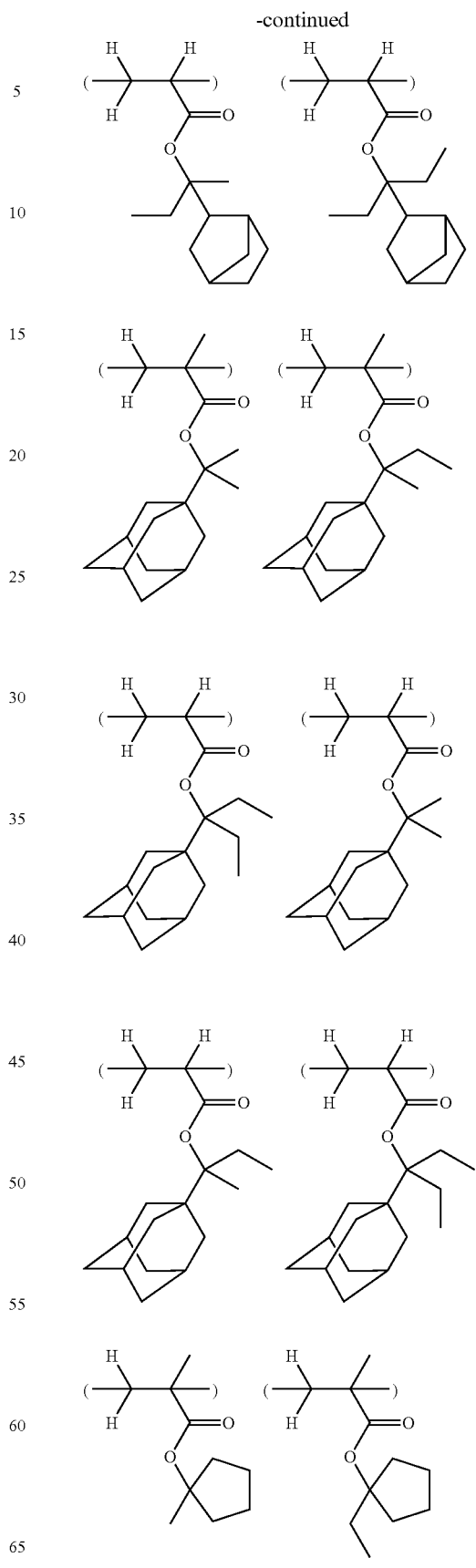

-continued
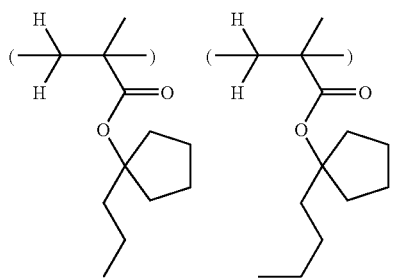
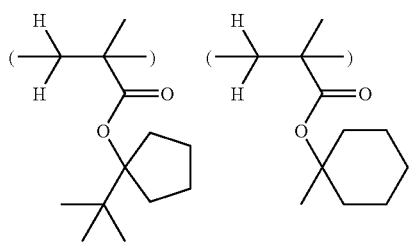
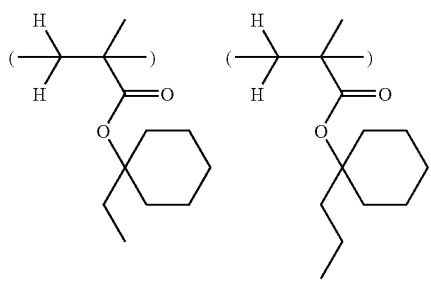
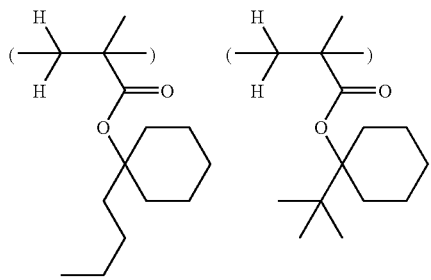
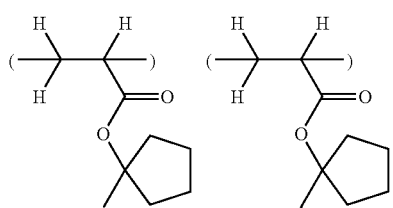
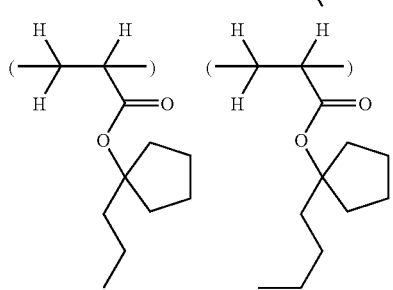
-continued
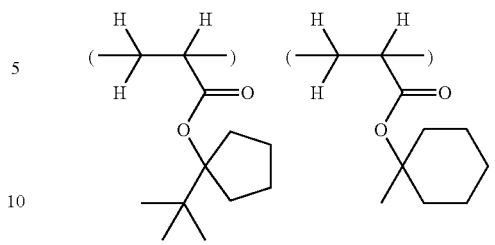
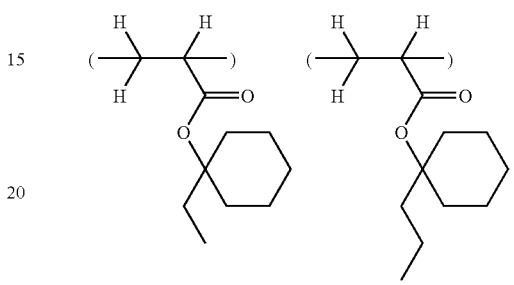
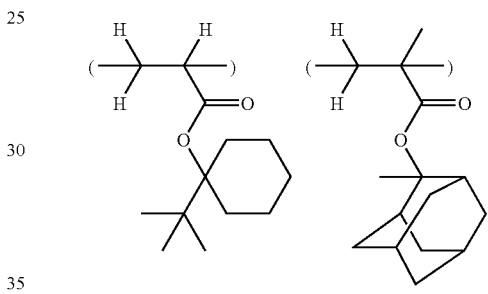
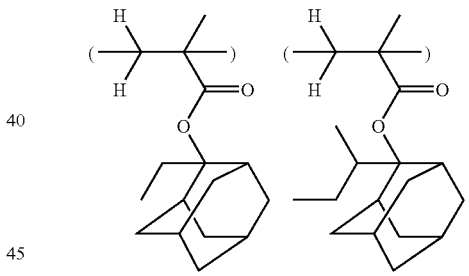
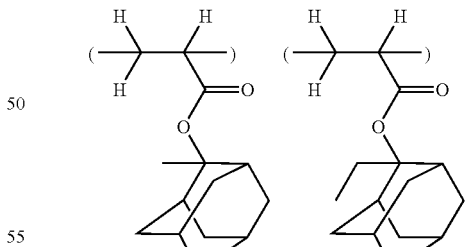
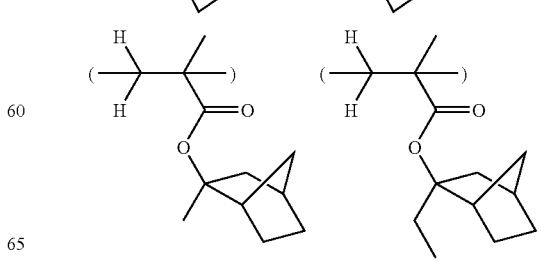

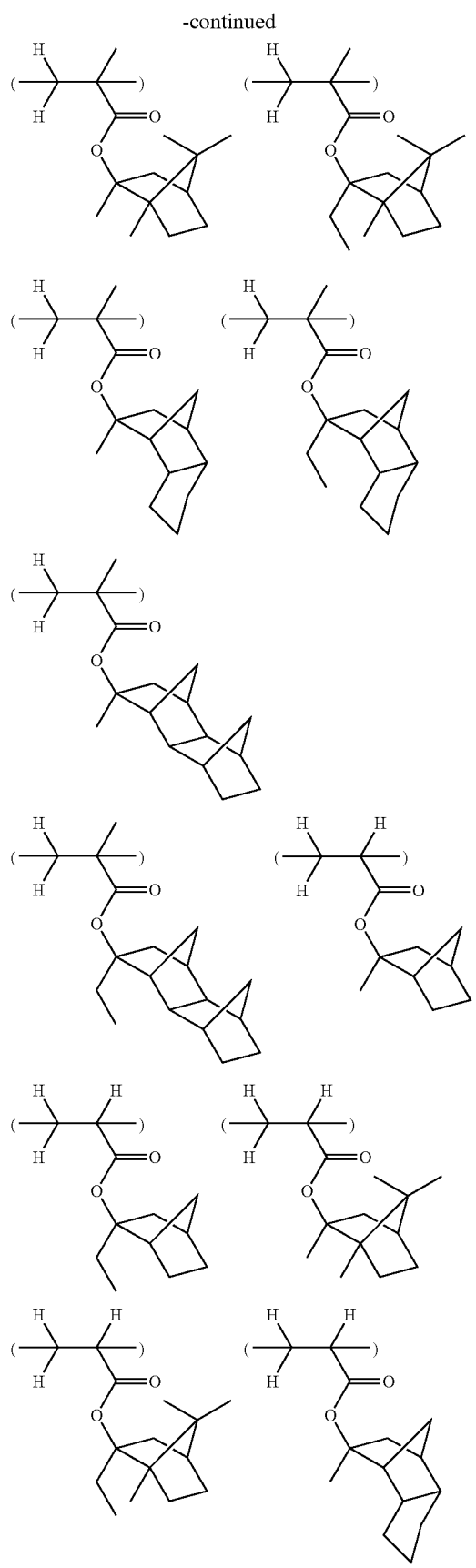
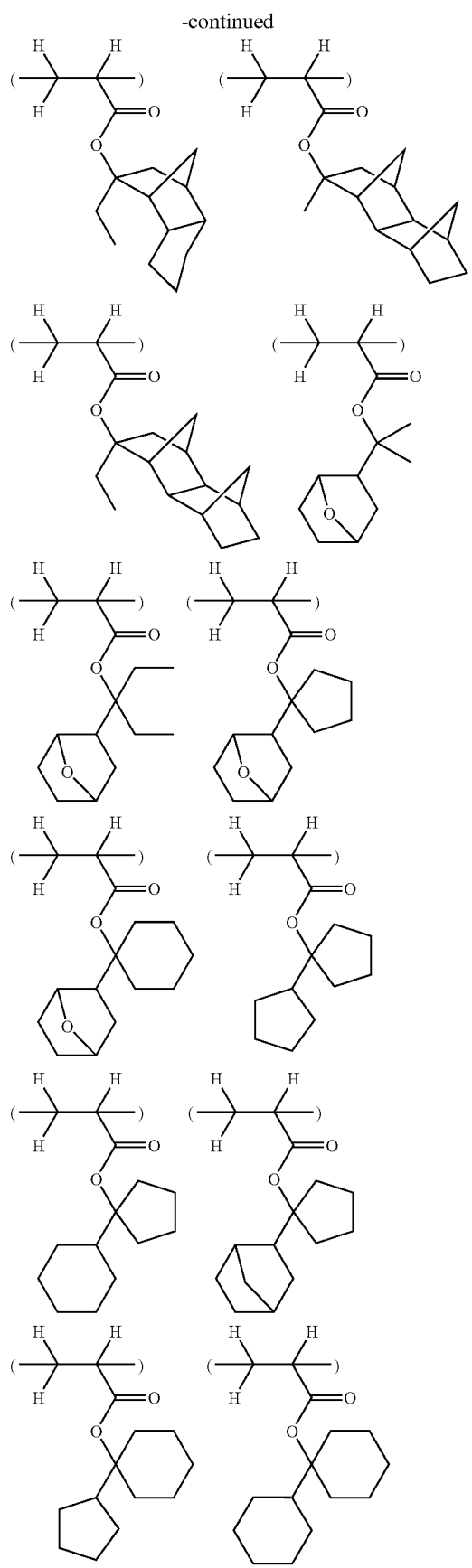

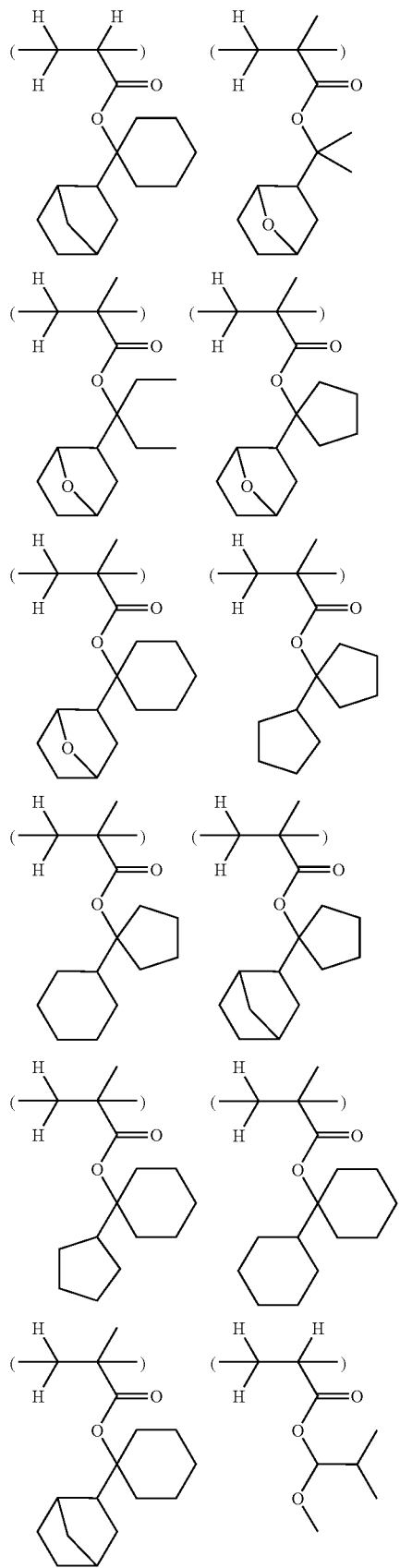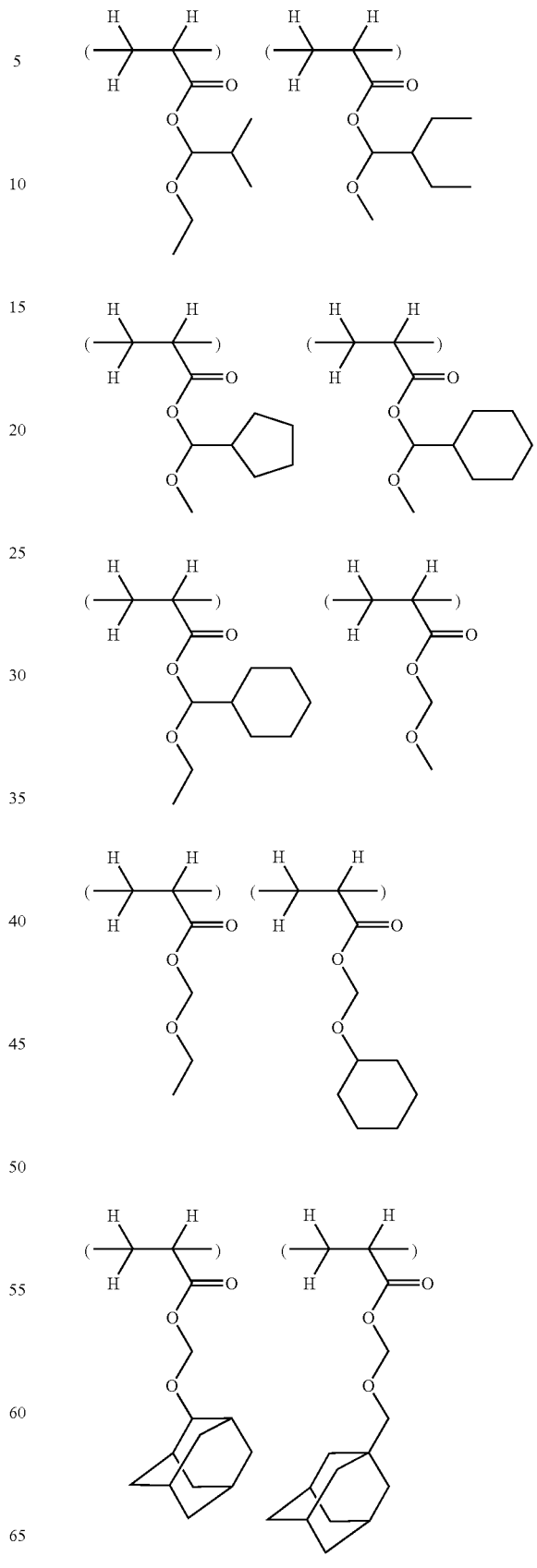

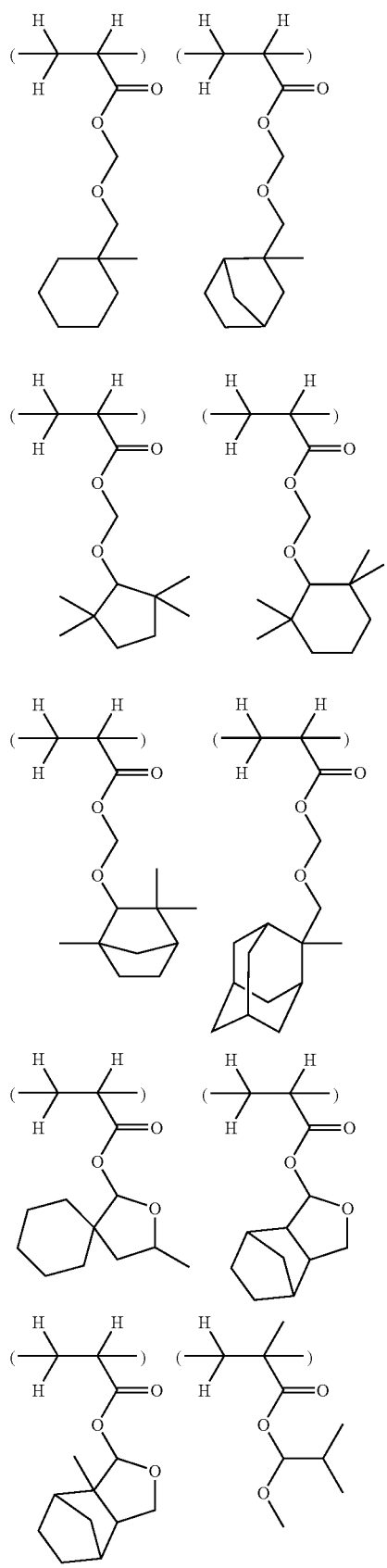
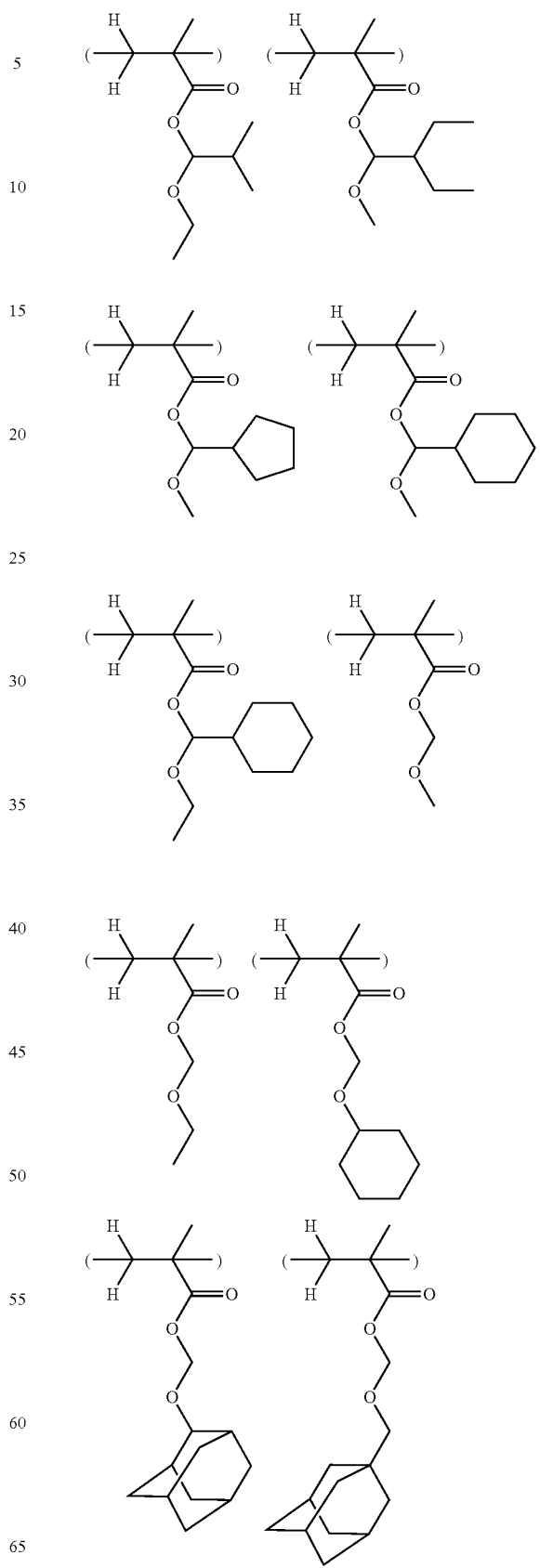

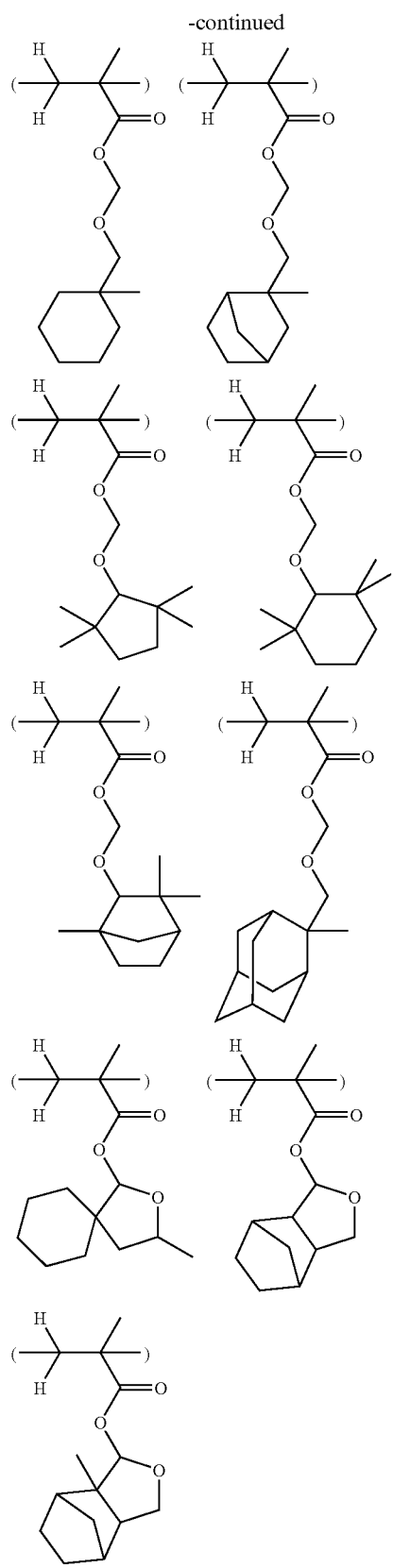
Illustrative examples of the recurring units of formula (4) are given below, but not limited thereto.
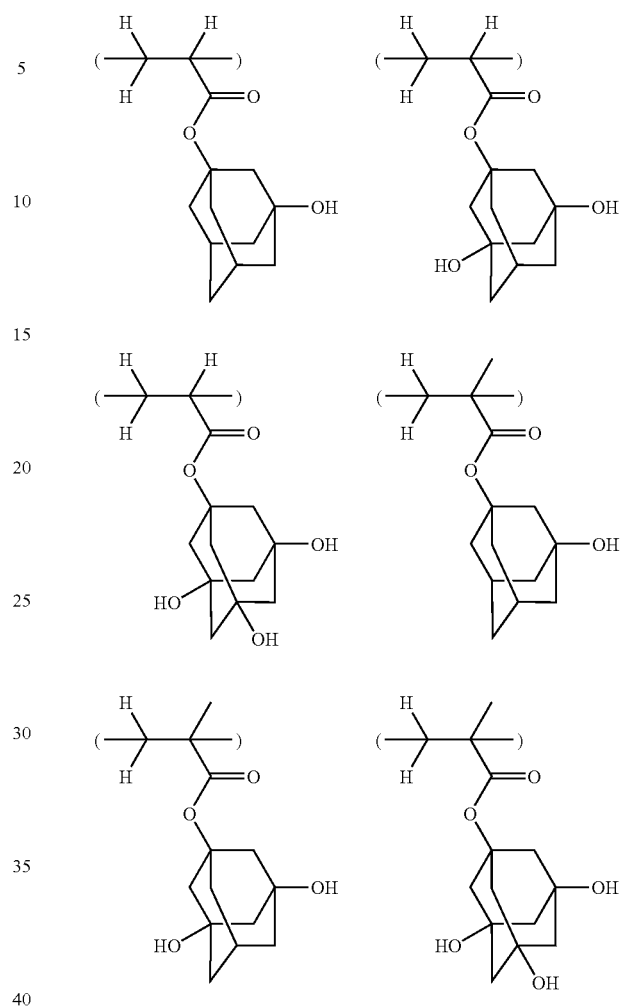
Illustrative examples of the recurring units of formula (5) are given below, but not limited thereto.
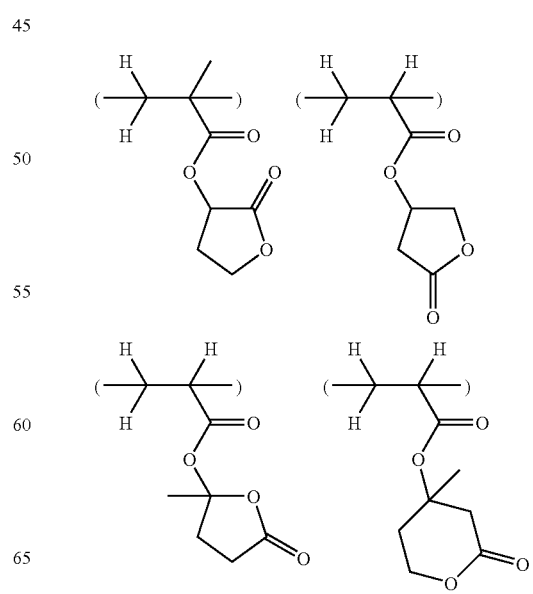

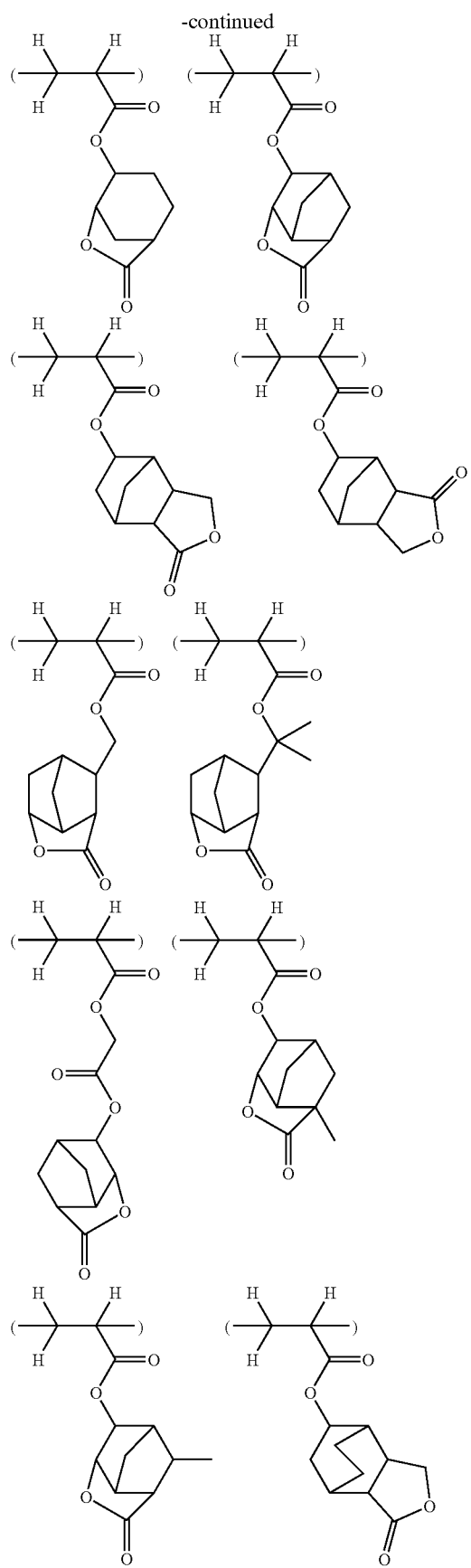
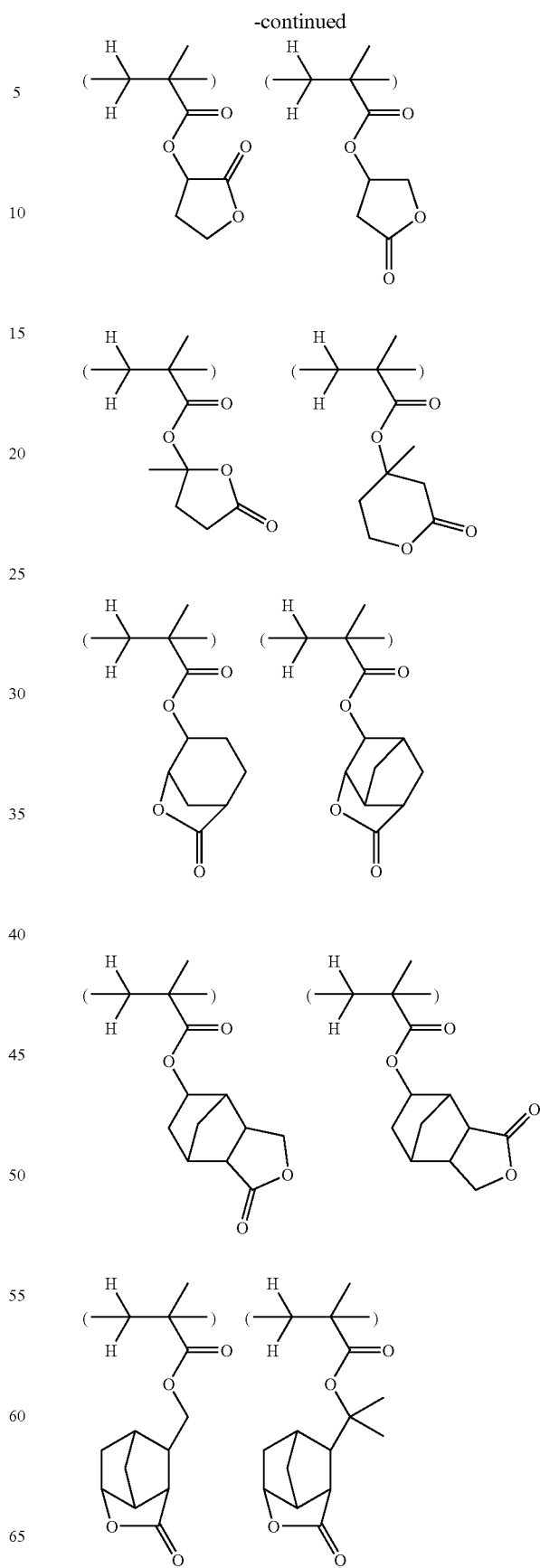

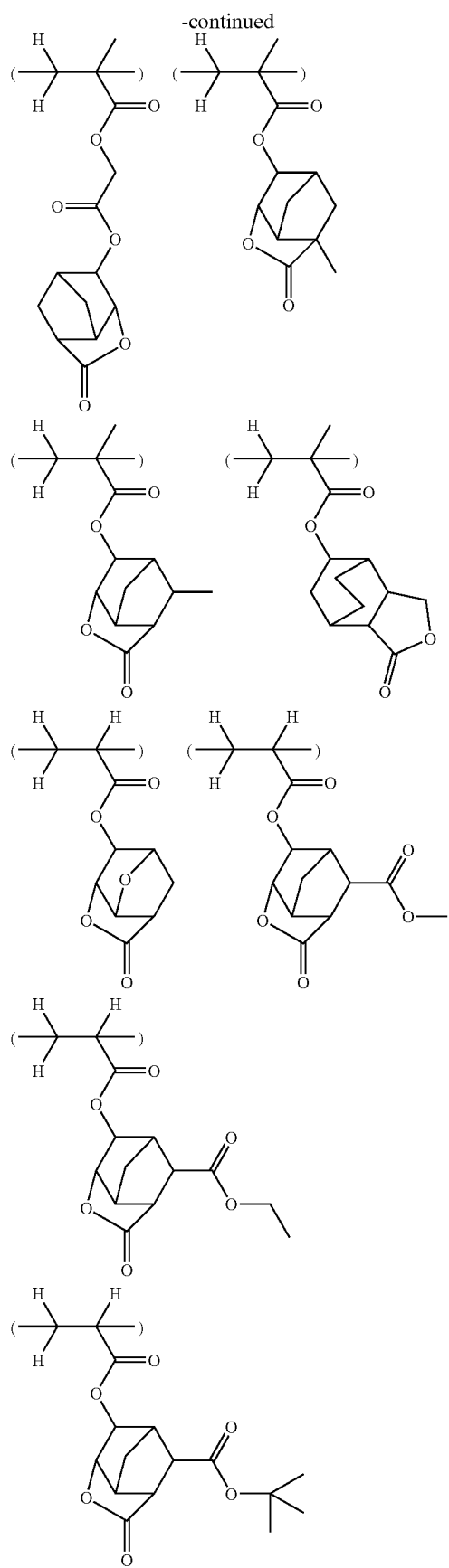
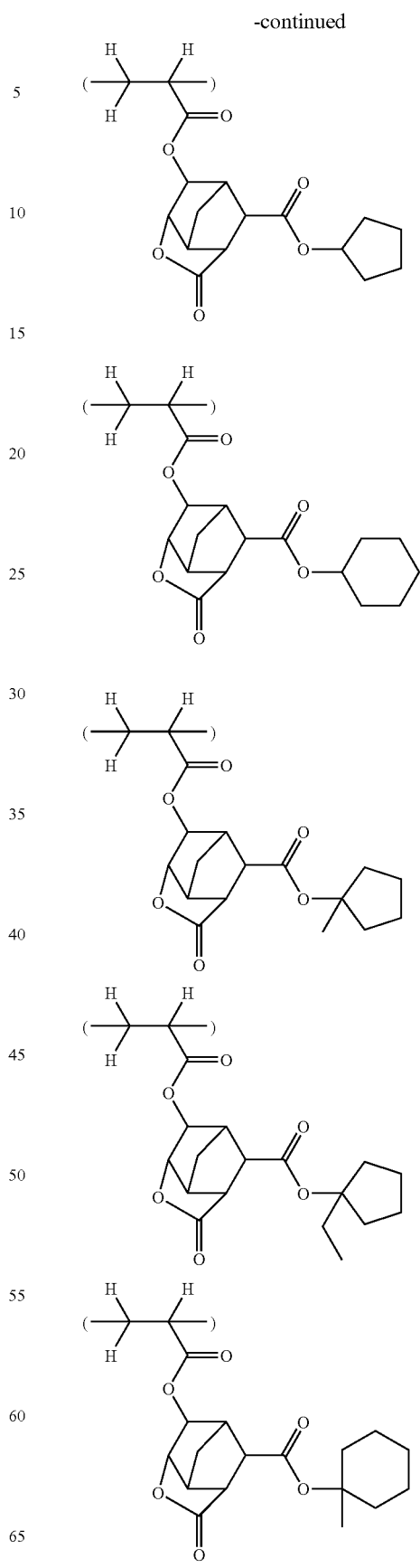

-continued
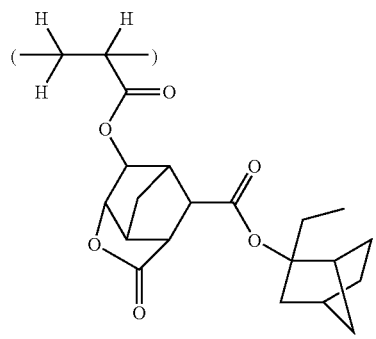
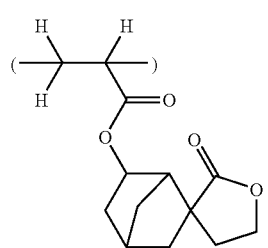
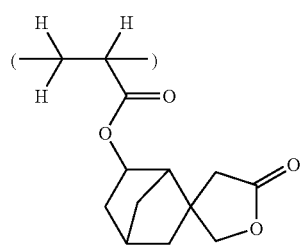
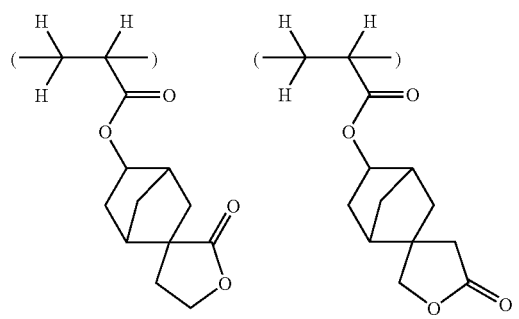
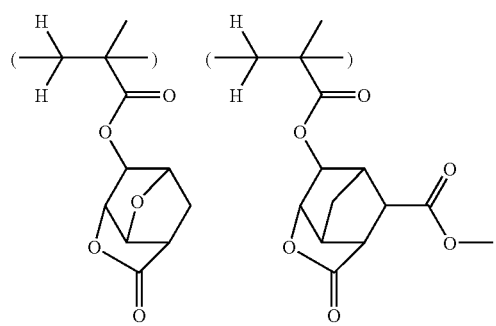
-continued
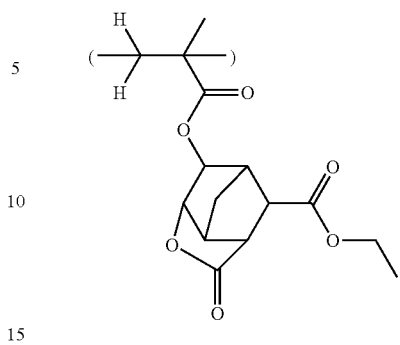
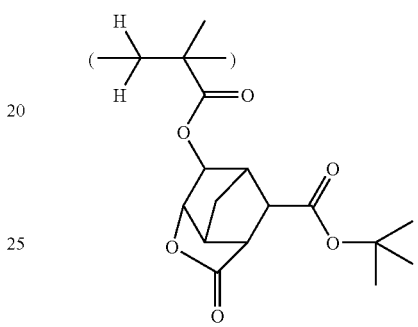
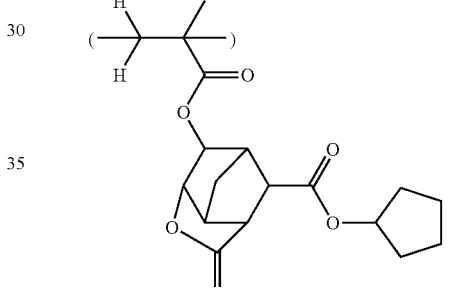
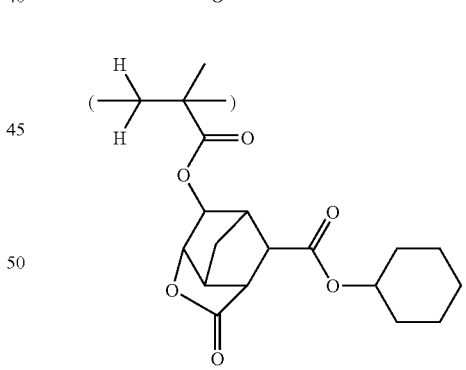
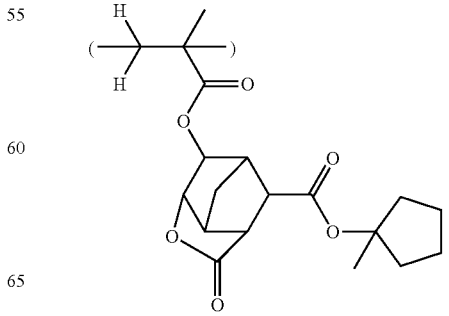

-continued
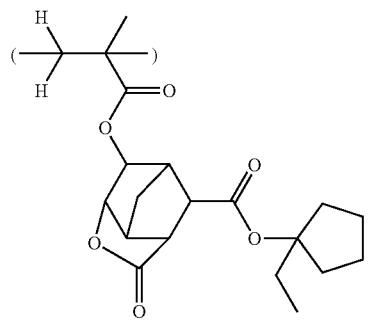
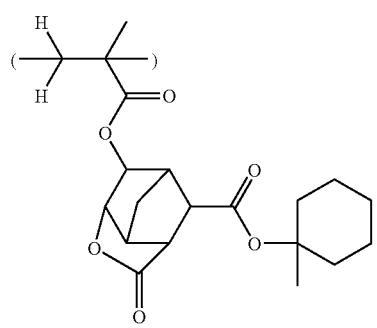
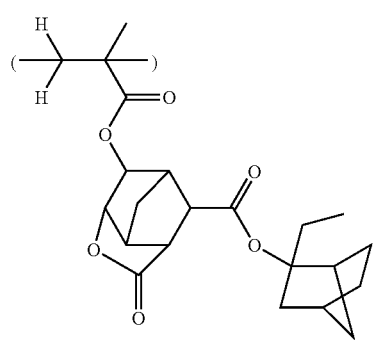
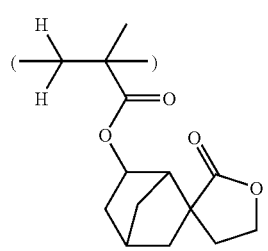
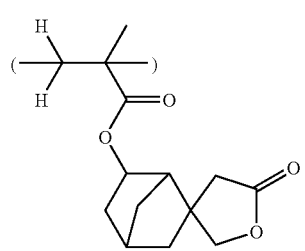
-continued
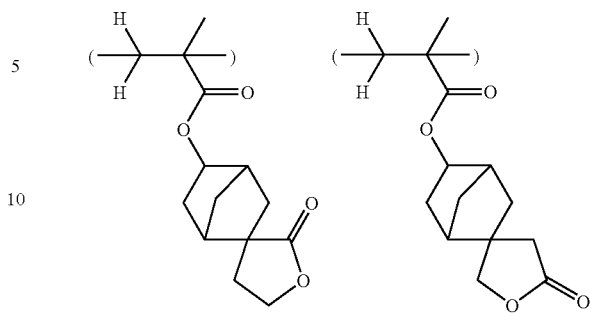
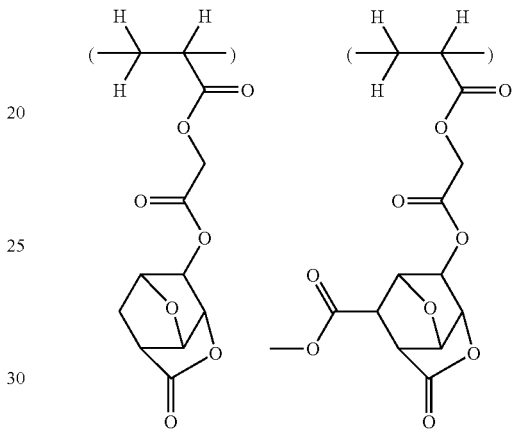
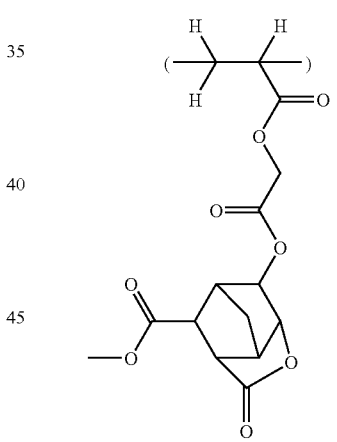
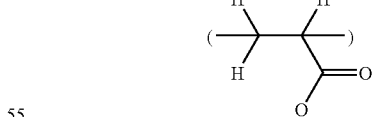
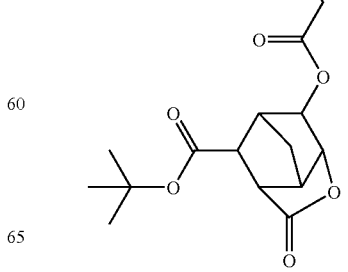

-continued
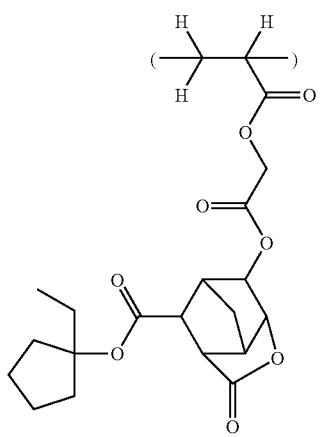
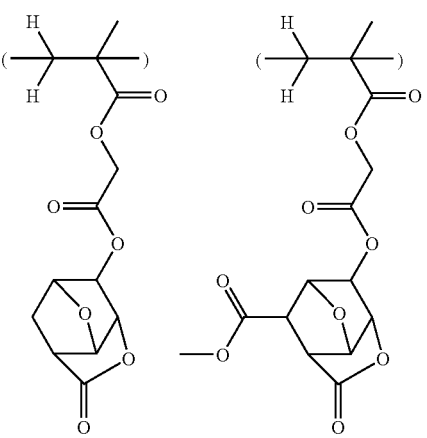

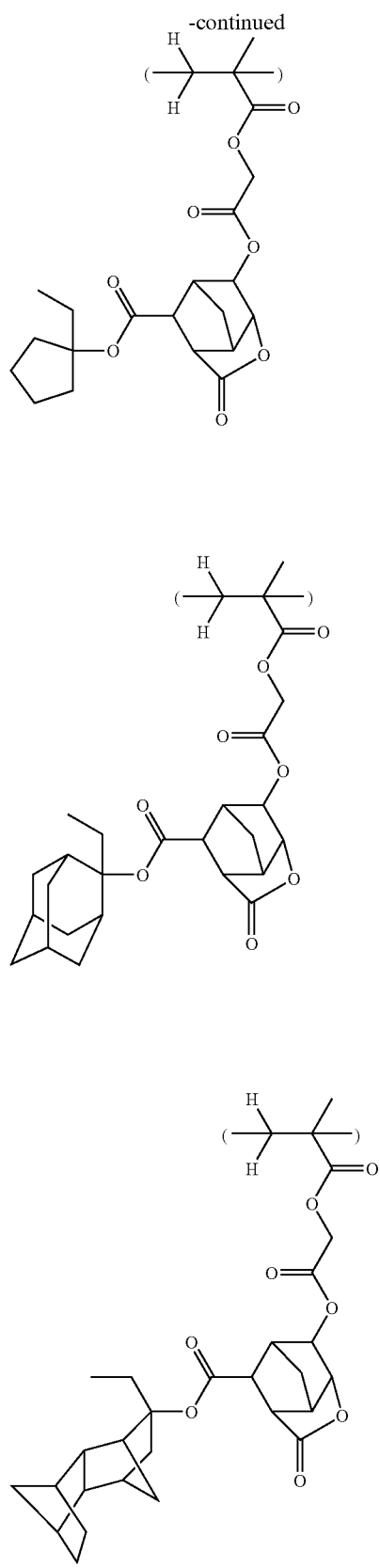
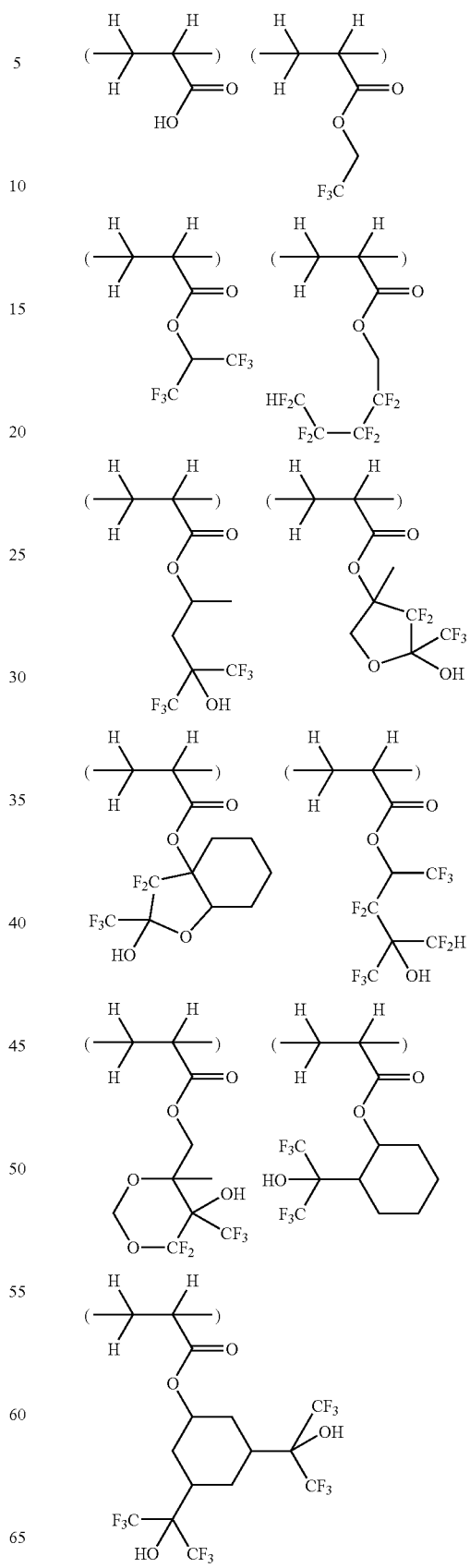
Illustrative examples of the recurring units of formula (6) are given below, but not limited thereto.

-continued
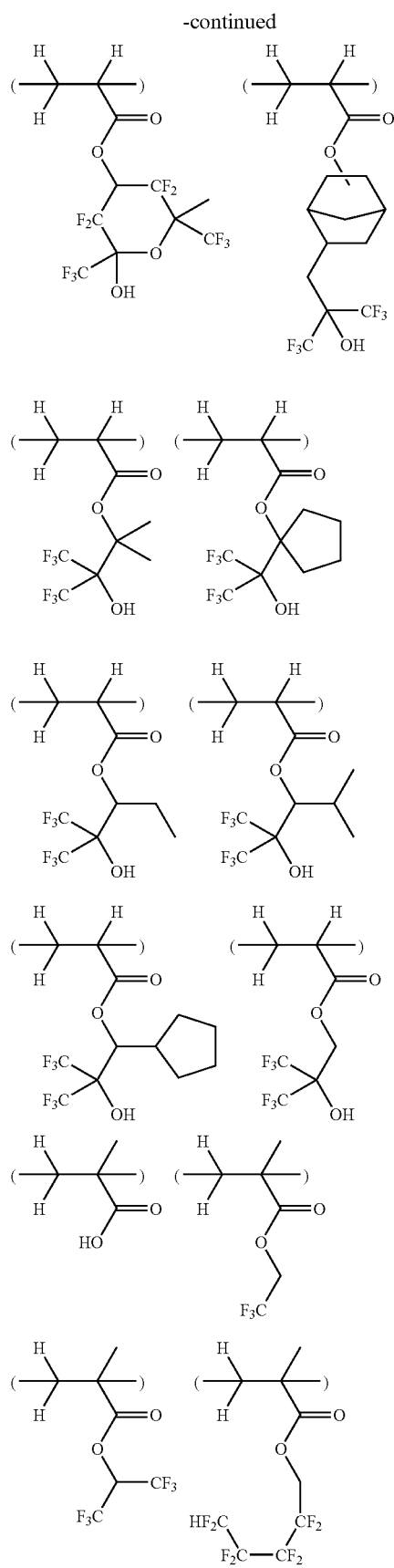
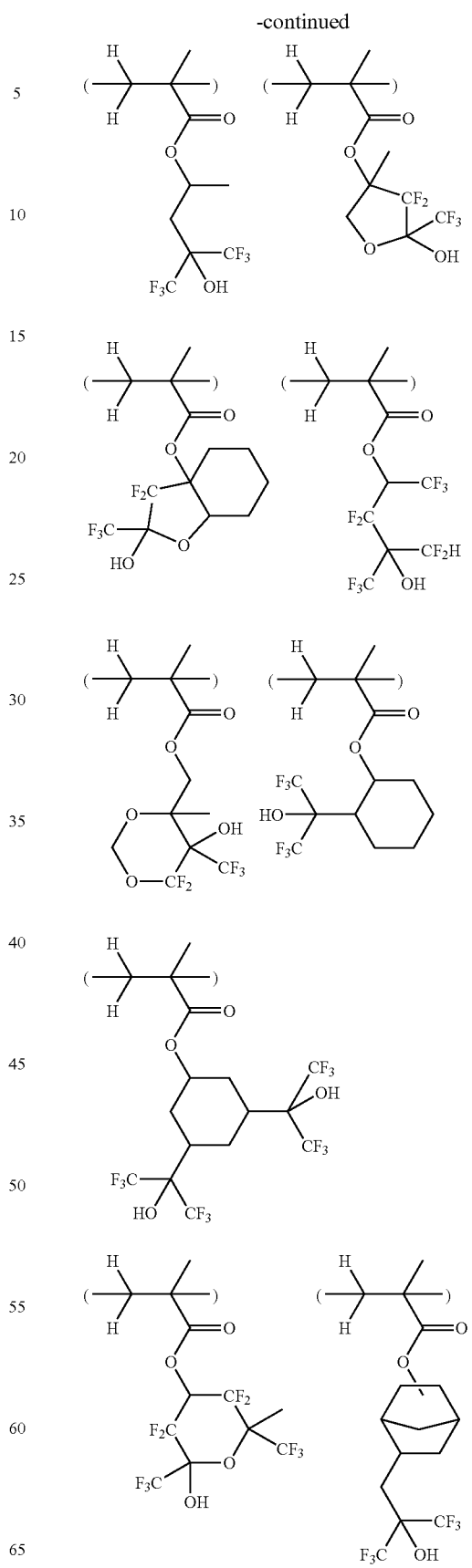

-continued

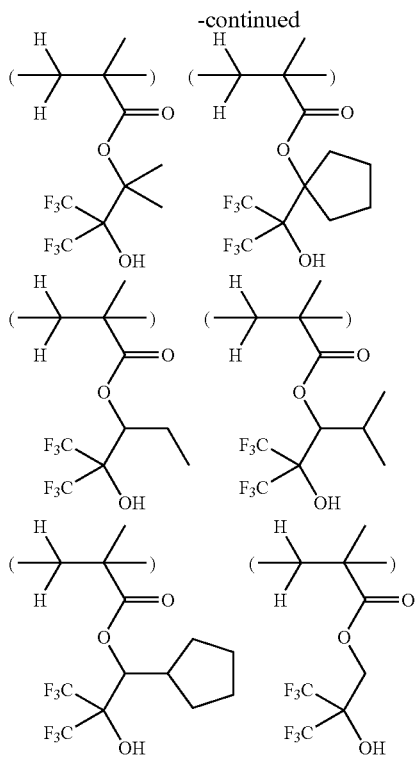

In addition to the foregoing units, the polymers of the invention may further comprise recurring units derived from carbon-to-carbon double bond-bearing monomers other than the above-described ones, for example, substituted acrylic acid esters such as methyl methacrylate, methyl chrotonate, dimethyl maleate and dimethyl itaconate, unsaturated carboxylic acids such as maleic acid, fumaric acid, and itaconic acid, cyclic olefins such as norbornene, norbornene derivatives, and tetracyclo[4.4.0.1$^{2,5}$.1$^{7,10}$]dodecene derivatives, unsaturated acid anhydrides such as itaconic anhydride, and other monomers.

The polymers of the invention generally have a weight average molecular weight (Mw) of 1,000 to 500,000, and preferably 3,000 to 100,000, as measured by gel permeation chromatography (GPC) using polystyrene standards. Outside the range, there may result an extreme drop of etch resistance, and a drop of resolution due to difficulty to gain a dissolution rate difference before and after exposure.

In the inventive polymers, appropriate proportions of the respective recurring units derived from the monomers are given below although the invention is not limited thereto. The inventive polymers may contain:

(I) constituent units of one or more types having formula (2) derived from monomers of formula (1) in a proportion of more than 0 mol % to 100 mol %, preferably 5 to 70 mol %, and more preferably 10 to 50 mol %, (II) constituent units of one or more types having formulas (3) to (6) in a proportion of 0 mol % to less than 100 mol %, preferably 1 to 95 mol %, and more preferably 20 to 90 mol %, and (III) constituent units of one or more types derived from other monomers in a proportion of 0 to 80 mol %, preferably 0 to 70 mol %, and more preferably 0 to 50 mol %, based on the total moles of constituent units.

Of constituent units (II), recurring units of formula (3) are incorporated in a proportion of preferably 1 to 90 mol %, more preferably 10 to 70 mol %, recurring units of formula (4) in a proportion of preferably 0 to 60 mol %, more preferably 1 to 40 mol %, recurring units of formula (5) in a proportion of preferably 0 to 60 mol %, more preferably 0 to 40 mol %, and recurring units of formula (6) in a proportion of preferably 0 to 50 mol %, more preferably 0 to 40 mol %.

The polymers of the invention are prepared by copolymerization reaction using the compound of formula (1) as a first monomer and polymerizable double bond-bearing compounds as second and subsequent monomers. The copolymerization reaction to produce the inventive polymers may be performed in various modes, preferably radical polymerization, anionic polymerization or coordination polymerization. The first monomer (i.e., the compound of formula (1)) and the second and subsequent monomers which are used in copolymerization should preferably have a content of oligomers or polymers which is up to 10 mol %, more preferably up to 3 mol %, and even more preferably up to 1 mol %.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about ½ hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction conditions outside the described range may be employed if desired.

Resist Composition

Since the polymer of the invention is useful as the base resin of a resist composition, the other aspect of the invention provides a resist composition comprising the polymer and specifically a chemically amplified positive resist composition comprising the polymer. Typically, the resist composition contains (A) the inventive polymer as a base resin, (B) an acid generator, (C) an organic solvent, and optionally (D) a quencher and (E) a surfactant.

In addition to the inventive polymer, the base resin (A) may include another polymer having a dissolution rate in alkaline developer that increases under the action of acid, if necessary. Examples of the other polymer include, but are not limited to, (i) poly(meth)acrylic acid derivatives, (ii) norbornene derivative-maleic anhydride copolymers, (iii) hydrogenated products of ring-opening metathesis polymers (ROMP), and (iv) vinyl ether-maleic anhydride-(meth)acrylic acid derivative copolymers.

Of these, the hydrogenated products of ring-opening metathesis polymers are synthesized by the method illustrated in JP-A 2003-66612. Illustrative examples of such hydrogenated polymers include those polymers having the recurring units shown below, but are not limited thereto.

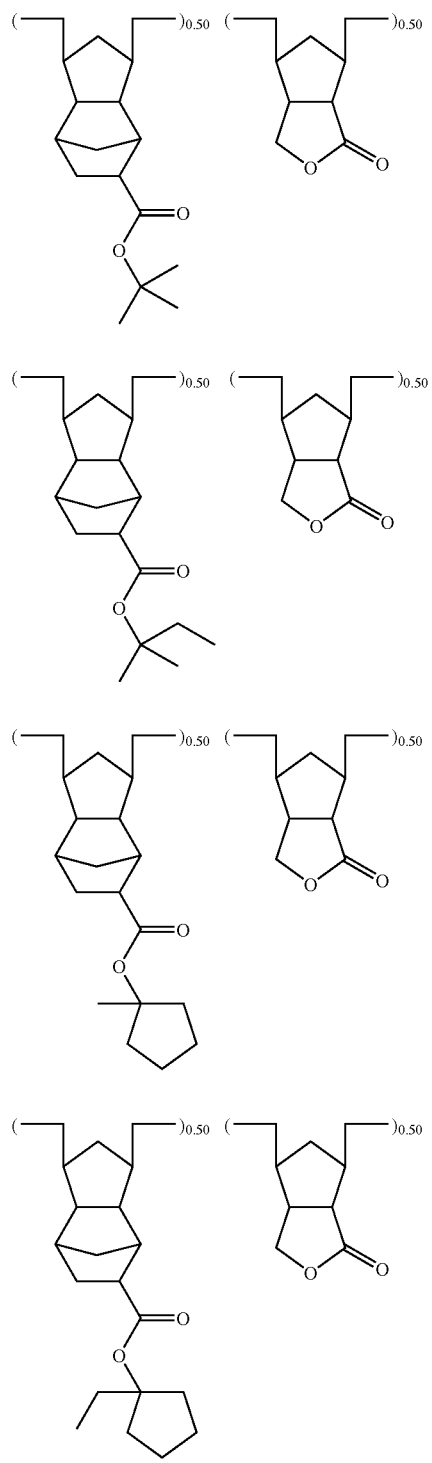

-continued

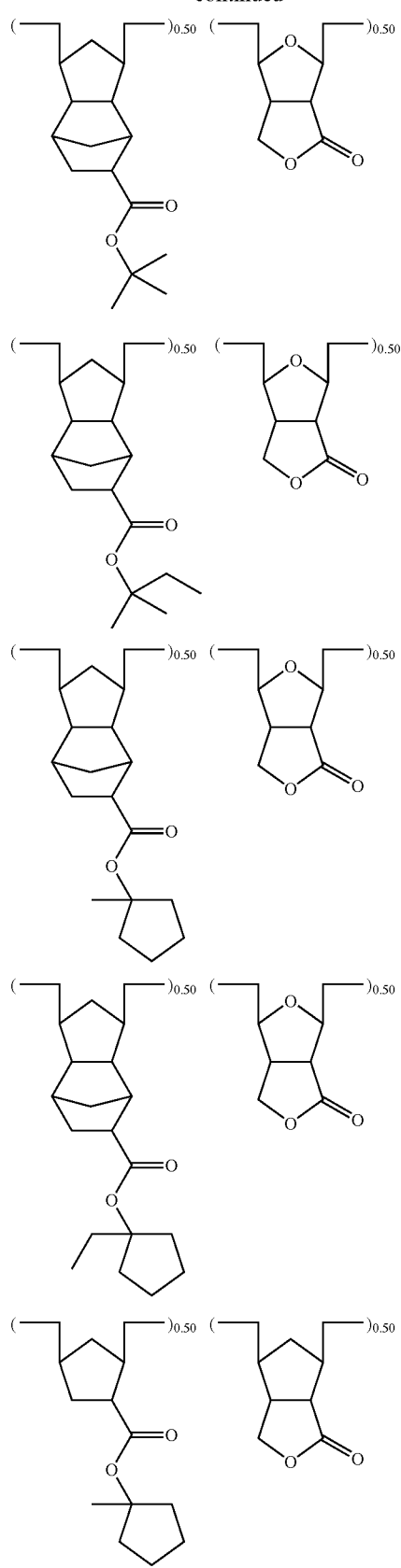

-continued
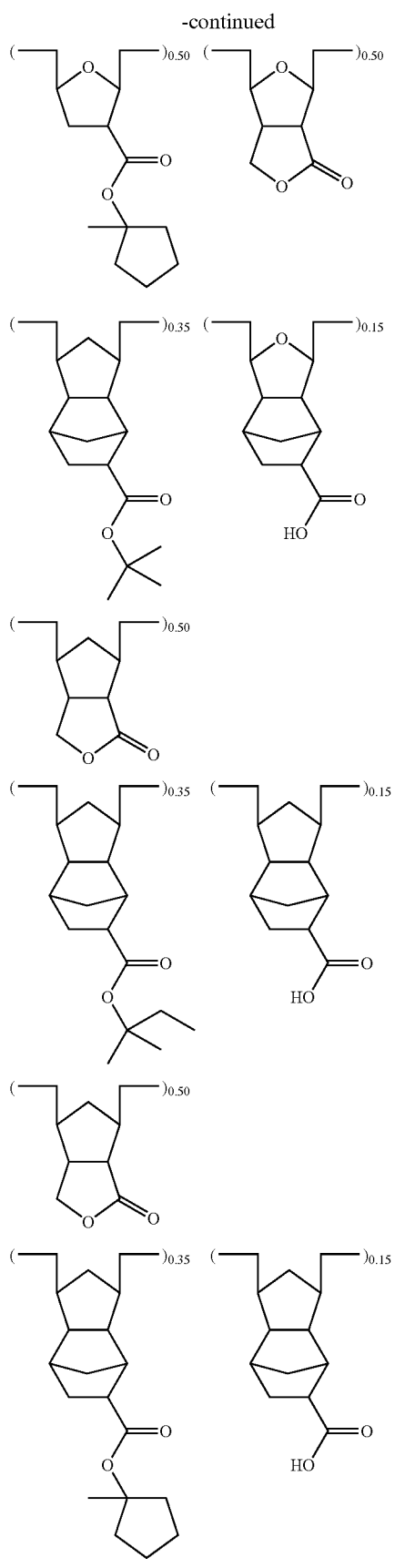
-continued
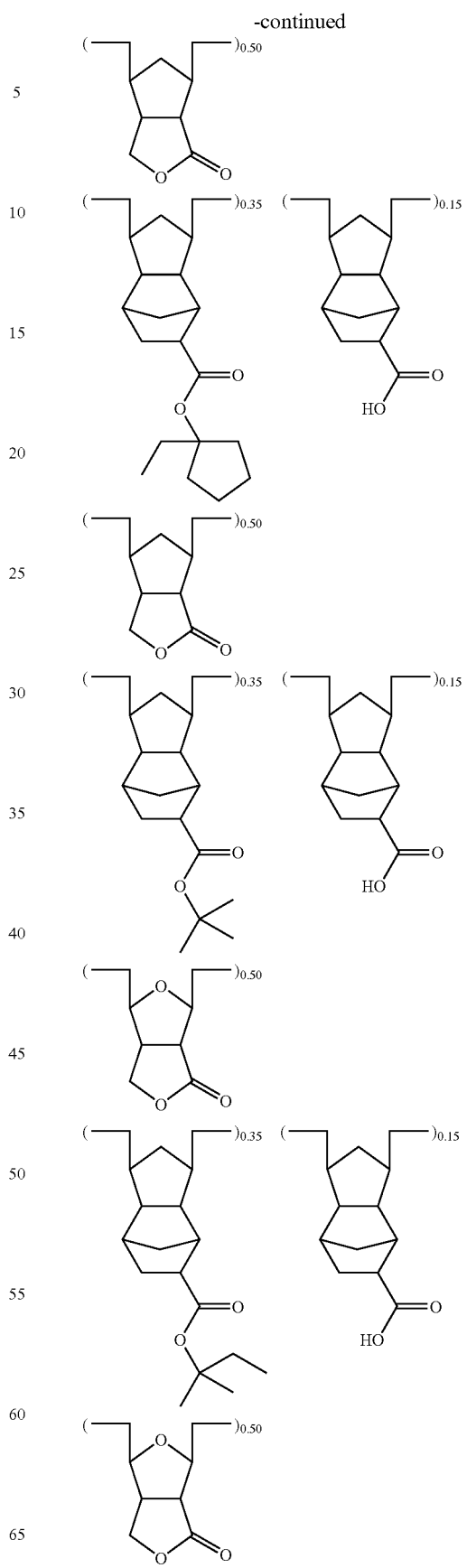

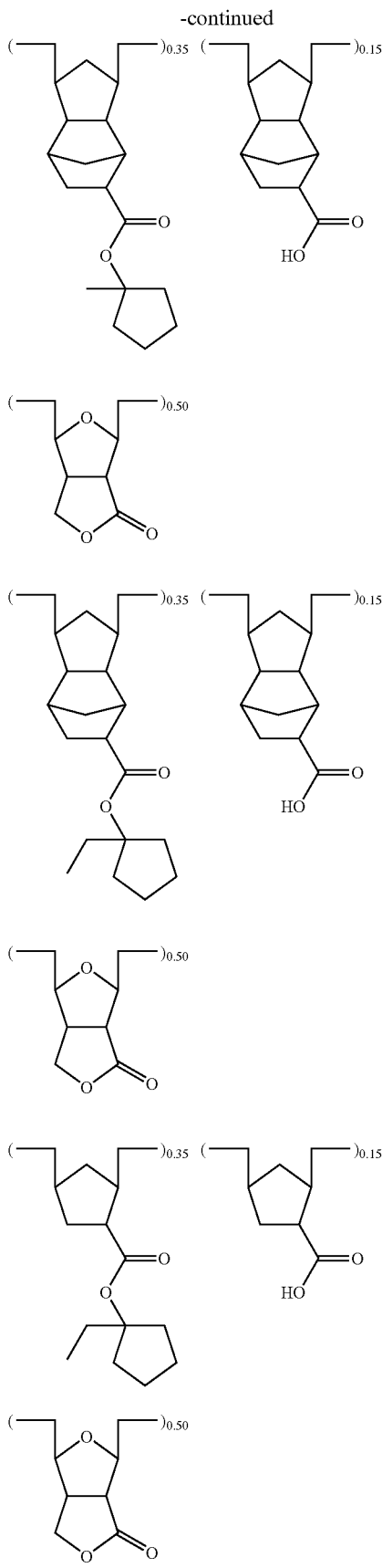

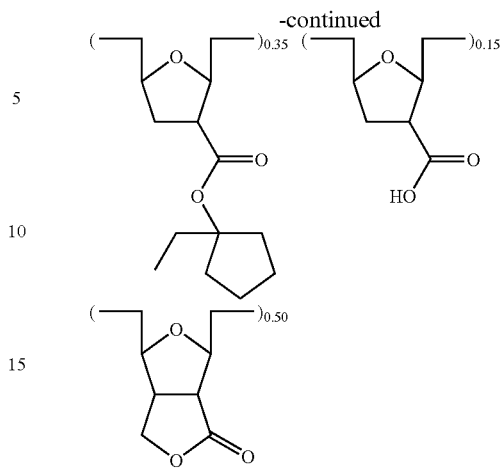

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The other polymer is not limited to one type and a mixture of two or more other polymers may be added. The use of plural polymers allows for easy adjustment of resist properties.

Photoacid Generator

As the acid generator (B), a photoacid generator is typically used. It is any compound capable of generating an acid upon exposure to high-energy radiation. Suitable photoacid generators include sulfonium salts, iodonium salts, sulfonyldiazomethane, N-sulfonyloxyimide, and oxime-O-sulfonate acid generators. Exemplary acid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenyldiphenylsulfonium, bis(4-methylphenyl)phenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium, 2-oxo-2-phenylethylthiacyclopentanium, 4-n-butoxynaphthyl-1-thiacyclopentanium, and 2-n-butoxynaphthyl-1-thiacyclopentanium.

Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris(substituted alkylsulfonyl)methide is tris(trifluoromethylsulfonyl)methide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris(substituted alkylsulfonyl)methide is tris(trifluoromethylsulfonyl)methide. Iodonium salts based on combination of the foregoing examples are included.

Exemplary sulfonyldiazomethane compounds include bis-sulfonyldiazomethane compounds and sulfonyl-carbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(4-acetyloxyphenylsulfonyl)diazomethane, bis(4-(methanesulfonyloxy)phenylsulfonyl)diazomethane, bis(4-(p-toluenesulfonyloxy)phenylsulfonyl)diazomethane, bis(4-n-hexyloxyphenylsulfonyl)diazomethane, bis(2-methyl-4-n-hexyloxyphenylsulfonyl)diazomethane, bis(2,5-dimethyl-4-n-hexyloxyphenylsulfonyl)diazomethane, bis(3,5-dimethyl-4-n-hexyloxyphenylsulfonyl)diazomethane, bis(2-methyl-5-isopropyl-4-n-hexyloxyphenylsulfonyl)-diazomethane, bis(2-naphthylsulfonyl)diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxydicarboxyimide photoacid generators include combinations of imide skeletons with sulfonates. Exemplary imide skeletons are succinimide, naphthalenedicarboxyimide, phthalimide, cyclohexyldicarboxyimide, 5-norbornene-2,3-dicarboxyimide, and 7-oxabicyclo[2.2.1]-5-heptene-2,3-dicarboxyimide. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropane-sulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Benzoinsulfonate photoacid generators include benzoin tosylate, benzoin mesylate, and benzoin butanesulfonate.

Pyrogallol trisulfonate photoacid generators include pyrogallol, phloroglucin, catechol, resorcinol, hydroquinone, in which all the hydroxyl groups are substituted by trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropane-sulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, 4-oxo-1-adamantyloxycarbonyldifluoromethanesulfonate, etc.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropane-sulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, 4-oxo-1-adamantyloxycarbonyldifluoromethanesulfonate, etc. Also useful are nitrobenzyl sulfonate analogues in which the nitro group on the benzyl side is substituted by a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Suitable O-arylsulfonyloxime compounds and O-alkylsulfonyloxime compounds (oxime sulfonates) include photoacid generators in the form of glyoxime derivatives; photoacid generators in the form of oxime sulfonates with a long conjugated system separated by thiophene or cyclohexadiene; oxime sulfonates having an electron withdrawing group such as trifluoromethyl incorporated for increased stability; oxime sulfonates using phenylacetonitrile or substituted acetonitrile derivatives; and bisoxime sulfonates.

Photoacid generators in the form of glyoxime derivatives include bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedionedioxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(methanesulfonyl)-α-dimethylglyoxime, bis-O-(trifluoromethanesulfonyl)-α-dimethylglyoxime, bis-O-(2,2,2-trifluoroethanesulfonyl)-α-dimethylglyoxime, bis-O-(10-camphorsulfonyl)-α-dimethylglyoxime, bis-O-(benzenesulfonyl)-α-dimethylglyoxime, bis-O-(4-fluorobenzenesulfonyl)-α-dimethylglyoxime, bis-O-(4-trifluoromethylbenzenesulfonyl)-α-dimethylglyoxime, bis-O-(xylenesulfonyl)-α-dimethylglyoxime, bis-O-(trifluoromethanesulfonyl)-nioxime, bis-O-(2,2,2-trifluoroethanesulfonyl)-nioxime, bis-O-(10-camphorsulfonyl)-nioxime, bis-O-(benzenesulfonyl)-nioxime, bis-O-(4-fluorobenzenesulfonyl)-nioxime, bis-O-(4-(trifluoromethyl)benzenesulfonyl)-nioxime, and bis-O-(xylenesulfonyl)-nioxime. Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Photoacid generators in the form of oxime sulfonates with a long conjugated system separated by thiophene or cyclohexadiene include (5-(p-toluenesulfonyl)oxyimino-5H-thiophen-2-ylidene)phenyl-acetonitrile, (5-(10-camphorsulfonyl)oxyimino-5H-thiophen-2-ylidene)phenyl-acetonitrile, (5-n-octanesulfonyloxyimino-5H-thiophen-2-ylidene)phenyl-acetonitrile, (5-(p-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, (5-n-octanesulfonyloxyimino-5H-thiophen-2-ylidene)(2-methylphenyl)acetonitrile, (5-(4-(p-toluenesulfonyloxy)benzenesulfonyl)oxyimino-5H-thiophen-2-ylidene)phenylacetonitrile, and (5-(2,5-bis(p-toluenesulfonyloxy)benzenesulfonyl)oxyimino-5H-thiophen-2-ylidene)phenylacetonitrile. Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Suitable oxime sulfonates having an electron withdrawing group such as trifluoromethyl incorporated for increased stability include 2,2,2-trifluoro-1-phenyl-ethanone O-(methylsulfonyl)oxime, 2,2,2-trifluoro-1-phenyl-ethanone O-(10-camphorsulfonyl)oxime, 2,2,2-trifluoro-1-phenylethanone O-(4-methoxybenzenesulfonyl)-oxime, 2,2,2-trifluoro-1-phenylethanone O-(1-naphthylsulfonyl)oxime, 2,2,2-trifluoro-1-phenylethanone O-(2-naphthylsulfonyl)oxime, 2,2,2-trifluoro-1-phenylethanone O-(2,4,6-trimethylphenylsulfonyl)oxime, 2,2,2-trifluoro-1-(4-methylphenyl)ethanone O-(10-camphor-sulfonyl)oxime, 2,2,2-trifluoro-1-(4-methylphenyl)ethanone O-(methylsulfonyl)-oxime, 2,2,2-trifluoro-1-(2-methylphenyl)ethanone O-(10-camphor-sulfonyl)oxime, 2,2,2-trifluoro-1-(2,4-dimethylphenyl)ethanone O-(10-camphor-sulfonyl)oxime, 2,2,2-trifluoro-1-(2,4-dimethylphenyl)ethanone O-(1-naphthyl-sulfonyl)oxime, 2,2,2-trifluoro-1-(2,4-dimethylphenyl)-ethanone O-(2-naphthylsulfonyl)oxime, 2,2,2-trifluoro-1-(2,4,6-trimethylphenyl)ethanone O-(10-camphorsulfonyl)oxime, 2,2,2-trifluoro-1-(2,4,6-trimethylphenyl)ethanone O-(1-naphthylsulfonyl)oxime, 2,2,2-trifluoro-1-(2,4,6-trimethylphenyl)ethanone O-(2-naphthylsulfonyl)oxime, 2,2,2-trifluoro-1-(4-methoxyphenyl)ethanone O-(methyl-sulfonyl)oxime, 2,2,2-trifluoro-1-(4-methylthiophenyl)-ethanone O-(methyl-sulfonyl)oxime, 2,2,2-trifluoro-1-(3,4-dimethoxyphenyl)ethanone O-(methyl-sulfonyl)oxime, 2,2,2-trifluoro-1-(4-methoxyphenyl)ethanone O-(4-methyl-phenylsulfonyl)oxime, 2,2,2-trifluoro-1-(4-methoxyphenyl)ethanone O-(4-methoxy-phenylsulfonyl)oxime, 2,2,2-trifluoro-1-(4-methoxyphenyl)ethanone O-(4-dodecyl-phenylsulfonyl)oxime, 2,2,2-trifluoro-1-(4-methoxyphenyl)ethanone O-(octylsulfonyl)-oxime, 2,2,2-trifluoro-1-(4-thiomethylphenyl)ethanone O-(4-methoxy-phenylsulfonyl)oxime, 2,2,2-trifluoro-1-(4-thiomethylphenyl)ethanone O-(4-dodecyl-phenylsulfonyl)oxime, 2,2,2-trifluoro-1-(4-thiomethylphenyl)ethanone O-(octyl-sulfonyl)oxime, 2,2,2-trifluoro-1-(4-thiomethylphenyl)ethanone O-(2-naphthyl-sulfonyl)oxime, 2,2,2-trifluoro-1-(2-methylphenyl)ethanone O-(methylsulfonyl)-oxime, 2,2,2-trifluoro-1-(4-methylphenyl)ethanone O-(phenylsulfonyl)-oxime, 2,2,2-trifluoro-1-(4-chlorophenyl)ethanone O-(phenylsulfonyl)-oxime, 2,2,3,3,4,4,4-heptafluoro-1-phenylbutanone O-(10-camphor-sulfonyl)oxime, 2,2,2-trifluoro-1-(1-naphthyl)ethanone O-(methylsulfonyl)-oxime, 2,2,2-trifluoro-1-(2-naphthyl)ethanone O-(methylsulfonyl)-oxime, 2,2,2-trifluoro-1-(4-benzylphenyl)ethanone O-(methylsulfonyl)-oxime, 2,2,2-trifluoro-1-(4-(phenyl-1,4-dioxa-but-1-yl)phenyl)-ethanone O-(methylsulfonyl)oxime, 2,2,2-trifluoro-1-(1-naphthyl) ethanone O-(propylsulfonyl)-oxime, 2,2,2-trifluoro-1-(2-naphthyl)ethanone O-(propylsulfonyl)-oxime, 2,2,2-trifluoro-1-(4-benzylphenyl)ethanone O-(propylsulfonyl)-oxime, 2,2,2-trifluoro-1-(4-methylsulfonylphenyl)ethanone O-(propyl-sulfonyl)oxime, 2,2,2-trifluoro-1-(4-methylsulfonyloxyphenyl)ethanone O-(propylsulfonyl)oxime, 2,2,2-trifluoro-1-(4-methylcarbonyloxyphenyl)ethanone O-(propylsulfonyl)oxime, 2,2,2-trifluoro-1-(6H,7H-5,8-dioxonaphth-2-yl)ethanone O-(propylsulfonyl)oxime, 2,2,2-trifluoro-1-(4-methoxycarbonylmethoxyphenyl)ethanone O-(propylsulfonyl)oxime, 2,2,2-trifluoro-1-(4-methoxycarbonyl)-(4-amino-1-oxa-pent-1-yl)phenyl)ethanone O-(propylsulfonyl)oxime, 2,2,2-trifluoro-1-(3,5-dimethyl-4-ethoxyphenyl)ethanone O-(propylsulfonyl)oxime, 2,2,2-trifluoro-1-(4-benzyloxyphenyl)ethanone O-(propyl-sulfonyl)oxime, 2,2,2-trifluoro-1-(2-thiophenyl)ethanone O-(propylsulfonate)-oxime, and 2,2,2-trifluoro-1-(1-dioxathiophen-2-yl) ethanone O-(propyl-sulfonate)oxime; 2,2,2-trifluoro-1-(4-(3-(4-(2,2,2-trifluoro-1-(trifluoro-methanesulfonyloxyimino)ethyl)phenoxy)propoxy)phenyl) ethanone O-(trifluoromethanesulfonyl)oxime, 2,2,2-trifluoro-1-(4-(3-(4-(2,2,2-trifluoro-1-(1-propane-sulfonyloxyimino)ethyl)phenoxy)propoxy)phenyl)ethanone O-(propylsulfonyl)oxime, 2,2,2-trifluoro-1-(4-(3-(4-(2,2,2-trifluoro-1-(1-butane-sulfonyloxyimino)ethyl)phenoxy)propoxy)phenyl)ethanone O-(butylsulfonyl)oxime, 2,2,2-trifluoro-1-(4-(3-(4-(2,2,2-trifluoro-1-(4-(4-methyl-phenylsulfonyloxy)phenylsulfonyloxyimino)ethyl) phenoxy)-propoxy)phenyl)ethanone O-(4-(4-methylphenylsulfonyloxy)-phenylsulfonyl)oxime, and 2,2,2-trifluoro-1-(4-(3-(4-(2,2,2-trifluoro-1-(2,5-bis(4-methylphenylsulfonyloxy)benzenesulfonyloxy) phenylsulfonyloxy-imino)ethyl)phenoxy)propoxy)phenyl) ethanone O-(2,5-bis(4-methylphenylsulfonyloxy) benzenesulfonyloxy)phenylsulfonyl)-oxime.

Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropane-sulfonate, 2-naphthoyloxy-1,1,3,3,3-pentafluoropropane-sulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl) difluoromethanesulfonate, and 4-oxo-1-adamantyloxycarbonyldifluoromethanesulfonate.

Also included are oxime sulfonates having the formula (Ox-1):

(Ox-1)

wherein $R^{401}$ is a substituted or unsubstituted $C_1$-$C_{10}$ haloalkylsulfonyl or halobenzenesulfonyl group, $R^{402}$ is a $C_1$-$C_{11}$ haloalkyl group, and $Ar^{401}$ is substituted or unsubstituted aromatic or hetero-aromatic group.

Examples include 2-[2,2,3,3,4,4,5,5-octafluoro-1-(nonafluorobutylsulfonyloxy-imino)-pentyl]fluorene, 2-[2,2,3,3,4,4-pentafluoro-1-(nonafluorobutylsulfonyloxy-imino)-butyl]fluorene, 2-[2,2,3,3,4,4,5,5,6,6-decafluoro-1-(nonafluorobutylsulfonyl-oxyimino)-hexyl]fluorene, 2-[2,2,3,3,4,4,5,5-octafluoro-1-(nonafluorobutylsulfonyloxy-imino)-pentyl]-4-biphenyl, 2-[2,2,3,3,4,4-pentafluoro-1-(nonafluorobutylsulfonyloxy-imino)-butyl]-4-biphenyl, and 2-[2,2,3,3,4,4,5,5,6,6-decafluoro-1-(nonafluorobutylsulfonyl-oxyimino)-hexyl]-4-biphenyl.

Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropane-sulfonate, 2-naphthoyloxy-1,1,3,3,3-pentafluoropropane-sulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl) difluoromethanesulfonate, and 4-oxo-1-adamantyloxycarbonyldifluoromethanesulfonate.

Suitable oxime sulfonate generators using substituted acetonitrile derivatives include α-(p-toluenesulfonyloxy-imino)-phenylacetonitrile, α-(p-chlorobenzenesulfonyloxy-imino)-phenylacetonitrile, α-(4-nitrobenzenesulfonyloxy-imino)-phenylacetonitrile, α-(4-nitro-2-trifluoromethylbenzenesulfonyloxyimino)-phenylacetonitrile, α-(benzenesulfonyloxyimino)-4-chlorophenylacetonitrile, α-(benzenesulfonyloxyimino)-2,4-dichlorophenylacetonitrile, α-(benzenesulfonyloxyimino)-2,6-dichlorophenylacetonitrile, α-(benzenesulfonyloxyimino)-4-methoxyphenylacetonitrile, α-(2-chlorobenzenesulfonyloxyimino)-4-methoxyphenylaceto-nitrile, α-(benzenesulfonyloxyimino)-2-thienylacetonitrile, α-(4-dodecylbenzenesulfonyloxyimino)-phenylacetonitrile, α-[(4-toluenesulfonyloxyimino)-4-methoxyphenyl]acetonitrile, α-[(dodecylbenzenesulfonyloxyimino)-4-methoxyphenyl] acetonitrile, α-(tosyloxyimino)-3-thienylacetonitrile, α-(methylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, and α-(n-butylsulfonyloxyimino)-1-cyclohexenylacetonitrile.

Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Suitable bisoxime sulfonates include bis(α-(p-toluenesulfonyloxy)imino)-p-phenylenediacetonitrile, bis(α-(benzenesulfonyloxy)imino)-p-phenylenediacetonitrile, bis(α-(methanesulfonyloxy)imino)-p-phenylenediacetonitrile, bis(α-(butanesulfonyloxy)imino)-p-phenylenediacetonitrile, bis(α-(10-camphorsulfonyloxy)imino)-p-phenylenediacetonitrile, bis(α-(trifluoromethanesulfonyloxy)imino)-p-phenylenediacetonitrile, bis(α-(4-methoxybenzenesulfonyloxy)imino)-p-phenylenediacetonitrile, bis(α-(p-toluenesulfonyloxy)imino)-m-phenylenediacetonitrile, bis(α-(benzenesulfonyloxy)imino)-m-phenylenediacetonitrile, bis(α-(methanesulfonyloxy)imino)-m-phenylenediacetonitrile, bis(α-(butanesulfonyloxy)imino)-m-phenylenediacetonitrile, bis(α-(10-camphorsulfonyloxy)imino)-m-phenylenediacetonitrile, bis(α-(trifluoromethanesulfonyloxy)imino)-m-phenylenediacetonitrile, bis(α-(4-methoxybenzenesulfonyloxy)imino)-m-phenylenediacetonitrile, etc.

Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

When the photoacid generator (B) is added to the KrF excimer laser resist composition, preference is given to sulfonium salts, bissulfonyldiazomethanes, N-sulfonyloxyimides and oxime-O-sulfonates. Illustrative preferred photoacid generators include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(p-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(p-toluenesulfonyl-oxy)benzenesulfonate, 4-tert-butylphenyldiphenylsulfonium camphorsulfonate, tris(4-methylphenyl)sulfonium camphorsulfonate, tris(4-tert-butylphenyl)sulfonium camphorsulfonate, bis(tert-butylsulfonyl)diazomethane, bis(cyclohexylsulfonyl)diazomethane, bis(2,4-dimethylphenylsulfonyl)diazomethane, bis(4-n-hexyloxyphenylsulfonyl)diazomethane, bis(2-methyl-4-n-hexyloxyphenylsulfonyl)diazomethane, bis(2,5-dimethyl-4-n-hexyloxyphenylsulfonyl)diazomethane, bis(3,5-dimethyl-4-n-hexyloxyphenylsulfonyl)diazomethane, bis(2-methyl-5-isopropyl-4-n-hexyloxy)phenylsulfonyldiazomethane, bis(4-tert-butylphenylsulfonyl)diazomethane, N-camphorsulfonyloxy-5-norbornene-2,3-dicarboxylic acid imide, N-p-toluenesulfonyloxy-5-norbornene-2,3-dicarboxylic acid imide, (5-(10-camphorsulfonyl)oxyimino-5H-thiophen-2-ylidene)(2-methylphenyl)acetonitrile, and (5-(p-toluenesulfonyl)oxyimino-5H-thiophen-2-ylidene)(2-methylphenyl)acetonitrile.

When the photoacid generator (B) is added to the ArF laser resist composition, preference is given to sulfonium salts and oxime-O-sulfonates. Illustrative preferred photoacid generators include triphenylsulfonium trifluoromethanesulfonate, triphenylsulfonium pentafluoroethanesulfonate, triphenylsulfonium heptafluoropropanesulfonate, triphenylsulfonium nonafluorobutanesulfonate, triphenylsulfonium tridecafluorohexanesulfonate, triphenylsulfonium heptadecafluorooctanesulfonate, triphenylsulfonium perfluoro(4-ethylcyclohexane)sulfonate, 4-methylphenyldiphenylsulfonium nonafluorobutanesulfonate, 2-oxo-2-phenylethylthiacyclopentanium nonafluorobutane-sulfonate, 4-tert-butylphenyldiphenylsulfonium nonafluorobutanesulfonate, 4-tert-butylphenyldiphenylsulfonium perfluoro(4-ethylcyclo-hexane)sulfonate, 4-tert-butylphenyldiphenylsulfonium heptafluorooctane-sulfonate, triphenylsulfonium 1,1-difluoro-2-naphthylethanesulfonate, triphenylsulfonium 1,1,2,2-tetrafluoro-2-(norbornan-2-yl)-ethanesulfonate, triphenylsulfonium 2-benzoyloxy-1,1,3,3,3-pentafluoropropane-sulfonate, triphenylsulfonium 1,1,3,3,3-pentafluoro-2-(pivaloyloxy)-propanesulfonate, triphenylsulfonium 2-(cyclohexanecarbonyloxy)-1,1,3,3,3-pentafluoropropane-sulfonate, triphenylsulfonium 2-(2-naphthoyloxy)-1,1,3,3,3-pentafluoro-propanesulfonate, triphenylsulfonium 2-(1-adamantanecarbonyloxy)-1,1,3,3,3-pentafluoropropanesulfonate, triphenylsulfonium 2-hydroxy-1,1,3,3,3-pentafluoropropane-sulfonate, triphenylsulfonium adamantanemethoxycarbonyldifluoromethane-sulfonate, triphenylsulfonium 1-(3-hydroxymethyladamantane)methoxycarbonyldifluoromethanesulfonate, triphenylsulfonium methoxycarbonyldifluoromethanesulfonate, 4-tert-butylphenyldiphenylsulfonium 2-benzoyloxy-1,1,3,3,3-pentafluoropropanesulfonate, 4-tert-butylphenyldiphenylsulfonium 1,1,3,3,3-pentafluoro-2-(pivaloyloxy)propanesulfonate, 4-tert-butylphenyldiphenylsulfonium 2-(cyclohexanecarbonyloxy)-1,1,3,3,3-pentafluoropropanesulfonate, 4-tert-butylphenyldiphenylsulfonium 2-(2-naphthoyloxy)-1,1,3,3,3-pentafluoropropanesulfonate, 4-tert-butylphenyldiphenylsulfonium 2-(1-adamantanecarbonyloxy)-1,1,3,3,3-pentafluoropropanesulfonate, 4-tert-butylphenyldiphenylsulfonium 2-hydroxy-1,1,3,3,3-pentafluoropropanesulfonate, 4-tert-butylphenyldiphenylsulfonium adamantanemethoxycarbonyldifluoromethanesulfonate, 4-tert-butylphenyldiphenylsulfonium 1-(3-hydroxymethyladamantane)methoxycarbonyldifluoromethanesulfonate, 4-tert-butylphenyldiphenylsulfonium methoxycarbonyldifluoro-methanesulfonate, 2-oxo-2-phenylethylthiacyclopentanium 2-benzoyloxy-1,1,3,3,3-pentafluoropropanesulfonate, 2-oxo-2-phenylethylthiacyclopentanium 2-cyclohexanecarbonyl-oxy-1,1,3,3,3-pentafluoropropanesulfonate, triphenylsulfonium perfluoro(1,3-propylenebissulfonyl)imide, triphenylsulfonium bis(pentafluoroethylsulfonyl)imide, 2-(2,2,3,3,4,4,5,5-octafluoro-1-(nonafluorobutylsulfonyloxy-imino)pentyl)fluorene, 2-(2,2,3,3,4,4-pentafluoro-1-(nonafluorobutylsulfonyloxy-imino)butyl)fluorene, 2-(2,2,3,3,4,4,5,5,6,6-decafluoro-1-(nonafluorobutylsulfonyl-oxyimino)hexyl)fluorene, 2-(2,2,3,3,4,4,5,5-octafluoro-1-(2-(cyclohexanecarbonyloxy)-1,1,3,3,3-pentafluoropropanesulfonyloxyimino)pentyl)fluorene, 2-(2,2,3,3,4,4-pentafluoro-1-(2-(cyclohexanecarbonyloxy)-1,1,3,3,3-pentafluoropropanesulfonyloxyimino)butyl)fluorene, and 2-(2,2,3,3,4,4,5,5,6,6-decafluoro-1-(nonafluorobutyl-sulfonyloxyimino)hexyl)fluorene.

When the photoacid generator (B) is added to the ArF immersion lithography resist composition, preference is given to sulfonium salts and oxime-O-sulfonates. Illustrative preferred photoacid generators include triphenylsulfonium nonafluorobutanesulfonate, triphenylsulfonium tridecafluorohexanesulfonate, triphenylsulfonium heptadecafluorooctanesulfonate, triphenylsulfonium perfluoro(4-ethylcyclohexane)sulfonate, 4-methylphenyldiphenylsulfonium nonafluorobutanesulfonate, 2-oxo-2-phenylethylthiacyclopentanium nonafluorobutane-sulfonate, 4-tert-butylphenyldiphenylsulfonium nonafluorobutane-sulfonate, 4-tert-butylphenyldiphenylsulfonium perfluoro(4-ethylcyclo-hexane)sulfonate, 4-tert-butylphenyldiphenylsulfonium heptafluorooctanesulfonate, triphenylsulfonium 1,1-difluoro-2-naphthylethanesulfonate, triphenylsulfonium 1,1,2,2-tetrafluoro-2-(norbornan-2-yl)-ethanesulfonate, triphenylsulfonium 2-benzoyloxy-1,1,3,3,3-pentafluoropropanesulfonate, triphenylsulfonium 1,1,3,3,3-pentafluoro-2-(pivaloyloxy)-propanesulfonate, triphenylsulfonium 2-(cyclohexanecarbonyloxy)-1,1,3,3,3-pentafluoropropanesulfonate, triphenylsulfonium 2-(2-naphthoyloxy)-1,1,3,3,3-pentafluoro-propanesulfonate, triphenylsulfonium 2-(1-adamantanecarbonyloxy)-1,1,3,3,3-pentafluoropropanesulfonate, triphenylsulfonium 2-hydroxy-1,1,3,3,3-pentafluoropropane-sulfonate, triphenylsulfonium adamantanemethoxycarbonyldifluoromethane-sulfonate, triphenylsulfonium 1-(3-hydroxymethyladamantane)methoxy-carbonyldifluoromethanesulfonate, triphenylsulfonium methoxycarbonyldifluoromethanesulfonate, 4-tert-butylphenyldiphenylsulfonium 2-benzoyloxy-1,1,3,3,3-pentafluoropropanesulfonate, 4-tert-butylphenyldiphenylsulfonium 1,1,3,3,3-pentafluoro-2-(pivaloyloxy)propanesulfonate, 4-tert-butylphenyldiphenylsulfonium 2-(cyclohexanecarbonyloxy)-1,1,3,3,3-pentafluoropropanesulfonate, 4-tert-butylphenyldiphenylsulfonium 2-(2-naphthoyloxy)-1,1,3,3,3-pentafluoropropanesulfonate, 4-tert-butylphenyldiphenylsulfonium 2-(1-adamantanecarbonyloxy)-1,1,3,3,3-pentafluoropropanesulfonate, 4-tert-butylphenyldiphenylsulfonium 2-hydroxy-1,1,3,3,3-pentafluoropropanesulfonate, 4-tert-butylphenyldiphenylsulfonium adamantanemethoxycarbonyldifluoromethanesulfonate, 4-tert-butylphenyldiphenylsulfonium 1-(3-hydroxymethyladamantane)methoxycarbonyldifluoromethanesulfonate, 4-tert-butylphenyldiphenylsulfonium methoxycarbonyldifluoro-methanesulfonate, 2-oxo-2-phenylethylthiacyclopentanium 2-benzoyloxy-1,1,3,3,3-pentafluoropropanesulfonate, 2-oxo-2-phenylethylthiacyclopentanium 2-cyclohexanecarbonyl-oxy-1,1,3,3,3-pentafluoropropanesulfonate, triphenylsulfonium perfluoro(1,3-propylenebissulfonyl)imide, triphenylsulfonium bis(pentafluoroethylsulfonyl)imide, 2-(2,2,3,3,4,4,5,5-octafluoro-1-(nonafluorobutylsulfonyloxy-imino)pentyl)fluorene, 2-(2,2,3,3,4,4-pentafluoro-1-(nonafluorobutylsulfonyloxy-imino)butyl)fluorene, 2-(2,2,3,3,4,4,5,5,6,6-decafluoro-1-(nonafluorobutylsulfonyl-oxyimino)hexyl)fluorene, 2-(2,2,3,3,4,4,5,5-octafluoro-1-(2-(cyclohexanecarbonyloxy)-1,1,3,3,3-pentafluoropropanesulfonyloxyimino)pentyl)fluorene, 2-(2,2,3,3,4,4-pentafluoro-1-(2-(cyclohexanecarbonyloxy)-1,1,3,3,3-pentafluoropropanesulfonyloxyimino)butyl)fluorene, and 2-(2,2,3,3,4,4,5,5,6,6-decafluoro-1-(nonafluorobutyl-sulfonyloxyimino)hexyl)fluorene.

In the chemically amplified resist composition, the photoacid generator (B) may be added in any desired amount as long as the objects of the invention are not compromised. An appropriate amount of the photoacid generator (B) is 0.1 to 10 parts, and more preferably 0.1 to 5 parts by weight per 100 parts by weight of the base resin in the composition. Too high a proportion of the photoacid generator (B) may give rise to problems of degraded resolution and foreign matter upon development and resist film peeling. The photoacid generators may be used alone or in admixture of two or more. The transmittance of the resist film can be controlled by using an photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If an onium salt capable of generating a strong acid and an onium salt capable of generating a weak acid are used in admixture, an exchange from the strong acid to the weak acid as above can take place, but it never happens that the weak acid collides with the unreacted onium salt capable of generating a strong acid to induce a salt exchange. This is because of a likelihood of an onium cation forming an ion pair with a stronger acid anion.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Organic Solvent

The organic solvent (C) used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, and mixtures thereof because the acid generator is most soluble therein.

An appropriate amount of the organic solvent used is 200 to 1,000 parts, especially 400 to 800 parts by weight per 100 parts by weight of the base resin.

Quencher

A quencher (D) may be optionally used in the resist composition of the invention. The term "quencher" as used herein has a meaning generally known in the art and refers to a compound capable of suppressing the rate of diffusion when the acid generated by the acid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, N,N-bis(hydroxyethyl)aniline, 2-methylaniline, 3-methylaniline, 4-methylaniline, ethylaniline, propylaniline, dimethylaniline, 2,6-diisopropylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazane derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds with carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). A typical nitrogen-containing compound with sulfonyl group is 3-pyridinesulfonic acid. Examples of suitable nitrogen-containing compounds with hydroxyl group, nitrogen-containing compounds with hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide.

Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-tert-butoxycarbonyl-N,N-dicyclohexylamine, N-tert-butoxycarbonylbenzimidazole, and oxazolidinone.

Suitable ammonium salts include pyridinium p-toluenesulfonate, triethylammonium p-toluenesulfonate, trioctylammonium p-toluenesulfonate, triethylammonium 2,4,6-triisopropylbenzenesulfonate, trioctylammonium 2,4,6-triisopropylbenzenesulfonate, triethylammonium camphorsulfonate, trioctylammonium camphorsulfonate, tetramethylammonium hydroxide, tetraethylammonium hydroxide, tetrabutylammonium hydroxide, benzyltrimethylammonium hydroxide, tetramethylammonium p-toluenesulfonate, tetrabutylammonium p-toluenesulfonate, benzyltrimethylammonium p-toluenesulfonate, tetramethylammonium camphorsulfonate, tetrabutylammonium camphorsulfonate, benzyltrimethylammonium camphorsulfonate, tetramethylammonium 2,4,6-triisopropylbenzenesulfonate, tetrabutylammonium 2,4,6-triisopropylbenzenesulfonate, benzyltrimethylammonium 2,4,6-triisopropylbenzenesulfonate, tetramethylammonium acetate, tetrabutylammonium acetate, benzyltrimethylammonium acetate, tetramethylammonium benzoate, tetrabutylammonium benzoate, and benzyltrimethylammonium benzoate.

In addition, amine compounds of the following general formula (B)-1 may also be included alone or in admixture.

$$N(X)_n(Y)_{3-n} \quad \text{(B)-1}$$

In the formula, n is equal to 1, 2 or 3. The side chain X is independently selected from groups of the following general formulas (X)-1 to (X)-3. The side chain Y is independently hydrogen or a straight, branched or cyclic $C_1$-$C_{20}$ alkyl group in which some or all hydrogen atoms may be substituted by fluorine atoms and which may contain an ether or hydroxyl group. Two or three X may bond together to form a ring.

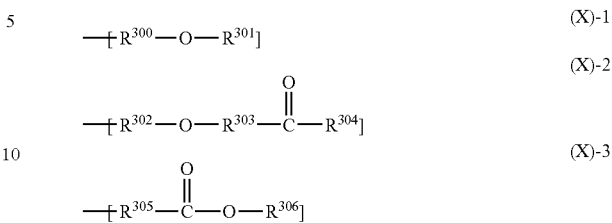

In the formulas, $R^{300}$, $R^{302}$ and $R^{305}$ are independently straight or branched $C_1$-$C_4$ alkylene groups; $R^{301}$ and $R^{304}$ are independently hydrogen or straight, branched or cyclic $C_1$-$C_{20}$ alkyl groups in which some or all hydrogen atoms may be substituted by fluorine atoms and which may contain one or more hydroxyl, ether, ester groups or lactone rings; $R^{303}$ is a single bond or a straight or branched $C_1$-$C_4$ alkylene group; $R^{306}$ is a straight, branched or cyclic $C_1$-$C_{20}$ alkyl group in which some or all hydrogen atoms may be substituted by fluorine atoms and which may contain one or more hydroxyl, ether, ester groups or lactone rings.

Illustrative examples of the compounds of formula (B)-1 include, but are not limited to, tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis (2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)-amine, N-butyl-bis(methoxycarbonylmethyl)amine, N-hexyl-bis(methoxycarbonylmethyl)amine, and β-(diethylamino)-δ-valerolactone.

Also useful are one or more of cyclic structure-bearing amine compounds having the following general formula (B)-2.

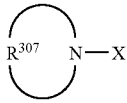
(B)-2

Herein X is as defined above, and $R^{307}$ is a straight or branched $C_2$-$C_{20}$ alkylene group in which some or all hydrogen atoms may be substituted by fluorine atoms and which may contain one or more carbonyl, ether, ester or sulfide groups.

Illustrative examples of the cyclic structure-bearing amine compounds having formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-[2-(2-methoxyethoxy)ethoxy]ethylmorpholine, 2-[2-(2-butoxyethoxy)ethoxy]ethylmorpholine, 2-{2-[2-(2-methoxyethoxy)ethoxy]ethoxy}ethylmorpholine, 2-{2-[2-(2-butoxyethoxy)ethoxy]ethoxy}ethylmorpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, 2-methoxyethyl morpholinoacetate, 2-morpholinoethyl 2-methoxyacetate, 2-morpholinoethyl 2-(2-methoxyethoxy)acetate, 2-morpholinoethyl 2-[2-(2-methoxyethoxy)ethoxy]acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl cyclohexanecarboxylate, and 2-morpholinoethyl adamantanecarboxylate.

Also, one or more of cyano-bearing amine compounds having the following general formulae (B)-3 to (B)-6 may be added.

(B)-3

(B)-4

(B)-5

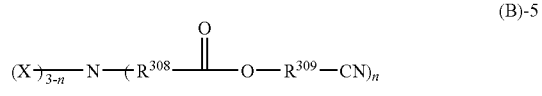
(B)-6

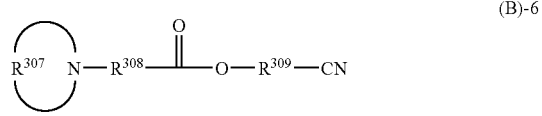

Herein, X, $R^{307}$ and n are as defined in formula (B)-1, and $R^{308}$ and $R^{309}$ each are independently a straight or branched $C_1$-$C_4$ alkylene group.

Illustrative examples of the cyano-bearing amine compounds having formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiono-nitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)

ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl) aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-amino-propionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are amine compounds having an imidazole structure and a polar functional group, represented by the general formula (B)-7.

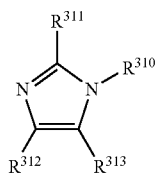

(B)-7

Herein, $R^{310}$ is a straight, branched or cyclic $C_2$-$C_{20}$ alkyl group in which some or all hydrogen atoms may be substituted by fluorine atoms and which has one or more polar functional groups. The polar functional group is selected from among hydroxyl, carbonyl, ester, ether, sulfide, carbonate, cyano and acetal groups and mixtures thereof. $R^{311}$, $R^{312}$ and $R^{313}$ are each independently a hydrogen atom, a straight, branched or cyclic $C_1$-$C_{10}$ alkyl group, aryl group or aralkyl group.

Also included are amine compounds having a benzimidazole structure and a polar functional group, represented by the general formula (B)-8.

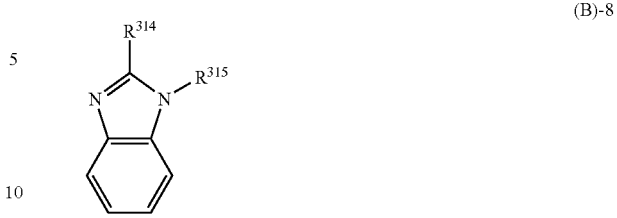

(B)-8

Herein, $R^{314}$ is a hydrogen atom, a straight, branched or cyclic $C_1$-$C_{10}$ alkyl group, aryl group or aralkyl group. $R^{315}$ is a straight, branched or cyclic $C_1$-$C_{20}$ alkyl group in which some or all hydrogen atoms may be substituted by fluorine atoms and which has one or more polar functional groups. The alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

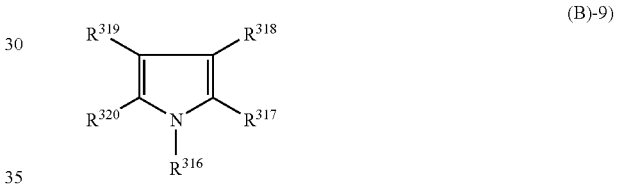

(B)-9

(B)-10

Herein, A is a nitrogen atom or =C—$R^{322}$. B is a nitrogen atom or =C—$R^{323}$. $R^{316}$ is a straight, branched or cyclic $C_2$-$C_{20}$ alkyl group in which some or all hydrogen atoms may be substituted by fluorine atoms and which has one or more polar functional groups, the polar functional group being selected from among hydroxyl, carbonyl, ester, ether, sulfide, carbonate, cyano and acetal groups and mixtures thereof. $R^{317}$, $R^{318}$, $R^{319}$ and $R^{320}$ are each independently a hydrogen atom, a straight, branched or cyclic $C_1$-$C_{10}$ alkyl group or aryl group, or a pair of $R^{317}$ and $R^{318}$ and a pair of $R^{319}$ and $R^{320}$, taken together, may form a benzene, naphthalene or pyridine ring with the carbon atoms to which they are attached. $R^{321}$ is a hydrogen atom, a straight, branched or cyclic $C_1$-$C_{10}$ alkyl group or aryl group. $R^{322}$ and $R^{323}$ each are a hydrogen atom, a straight, branched or cyclic $C_1$-$C_{10}$ alkyl group or aryl group, or a pair of $R^{321}$ and $R^{323}$, taken together, may form a benzene or naphthalene ring with the carbon atoms to which they are attached.

Also included are organic nitrogen-containing compounds having an aromatic carboxylic acid ester structure, represented by the general formulae (B)-11 to (B)-14.

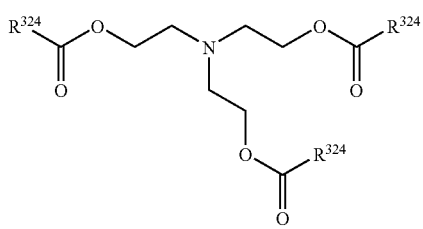
(B)-11

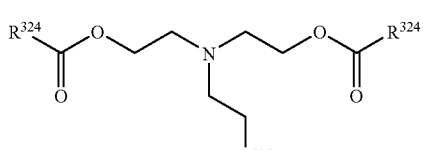
(B)-12

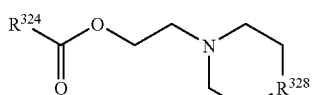
(B)-13

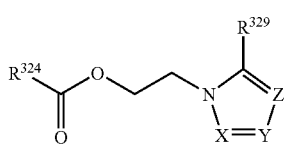
(B)-14

Herein $R^{324}$ is a $C_6$-$C_{20}$ aryl group or $C_4$-$C_{20}$ hetero-aromatic group, in which some or all hydrogen atoms may be replaced by halogen atoms, straight, branched or cyclic $C_1$-$C_{20}$ alkyl groups, $C_6$-$C_{20}$ aryl groups, $C_1$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or —O(CH$_2$CH$_2$O)$_n$— group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring with the carbon atoms to which they are attached.

Further included are amine compounds of 7-oxanorbornane-2-carboxylic ester structure, represented by the general formula (B)-15.

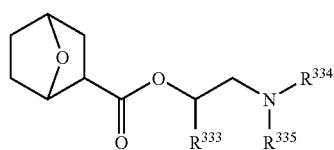
(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms with the nitrogen atom to which they are attached.

The quenchers may be used alone or in admixture of two or more. The quencher is preferably formulated in an amount of 0.001 to 2 parts, and especially 0.01 to 1 part by weight, per 100 parts by weight of the total base resin. Less than 0.001 phr of the quencher may achieve no addition effect whereas more than 2 phr may lead to too low a sensitivity.

Surfactant

Optionally, the resist composition of the invention may further comprise a surfactant which is commonly used for improving the coating characteristics. The surfactant may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Fluorad FC-430 and FC-431 from Sumitomo 3M, Ltd., Surflon S-141, S-145, KH-10, KH-20, KH-30 and KH-40 from Asahi Glass Co., Ltd., Unidyne DS-401, DS-403 and DS-451 from Daikin Industry Co., Ltd., Megaface F-8151 from Dai-Nippon Ink & Chemicals, Inc., and X-70-092 and X-70-093 from Shin-Etsu Chemical Co., Ltd. Preferred surfactants are Fluorad FC-430 from Sumitomo 3M, Ltd., KH-20 and KH-30 from Asahi Glass Co., Ltd., and X-70-093 from Shin-Etsu Chemical Co., Ltd. The surfactant is preferably compounded in an amount of 0.01 to 1 part, and especially 0.05 to 0.5 part by weight, per 100 parts by weight of the total base resin.

While the resist composition of the invention typically comprises a polymer or base resin, acid generator, organic solvent and quencher as described above, there may be added optional other ingredients such as dissolution inhibitors, acidic compounds, stabilizers, and dyes. Optional ingredients may be added in conventional amounts so long as this does not compromise the objects of the invention.

Process

Pattern formation using the resist composition of the invention may be carried out by a known lithographic technique. For example, the resist composition is applied onto a substrate such as a silicon wafer by spin coating or the like to form a resist film having a thickness of 0.05 to 2.0 μm, which is then pre-baked on a hot plate at 60 to 150° C. for 1 to 10 minutes, and preferably at 80 to 140° C. for 1 to 5 minutes. A patterning mask having the desired pattern is then placed over the resist film, and the film exposed through the mask to an electron beam or to high-energy radiation such as deep-UV ray, excimer laser, or x-ray in a dose of about 1 to 200 mJ/cm$^2$, and preferably about 10 to 100 mJ/cm$^2$. Light exposure may be done by a conventional exposure process or in some cases, by an immersion process of providing liquid impregnation between the mask and the resist. The resist film is then post-exposure baked (PEB) on a hot plate at 60 to 150° C. for 1 to 5 minutes, and preferably at 80 to 140° C. for 1 to 3 minutes. Finally, development is carried out using as the developer an aqueous alkali solution, such as a 0.1 to 5 wt % (preferably 2 to 3 wt %) aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV ray having a wavelength of 250 to 190 nm, an excimer laser, x-ray, or an electron beam. The desired pattern may not be obtainable outside the upper and lower limits of the above range.

More specifically, pattern formation using the resist composition of the invention may be performed by well-known lithography processes. The process generally involves coating, heat treatment (or prebaking), exposure, heat treatment (post-exposure baking, PEB), and development. If necessary, any additional steps may be added.

For pattern formation, the resist composition is first applied onto a substrate (on which an integrated circuit is to be formed, e.g., Si, $SiO_2$, SiN, SiON, TiN, WSi, BPSG, SOG, organic antireflective coating, Cr, CrO, CrON, MoSi, etc.) by a suitable coating technique such as spin coating, roll coating, flow coating, dip coating, spray coating or doctor coating. The coating is prebaked on a hot plate at a temperature of 50 to 150° C. for 1 to 10 minutes, preferably 60 to 140° C. for 1 to 5 minutes. The resulting resist film is generally 0.01 to 2.0 μm thick.

A relationship of a reduced thickness of resist film to an etch selectivity ratio between resist film and processable substrate imposes severer limits on the process. Under consideration is the tri-layer process in which a resist layer, a silicon-containing intermediate layer, an undercoat layer having a high carbon density and high etch resistance, and a processable substrate are laminated in sequence from top to bottom. On etching with oxygen gas, hydrogen gas, ammonia gas or the like, a high etch selectivity ratio is available between the silicon-containing intermediate layer and the undercoat layer, which allows for thickness reduction of the silicon-containing intermediate layer. A relatively high etch selectivity ratio is also available between the monolayer resist and the silicon-containing intermediate layer, which allows for thickness reduction of the monolayer resist. The method for forming the undercoat layer in this case includes a coating and baking method and a CVD method. In the case of coating, novolac resins and resins obtained by polymerization of fused ring-containing olefins are used. In the CVD film formation, gases such as butane, ethane, propane, ethylene and acetylene are used. For the silicon-containing intermediate layer, either a coating method or a CVD method may be employed. The coating method uses silsesquioxane, polyhedral oligomeric silsesquioxane (POSS) and the like while the CVD method uses silane gases as the reactant. The silicon-containing intermediate layer may have an antireflection function with a light absorbing ability and have photo-absorptive groups like phenyl groups, or it may be a SiON film. An organic film may be formed between the silicon-containing intermediate layer and the photoresist, and the organic film in this case may be an organic antireflective coating. After the photoresist film is formed, deionized water rinsing (or post-soaking) may be carried out for extracting the photoacid generator and the like from the film surface or washing away particles, or a protective film may be coated.

With a mask having a desired pattern placed above the resist film, the resist film is then exposed to radiation such as UV, deep-UV, electron beam, x-ray, excimer laser light, γ-ray and synchrotron radiation. The exposure dose is preferably about 1 to 200 $mJ/cm^2$, more preferably about 10 to 100 $mJ/cm^2$. The film is further baked on a hot plate at 60 to 150° C. for 1 to 5 minutes, preferably 80 to 120° C. for 1 to 3 minutes (post-exposure baking=PEB). Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray techniques. In this way, a desired resist pattern is formed on the substrate. It is appreciated that the resist composition of the invention is suited for nano-scale patterning using such high-energy radiation as deep UV with a wavelength of 254 to 193 nm, vacuum UV with a wavelength of 157 nm, electron beam, soft x-ray, x-ray, excimer laser light, γ-ray and synchrotron radiation, and best suited for nano-scale patterning using high-energy radiation in the wavelength range of 180 to 200 nm.

Immersion lithography can be applied to the resist composition of the invention. The ArF immersion lithography uses a liquid having a refractive index of at least 1 and highly transparent at the exposure wavelength such as deionized water or alkanes as the immersion solvent. The immersion lithography involves prebaking a resist film and exposing the resist film to light through a projection lens, with deionized water or similar liquid interposed between the resist film and the projection lens. Since this allows projection lenses to be designed to a numerical aperture (NA) of 1.0 or higher, formation of finer size patterns is possible. The immersion lithography is important for the ArF lithography to survive to the 45-nm node, with a further development thereof being accelerated. In the case of immersion lithography, deionized water rinsing (or post-soaking) may be carried out after exposure for removing water droplets left on the resist film, or a protective coating may be applied onto the resist film after pre-baking for preventing any leach-out from the resist and improving water slip on the film surface. The resist protective coating used in the immersion lithography is preferably formed from a solution of a polymer having 1,1,1,3,3,3-hexafluoro-2-propanol residue which is insoluble in water, but soluble in an alkaline developer liquid, in a solvent selected from alcohols of at least 4 carbon atoms, ethers of 8 to 12 carbon atoms, and mixtures thereof.

The water immersion lithography using a NA 1.35 lens achieves an ultimate resolution of 40 to 38 nm at the maximum NA, but cannot reach 32 nm. Efforts have been made to develop higher refractive index materials in order to further increase NA. It is the minimum refractive index among projection lens, liquid, and resist film that determines the NA limit of lenses. In the case of water immersion, the refractive index of water is the lowest in comparison with the projection lens (refractive index 1.5 for synthetic quartz) and the resist film (refractive index 1.7 for prior art methacrylate-based film). Thus the NA of projection lens is determined by the refractive index of water. Recent efforts succeeded in developing a highly transparent liquid having a refractive index of 1.65. In this situation, the refractive index of projection lens made of synthetic quartz is the lowest, suggesting a need to develop a projection lens material with a higher refractive index. LuAG (lutetium aluminum garnet $Lu_3Al_5O_{12}$) having a refractive index of at least 2 is the most promising material.

The resist composition of the invention is applicable to immersion lithography using a high refractive index liquid.

The process that now draws attention as the technology for extending the life of the ArF lithography is a double patterning process involving a first set of exposure and development to form a first pattern and a second set of exposure and development to form a second pattern between features of the first pattern. See Proc. SPIE, Vol. 5754, p 1508 (2005). A number of double patterning processes have been proposed. One exemplary process involves a first set of exposure and development to form a photoresist pattern having lines and spaces at intervals of 1:3, processing the underlying layer of hard mask by dry etching, applying another layer of hard mask thereon, a second set of exposure and development of a photoresist film to form a line pattern in the spaces of the first exposure, and processing the hard mask by dry etching, thereby forming a line-and-space pattern at a half pitch of the first pattern. An alternative process involves a first set of exposure and development to form a photoresist pattern having spaces and lines at intervals of 1:3, processing the underlying layer of hard mask by dry etching, applying a photoresist layer thereon, a second set of exposure and development to form a second space pattern on the remaining hard mask portion, and processing the hard mask by dry etching. In either process, the hard mask is processed by two dry etchings.

While the former process requires two applications of hard mask, the latter process uses only one layer of hard mask, but requires to form a trench pattern which is difficult to resolve as compared with the line pattern. The latter process includes the use of a negative resist material in forming the trench pattern. This allows for use of high contrast light as in the formation of lines as a positive pattern. However, since the negative resist material has a lower dissolution contrast than the positive resist material, a comparison of the formation of lines from the positive resist material with the formation of a trench pattern of the same size from the negative resist material reveals that the resolution achieved with the negative resist material is lower. After a wide trench pattern is formed from the positive resist material by the latter process, there may be applied a thermal flow method of heating the substrate for shrinkage of the trench pattern, or a RELACS method of coating a water-soluble film on the trench pattern as developed and heating to induce crosslinking at the resist film surface for achieving shrinkage of the trench pattern. These have the drawbacks that the proximity bias is degraded and the process is further complicated, leading to reduced throughputs.

Both the former and latter processes require two etchings for substrate processing, leaving the issues of a reduced throughput and deformation and misregistration of the pattern by two etchings. One method that proceeds with a single etching is by using a negative resist material in a first exposure and a positive resist material in a second exposure. Another method is by using a positive resist material in a first exposure and a negative resist material in a higher alcohol of 4 or more carbon atoms, in which the positive resist material is not dissolvable, in a second exposure. However, these methods using negative resist materials with low resolution entail degradation of resolution.

If first exposure is followed by second exposure at a half-pitch shifted position, the optical energy of second exposure offsets the optical energy of first exposure so that the contrast becomes zero. If a contrast enhancement layer (CEL) is formed on the resist film, the incident light to the resist film becomes nonlinear so that the first and second exposures do not offset each other. Thus an image having a half pitch is formed. See Jpn. J. Appl. Phy. Vol. 33 (1994) p 6874-6877. It is expected that similar effects are produced by using an acid generator capable of two photon absorption to provide a nonlinear contrast.

The critical issue associated with double patterning is an overlay accuracy between first and second patterns. Since the magnitude of misregistration is reflected by a variation of line size, an attempt to form 32-nm lines at an accuracy of 10%, for example, requires an overlay accuracy within 3.2 nm. Since currently available scanners have an overlay accuracy of the order of 8 nm, a significant improvement in accuracy is necessary.

Now under investigation is the resist pattern freezing technology involving forming a first resist pattern on a substrate, taking any suitable means for insolubilizing the resist pattern with respect to the resist solvent and alkaline developer, applying a second resist thereon, and forming a second resist pattern in space portions of the first resist pattern. With this freezing technology, etching of the substrate is required only once, leading to improved throughputs and avoiding the problem of misregistration due to stress relaxation of the hard mask during etching. In the freezing technology, development efforts are focused on the step of forming a resist film on the first resist pattern and the optical or thermal step of insolubilizing the resist pattern. The resist composition of the invention is also applicable to such a process. Examples of light used for the freezing purpose include preferably light with a wavelength of up to 300 nm, more preferably up to 200 nm, specifically ArF excimer light of wavelength 193 nm, $Xe_2$ excimer light of 172 nm, $F_2$ excimer light of 157 nm, $Kr_2$ excimer light of 146 nm, and $Ar_2$ excimer light of 126 nm, and the exposure dose in the case of light is preferably in the range of 10 mJ/cm$^2$ to 10 J/cm$^2$. Irradiation from an excimer laser of sub-200 nm wavelength, especially 193 nm, 172 nm, 157 nm, 146 nm, and 122 nm, or an excimer lamp not only causes the photoacid generator to generate an acid, but also promotes photo-induced crosslinking reaction. In a further example where a thermal acid generator in the form of an ammonium salt is added to a photoresist composition, specifically in an amount of 0.001 to 20 parts, more specifically 0.01 to 10 parts by weight per 100 parts by weight of the base resin, an acid can be generated by heating. In this case, acid generation and crosslinking reaction proceed simultaneously. The preferred heating conditions include a temperature of 100 to 300° C., and especially 130 to 250° C., and a time of 10 to 300 seconds. As a result, a crosslinked resist film is formed which is insoluble in solvents and alkaline developers.

The resist composition of the invention has a further advantage that the feature size of the pattern as developed may be reduced by a variety of shrink techniques. For example, the hole size may be shrunk by well-known techniques such as thermal flow, RELACS, SAFIRE, and WASOOM. The hole size may be effectively reduced by thermal flow particularly when the polymer is blended with a hydrogenated ROMP (ring-opening metathesis polymer) of cycloolefin having a low Tg.

EXAMPLE

Examples and Comparative Examples are given below by way of illustration and not by way of limitation. The abbreviation "Mw" is a weight average molecular weight as measured by GPC using polystyrene standards, and "pbw" is parts by weight.

Example 1

Lactone-containing compounds within the scope of the invention were synthesized according to the following formulation.

Example 1-1

Synthesis of Monomer 1

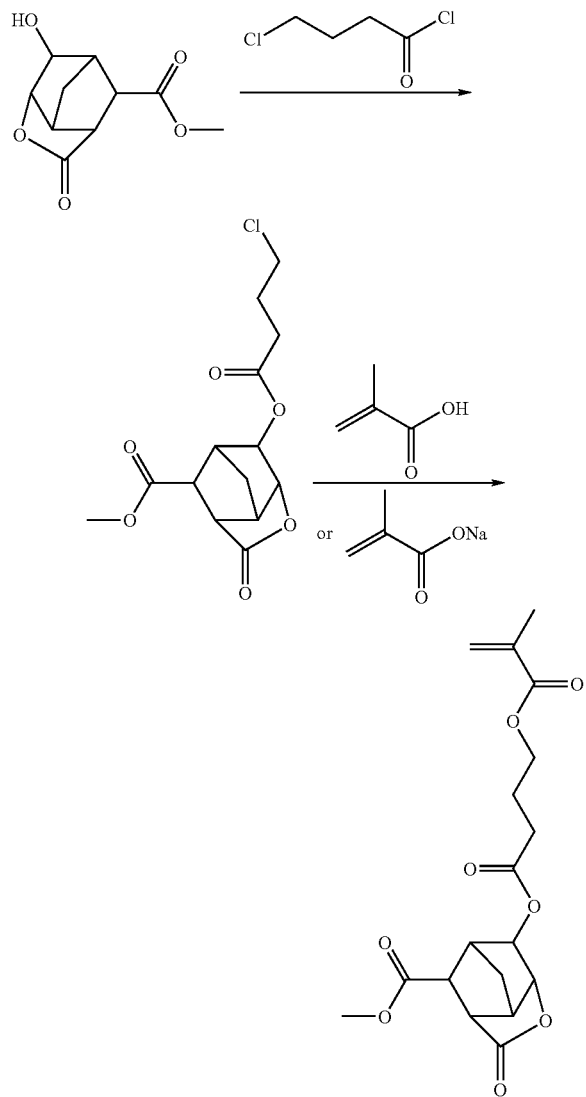

Example 1-1-1

Synthesis of 7-methoxycarbonyl-2-oxohexahydro-3,5-methano-2H-cyclopenta[b]furan-6-yl 4-chlorobutyrate In 180 ml of tetrahydrofuran were dissolved 21.2 g of methyl 6-hydroxy-2-oxohexahydro-3,5-methano-2H-cyclopenta-[b]furan-7-carboxylate and 16.9 g of 4-chlorobutyric acid chloride. To the solution below 20° C., 9.10 g of pyridine was added dropwise. The solution was stirred at room temperature for 1 hour and combined with 40 g of a 5% aqueous solution of sodium hydrogen carbonate, followed by ordinary work-up. There was obtained 30.4 g of a crude product (crude yield 96%).

IR (thin film): ν=2956, 1785, 1737, 1733, 1436, 1367, 1338, 1299, 1274, 1201, 1157, 1118, 1087, 1041, 1014 cm$^{-1}$ $^1$H-NMR (600 MHz in CDCl$_3$):
δ=1.66 (1H, dd), 2.08 (3H, m), 2.51 (2H, t), 2.76 (1H, m), 2.83 (1H, dd), 3.08 (1H, dd), 3.32 (1H, ddd), 3.59 (2H, t), 3.72 (3H, s), 4.57 (1H, d), 5.25 (1H, d) ppm

Example 1-1-2

Synthesis in one route of 7-methoxycarbonyl-2-oxohexahydro-3,5-methano-2H-cyclopenta[b]furan-6-yl 4-(methacryloyloxy)butyrate A mixture of 10.0 g of the 4-chlorobutyrate obtained in Example 1-1-1 and 30 g of dimethylformamide was added dropwise to a mixture of 4.69 g of sodium methacrylate, 0.71 g of sodium iodide and 20 g of dimethylformamide at 60-70° C. The mixture was stirred at the temperature for 8 hours. 100 ml of water was added below 30° C. This was followed by ordinary work-up and silica gel chromatography purification, obtaining 8.12 g of the target compound (yield 70%).

IR (thin film): ν=2983, 2958, 1785, 1737, 1718, 1637, 1436, 1367, 1336, 1321, 1297, 1201, 1157, 1118, 1087, 1014 cm$^{-1}$ $^1$H-NMR (600 MHz in CDCl$_3$):
δ=1.66 (1H, dd), 1.93 (3H, m), 2.01 (2H, q), 2.04 (1H, d), 2.42 (2H, dt), 2.76 (1H, m), 2.82 (1H, dd), 3.08 (1H, dd), 3.31 (1H, t-like), 3.72 (3H, s), 4.18 (2H, t), 4.59 (1H, d), 5.25 (1H, s), 5.56 (1H, m), 6.08 (1H, s) ppm

Example 1-1-3

Synthesis in another route of 7-methoxycarbonyl-2-oxohexahydro-3,5-methano-2H-cyclopenta[b]furan-6-yl 4-(methacryloyloxy)butyrate A mixture of 4.17 g of triethylamine and 10 g of dimethylformamide was added dropwise to a mixture of 3.73 g of methacrylic acid, 10.0 g of the 4-chlorobutyrate obtained in Example 1-1-1, 0.71 g of sodium iodide, and 40 g of dimethylformamide at 60-70° C. The mixture was stirred at the temperature for 8 hours. 100 ml of water was added below 30° C. This was followed by ordinary work-up and recrystallization from toluene and n-hexane, obtaining 10.9 g of the target compound (yield 73%). The spectroscopic data of this compound were exactly identical with those of the compound synthesized in Example 1-1-2.

Example 1-2

Synthesis of Monomer 2

The procedure of Examples 1-1-1 and 1-1-3 was repeated aside from using acrylic acid instead of methacrylic acid. There was obtained 7-methoxycarbonyl-2-oxohexahydro-3,5-methano-2H-cyclopenta[b]furan-6-yl 4-(acryloyloxy)butyrate. Two-step yield 55%.

Example 1-3

Synthesis of Monomer 3

Example 1-3-1

Synthesis of 2-oxo-4-oxahexahydro-3,5-methano-2H-cyclo-penta[b]furan-6-yl 4-chlorobutyrate The target compound was obtained by the same procedure as in Example 1-1-1 aside from using 6-hydroxy-2-oxo-4- oxahexahydro-3,5-methano-2H-cyclopenta[b]furan instead of methyl 6-hydroxy-2-oxohexahydro-3,5-methano-2H-cyclopenta-[b]furan-7-carboxylate. Yield 80%.

IR (thin film): ν=2956, 1789, 1737, 1448, 1363, 1322, 1230, 1195, 1186, 1153, 1141, 1120, 1049, 1029, 877 cm$^{-1}$ $^1$H-NMR (600 MHz in DMSO-d6):

δ=2.03-2.13 (3H, m), 2.21-2.28 (1H, m), 2.56 (2H, t), 2.74 (1H, m), 3.60 (2H, t), 4.64 (1H, d), 4.69 (1H, d) 4.73 (1H, s), 5.35 (1H, t) ppm Example 1-3-2

Synthesis of 2-oxo-4-oxahexahydro-3,5-methano-2H-cyclopenta[b]furan-6-yl 4-(methacryloyloxy) butyrate The target compound was obtained by the same procedure as in Example 1-1-2 aside from using 2-oxo-4-oxahexahydro-3,5-methano-2H-cyclopenta[b]furan-6-yl 4-chlorobutyrate instead of 7-methoxycarbonyl-2-oxohexahydro-3,5-methano-2H-cyclopenta[b]furan-6-yl 4-chlorobutyrate. Yield 81%.

IR (thin film): ν=2975, 2956, 1779, 1745, 1714, 1639, 1473, 1413, 1324, 1301, 1270, 1172, 1122, 1095, 1045, 1024, 987, 968 cm$^{-1}$ $^1$H-NMR (600 MHz in CDCl$_3$):

δ=1.92 (3H, m), 1.99-2.09 (3H, m), 2.24 (1H, m), 2.47 (2H, t), 2.73 (1H, m), 4.18 (2H, m), 4.63 (1H, m), 4.68 (1H, d), 4.73 (1H, d), 5.34 (1H, t), 5.56 (1H, m), 6.08 (1H, m) ppm Example 1-4

Synthesis of Monomer 4

The procedure of Examples 1-1-1 and 1-1-3 was repeated aside from using 6-hydroxy-2-oxo-4-oxahexahydro-3,5-methano-2H-cyclopenta[b]furan instead of methyl 6-hydroxy-2-oxohexahydro-3,5-methano-2H-cyclopenta[b]furan-7-carboxylate and acrylic acid instead of methacrylic acid. There was obtained 2-oxo-4-oxahexahydro-3,5-methano-2H-cyclopenta[b]furan-6-yl 4-(acryloyloxy)butyrate. Two-step yield 70%.

Example 1-5

Synthesis of Monomer 5

The procedure of Examples 1-1-1 and 1-1-3 was repeated aside from using 6-hydroxy-2-oxo-4-oxahexahydro-3,5-methano-2H-cyclopenta[b]furan instead of methyl 6-hydroxy-2-oxohexahydro-3,5-methano-2H-cyclopenta[b]furan-7-carboxylate and 2-(trifluoromethyl)acrylic acid instead of methacrylic acid. There was obtained 2-oxo-4-oxahexahydro-3,5-methano-2H-cyclo-penta[b]furan-6-yl 4-[2-(trifluoromethyl)acryloyloxy]-butyrate. Two-step yield 66%.

Example 1-6

Synthesis of Monomer 6

The procedure of Examples 1-1-1 and 1-1-2 was repeated aside from using methyl 6-hydroxy-2-oxo-4-oxahexahydro-3,5-methano-2H-cyclopenta[b]furan-7-carboxylate instead of methyl 6-hydroxy-2-oxohexahydro-3,5-methano-2H-cyclopenta[b]furan-7-carboxylate. There was obtained 7-methoxycarbonyl-2-oxo-4-oxahexahydro-3,5-methano-2H-cyclopenta[b]furan-6-yl 4-(methacryloyloxy)butyrate. Two-step yield 70%.

Example 1-7

Synthesis of Monomer 7

The procedure of Examples 1-1-1 and 1-1-3 was repeated aside from using methyl 6-hydroxy-2-oxo-4-oxahexahydro-3,5-methano-2H-cyclopenta[b]furan-7-carboxylate instead of methyl 6-hydroxy-2-oxohexahydro-3,5-methano-2H-cyclopenta[b]furan-7-carboxylate and acrylic acid instead of methacrylic acid. There was obtained 7-methoxycarbonyl-2-oxo-4-oxahexahydro-3,5-methano-2H-cyclopenta[b]furan-6-yl 4-(acryloyloxy)-butyrate. Two-step yield 65%.

Example 1-8

Synthesis of Monomer 8

Example 1-8-1

Synthesis of 7-tert-butoxycarbonyl-2-oxohexahydro-3,5-methano-2H-cyclopenta[b]furan-6-yl 4-chlorobutyrate The target compound was obtained by the same procedure as in Example 1-1-1 aside from using tert-butyl 6-hydroxy-2-oxohexahydro-3,5-methano-2H-cyclopenta[b]furan-7-carboxylate instead of methyl 6-hydroxy-2-oxohexahydro-3,5-methano-2H-cyclopenta[b]furan-7-carboxylate. Yield 82%.

IR (thin film): ν=3004, 2977, 2935, 1781, 1727, 1639, 1353, 1413, 1340, 1303, 1259, 1199, 1180, 1149, 1112, 1041, 1014 cm$^{-1}$ $^1$H-NMR (600 MHz in CDCl$_3$):

δ=1.41 (9H, s), 1.51 (1H, d), 1.81 (1H, d), 1.98 (2H, q), 2.47 (2H, t), 2.70 (1H, s), 2.85 (1H, d), 2.90 (1H, d), 3.22 (1H, dt-like), 3.66 (2H, d), 4.58 (1H, d), 4.59 (1H, s) ppm Example 1-8-2

Synthesis of 7-tert-butoxycarbonyl-2-oxohexahydro-3,5-methano-2H-cyclopenta[b]furan-6-yl 4-(methacryloyloxy)-butyrate The target compound was obtained by the same procedure as in Example 1-1-2 aside from using 7-tert-butoxycarbonyl-2-oxohexahydro-3,5-methano-2H-cyclopenta[b]furan-6-yl 4-chloro-butyrate instead of 7-methoxycarbonyl-2-oxohexahydro-3,5-methano-2H-cyclopenta[b]furan-6-yl 4-chlorobutyrate. Yield 82%.

IR (thin film): ν=2979, 2931, 1787, 1720, 1637, 1456, 1394, 1369, 1321, 1297, 1257, 1216, 1155, 1112, 1062, 1010 cm$^{-1}$ $^1$H-NMR (600 MHz in DMSO-d6): δ=1.41 (9H, s), 1.50 (1H, d), 1.81 (1H, d), 1.87 (3H, t), 1.89 (2H, q), 2.42 (2H, t), 2.68 (1H, s), 2.85 (1H, d), 2.90 (1H, s), 3.22 (1H, dt-like), 4.11 (2H, dt-like), 4.56 (1H, d), 4.58 (1H, d), 5.67 (1H, m), 6.01 (1H, s) ppm

Example 1-9

Synthesis of Monomer 9

The procedure of Examples 1-1-1 and 1-1-3 was repeated aside from using 1-ethyl-1-cyclopentyl 6-hydroxy-2-oxo-hexahydro-3,5-methano-2H-cyclopenta[b]furan-7-carboxylate instead of methyl 6-hydroxy-2-oxohexahydro-3,5-methano-2H-cyclopenta-[b]furan-7-carboxylate. There was obtained 7-(1-ethyl-1-cyclopentyloxycarbonyl)-2-oxo-hexahydro-3,5-methano-2H-cyclopenta[b]furan-6-yl 4-(methacryloyloxy)butyrate. Two-step yield 72%.

Example 1-10

Synthesis of Monomer 10

The procedure of Examples 1-1-1 and 1-1-2 was repeated aside from using 6-hydroxy-2-oxo-4-oxahexahydro-3,5-methano-2H-cyclopenta[b]furan instead of methyl 6-hydroxy-2-oxohexahydro-3,5-methano-2H-cyclopenta[b]furan-7-carboxylate and 5-chlorovaleric acid chloride instead of 4-chlorobutyric acid chloride. There was obtained 2-oxo-4-oxahexahydro-3,5-methano-2H-cyclopenta[b]furan-6-yl 5-(methacryloyloxy)-valerate. Two-step yield 62%.

Example 1-11

Synthesis of Monomer 11

The procedure of Examples 1-1-1 and 1-1-3 was repeated aside from using 6-hydroxy-2-oxo-4-oxahexahydro-3,5-methano-2H-cyclopenta[b]furan instead of methyl 6-hydroxy-2-oxohexahydro-3,5-methano-2H-cyclopenta[b]furan-7-carboxylate and 5-chlorovaleric acid chloride instead of 4-chlorobutyric acid chloride. There was obtained 2-oxo-4-oxahexahydro-3,5-methano-2H-cyclopenta[b]furan-6-yl 5-(acryloyloxy)valerate. Two-step eld 56%.

Monomer 1

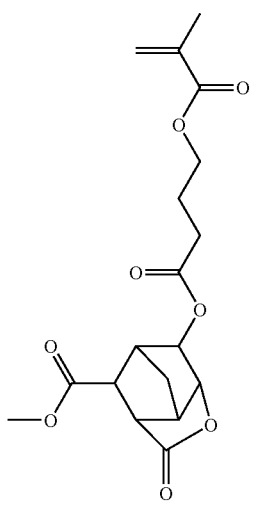

-continued

Monomer 2

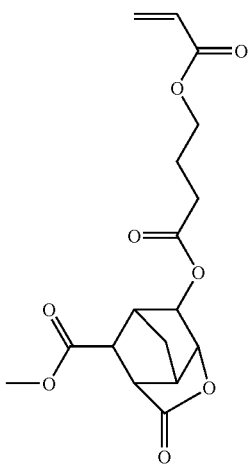

Monomer 3

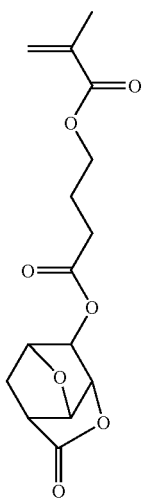

Monomer 4

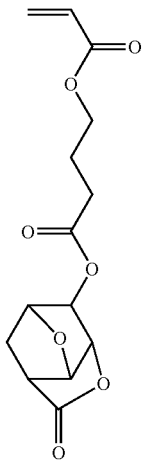

-continued
Monomer 5
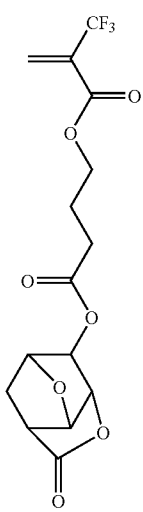
Monomer 6
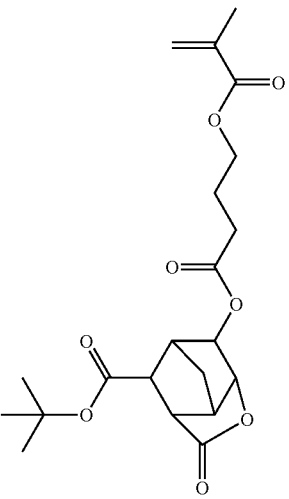
Monomer 7
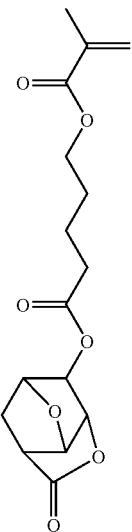
-continued
Monomer 8
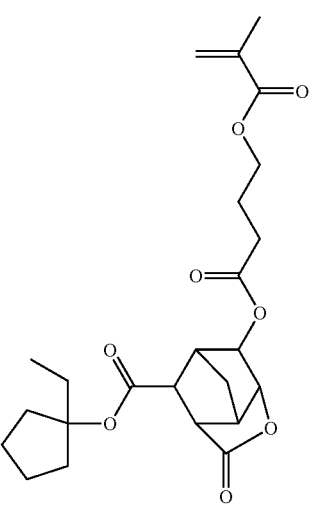
Monomer 9
Monomer 10

-continued

Monomer 11

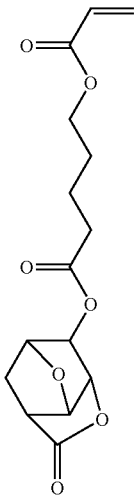

Example 2

Polymers within the scope of the invention were synthesized according to the following formulation.

Example 2-1

Synthesis of Polymer 1

In 70.0 g of methyl ethyl ketone were dissolved 22.9 g of Monomer 1, 17.1 g of 3-ethyl-3-exo-tetracyclo-[4.4.0.1$^{2,5}$.1$^{7,10}$]dodecanyl methacrylate, and 1.025 g of 2,2'-azobisisobutyronitrile. In a nitrogen atmosphere, this solution was added dropwise over 4 hours to 23.3 g of methyl ethyl ketone while stirring at 80° C. The solution was stirred at 80° C. for a further 2 hours. The reaction solution was cooled to room temperature, and with vigorous stirring, added dropwise to 640 g of methanol. The resulting solids were collected by filtration and dried in vacuum at 50° C. for 15 hours, obtaining a white powder solid designated Polymer 1. The amount was 33.6 g in a yield of 84%. Polymer 1 had the composition and Mw shown below.

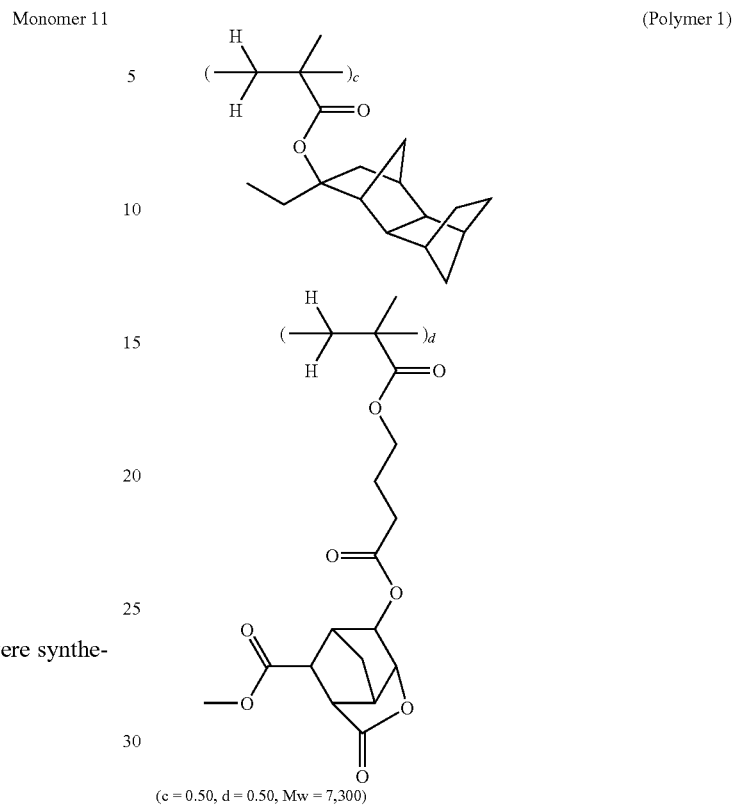

(c = 0.50, d = 0.50, Mw = 7,300)

Examples 2-2 to 2-36 and Comparative Examples 1-1 to 1-4

Synthesis of Polymers 2 to 40

Polymers 2 to 40 were synthesized by the same procedure as Example 2-1 except that the type and proportion of monomers were changed, with their compositional proportion (in molar ratio) and Mw being shown in Table 1. The structure of the units is shown in Tables 2 to 5.

TABLE 1

|  | Resin | Unit 1 (ratio) | Unit 2 (ratio) | Unit 3 (ratio) | Unit 4 (ratio) | Mw |
|---|---|---|---|---|---|---|
| Example 2-1 | Polymer 1 | L-1M (0.50) | A-1M (0.50) | — | — | 7,300 |
| Example 2-2 | Polymer 2 | L-2M (0.50) | A-1M (0.50) | — | — | 7,100 |
| Example 2-3 | Polymer 3 | L-3M (0.50) | A-1M (0.50) | — | — | 7,500 |
| Example 2-4 | Polymer 4 | L-4M (0.50) | A-1M (0.50) | — | — | 7,600 |
| Example 2-5 | Polymer 5 | L-1M (0.55) | A-1M (0.30) | B-1M (0.15) | — | 7,300 |
| Example 2-6 | Polymer 6 | L-1M (0.50) | A-2M (0.35) | B-1M (0.15) | — | 7,600 |
| Example 2-7 | Polymer 7 | L-1M (0.55) | A-3M (0.30) | B-1M (0.15) | — | 7,100 |
| Example 2-8 | Polymer 8 | L-1M (0.55) | A-4M (0.30) | B-1M (0.15) | — | 7,500 |
| Example 2-9 | Polymer 9 | L-1M (0.50) | A-5M (0.35) | B-1M (0.15) | — | 6,700 |
| Example 2-10 | Polymer 10 | L-1M (0.50) | A-6M (0.35) | B-1M (0.15) | — | 7,200 |
| Example 2-11 | Polymer 11 | L-2M (0.55) | A-1M (0.30) | B-1M (0.15) | — | 7,500 |
| Example 2-12 | Polymer 12 | L-2M (0.50) | A-2M (0.35) | B-1M (0.15) | — | 7,700 |
| Example 2-13 | Polymer 13 | L-2M (0.55) | A-3M (0.30) | B-1M (0.15) | — | 7,200 |
| Example 2-14 | Polymer 14 | L-2M (0.55) | A-4M (0.30) | B-1M (0.15) | — | 7,600 |

TABLE 1-continued

|  | Resin | Unit 1 (ratio) | Unit 2 (ratio) | Unit 3 (ratio) | Unit 4 (ratio) | Mw |
|---|---|---|---|---|---|---|
| Example 2-15 | Polymer 15 | L-2M (0.50) | A-5M (0.35) | B-1M (0.15) | — | 6,800 |
| Example 2-16 | Polymer 16 | L-2M (0.50) | A-6M (0.35) | B-1M (0.15) | — | 7,300 |
| Example 2-17 | Polymer 17 | L-1M (0.55) | A-1M (0.30) | B-2M (0.15) | — | 6,900 |
| Example 2-18 | Polymer 18 | L-1M (0.55) | A-1M (0.30) | B-1A (0.15) | — | 7,000 |
| Example 2-19 | Polymer 19 | L-1M (0.30) | A-1M (0.30) | B-1M (0.15) | B-3M (0.25) | 7,000 |
| Example 2-20 | Polymer 20 | L-1M (0.30) | A-1M (0.30) | B-1M (0.15) | B-4M (0.25) | 6,900 |
| Example 2-21 | Polymer 21 | L-1M (0.30) | A-1M (0.30) | B-1M (0.15) | B-5M (0.25) | 6,800 |
| Example 2-22 | Polymer 22 | L-1M (0.30) | A-1M (0.30) | B-1M (0.15) | B-6M (0.25) | 6,900 |
| Example 2-23 | Polymer 23 | L-1M (0.30) | A-2M (0.35) | B-1M (0.15) | B-6M (0.20) | 6,700 |
| Example 2-24 | Polymer 24 | L-1M (0.30) | A-3M (0.30) | B-1M (0.15) | B-6M (0.25) | 7,100 |
| Example 2-25 | Polymer 25 | L-1M (0.30) | A-4M (0.30) | B-1M (0.15) | B-6M (0.25) | 7,200 |
| Example 2-26 | Polymer 26 | L-1M (0.30) | A-5M (0.35) | B-1M (0.15) | B-6M (0.20) | 7,500 |
| Example 2-27 | Polymer 27 | L-1M (0.30) | A-6M (0.35) | B-1M (0.15) | B-6M (0.20) | 7,400 |
| Example 2-28 | Polymer 28 | L-1M (0.45) | A-1M (0.30) | B-1M (0.15) | C-1M (0.10) | 7,200 |
| Example 2-29 | Polymer 29 | L-1M (0.45) | A-1M (0.30) | B-1M (0.15) | C-2M (0.10) | 7,000 |
| Example 2-30 | Polymer 30 | L-1M (0.45) | A-1M (0.30) | B-1M (0.15) | C-3M (0.10) | 7,100 |
| Example 2-31 | Polymer 31 | L-1M (0.45) | A-1M (0.30) | B-1M (0.15) | C-4M (0.10) | 7,000 |
| Example 2-32 | Polymer 32 | L-1M (0.45) | A-1M (0.30) | B-1M (0.15) | C-5M (0.10) | 6,700 |
| Example 2-33 | Polymer 33 | L-2M (0.30) | A-1M (0.30) | B-1M (0.15) | B-6M (0.25) | 7,000 |
| Example 2-34 | Polymer 34 | L-2M (0.30) | A-3M (0.30) | B-1M (0.15) | B-6M (0.25) | 7,500 |
| Example 2-35 | Polymer 35 | L-1M (0.70) | A-2M (0.30) | — | — | 8,200 |
| Example 2-36 | Polymer 36 | L-2M (0.70) | A-2M (0.30) | — | — | 8,000 |
| Comparative Example 1-1 | Polymer 37 | — | A-1M (0.30) | B-1M (0.15) | B-5M (0.55) | 6,900 |
| Comparative Example 1-2 | Polymer 38 | — | A-1M (0.30) | B-1M (0.15) | B-7M (0.55) | 7,200 |
| Comparative Example 1-3 | Polymer 39 | — | A-2M (0.30) | B-7M (0.70) | — | 7,700 |
| Comparative Example 1-4 | Polymer 40 | — | A-2M (0.30) | B-8M (0.70) | — | 7,600 |

TABLE 2

| L-1M (R = CH$_3$) | L-2M (R = CH$_3$) | L-3M (R = CH$_3$) | L-4M (R = CH$_3$) |
|---|---|---|---|
| L-1A (R = H) | L-2A (R = H) | L-3A (R = H) | L-4A (R = H) |

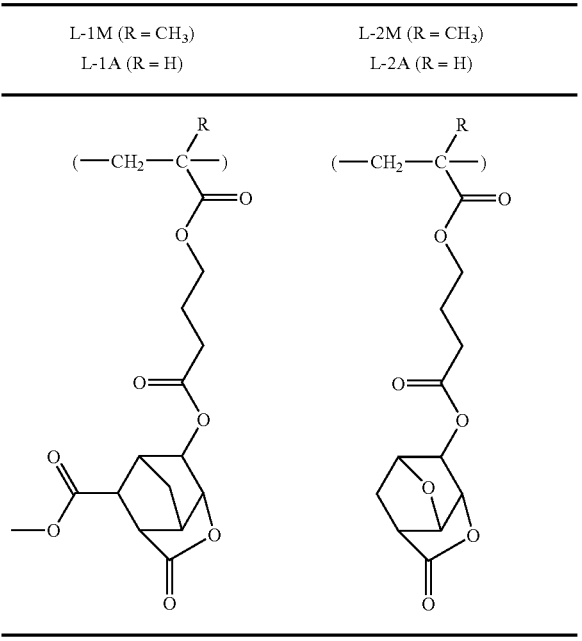
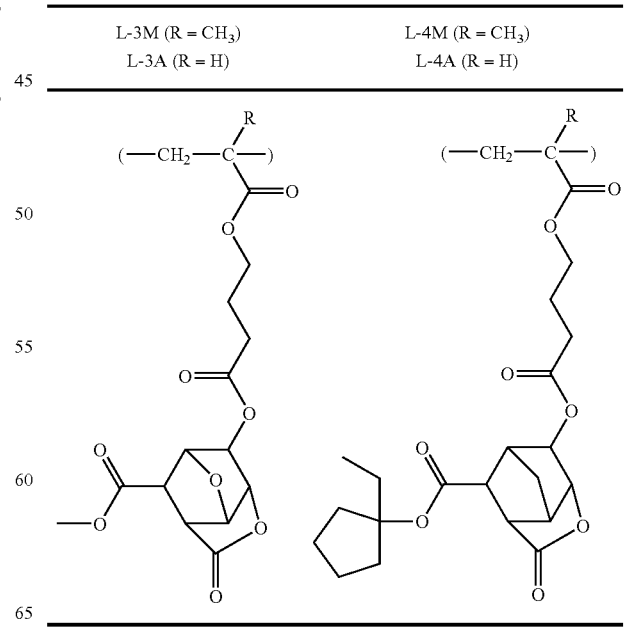

TABLE 3

| A-1M (R = CH₃) | A-2M (R = CH₃) |
| A-1A (R = H) | A-2A (R = H) |

| A-3M (R = CH₃) | A-4M (R = CH₃) |
| A-3A (R = H) | A-4A (R = H) |

| A-5M (R = CH₃) | A-6M (R = CH₃) |
| A-5A (R = H) | A-6A (R = H) |

TABLE 4

| B-1M (R = CH₃) | B-2M (R = CH₃) |
| B-1A (R = H) | B-2A (R = H) |

TABLE 4-continued

| B-3M (R = CH₃) | B-4M (R = CH₃) |
| B-3A (R = H) | B-4A (R = H) |

| B-5M (R = CH₃) | B-6M (R = CH₃) |
| B-5A (R = H) | B-6A (R = H) |

| B-7M (R = CH₃) | B-8M (R = CH₃) |
| B-7A (R = H) | B-8A (R = H) |

TABLE 5

| C-1M (R = CH₃)  C-1A (R = H) | C-2M (R = CH₃)  C-2A (R = H) |
|---|---|
| $$\begin{array}{c} R \\ (-CH_2-C-) \\ | \\ C=O \\ | \\ HO \end{array}$$ | (—CH₂—C(R)—) with ester linkage to tetrahydrofuran ring bearing CF₂ and C(CF₃)(OH) |

| C-3M (R = CH₃)  C-3A (R = H) | C-4M (R = CH₃)  C-4A (R = H) |
|---|---|
| (—CH₂—C(R)—)C(=O)O–cyclohexyl substituted with C(CF₃)₂OH groups | (—CH₂—C(R)—)C(=O)O–C(CH₃)(CF₃)–C(CF₃)(OH) |

TABLE 5-continued

| C-5M (R = CH₃)  C-5A (R = H) |
|---|
| (—CH₂—C(R)—)C(=O)O–CH₂–C(CF₃)(CF₃)–OH |

Preparation of Resist Compositions

Examples 3-1 to 3-58 & Comparative Examples 2-1 to 2-2

Resist compositions were prepared by using inventive resins (Polymer 1 to 34, abbreviated P01 to P34) or comparative resins (Polymers 37 to 38, abbreviated P37 to P38) as the base resin, and dissolving the polymer, an acid generator (PAG), and a quencher (Base) in a solvent mixture (PGMEA and CyHO) containing 0.01 wt % of surfactant KH-20 (Asahi Glass Co., Ltd.) in accordance with the recipe shown in Tables 6 and 7. These compositions were each filtered through a Teflon® filter having a pore diameter 0.2 μm, thereby giving inventive resist solutions (R-01 to 58) and comparative resist solutions (R-59 to 60).

TABLE 6

|  | Resist | Resin (pbw) | PAG (pbw) | Base (pbw) | Solvent 1 (pbw) | Solvent 2 (pbw) |
|---|---|---|---|---|---|---|
| Example 3-1 | R-01 | P-01 (80) | PAG-1 (4.4) | Base-1 (0.94) | PGMEA (560) | CyHO (240) |
| Example 3-2 | R-02 | P-02 (80) | PAG-1 (4.4) | Base-1 (0.94) | PGMEA (560) | CyHO (240) |
| Example 3-3 | R-03 | P-03 (80) | PAG-1 (4.4) | Base-1 (0.94) | PGMEA (560) | CyHO (240) |
| Example 3-4 | R-04 | P-04 (80) | PAG-1 (4.4) | Base-1 (0.94) | PGMEA (560) | CyHO (240) |
| Example 3-5 | R-05 | P-05 (80) | PAG-1 (4.4) | Base-1 (0.94) | PGMEA (560) | CyHO (240) |
| Example 3-6 | R-06 | P-06 (80) | PAG-1 (4.4) | Base-1 (0.94) | PGMEA (560) | CyHO (240) |
| Example 3-7 | R-07 | P-07 (80) | PAG-1 (4.4) | Base-1 (0.94) | PGMEA (560) | CyHO (240) |
| Example 3-8 | R-08 | P-08 (80) | PAG-1 (4.4) | Base-1 (0.94) | PGMEA (560) | CyHO (240) |
| Example 3-9 | R-09 | P-09 (80) | PAG-1 (4.4) | Base-1 (0.94) | PGMEA (560) | CyHO (240) |
| Example 3-10 | R-10 | P-10 (80) | PAG-1 (4.4) | Base-1 (0.94) | PGMEA (560) | CyHO (240) |
| Example 3-11 | R-11 | P-11 (80) | PAG-1 (4.4) | Base-1 (0.94) | PGMEA (560) | CyHO (240) |
| Example 3-12 | R-12 | P-12 (80) | PAG-1 (4.4) | Base-1 (0.94) | PGMEA (560) | CyHO (240) |
| Example 3-13 | R-13 | P-13 (80) | PAG-1 (4.4) | Base-1 (0.94) | PGMEA (560) | CyHO (240) |
| Example 3-14 | R-14 | P-14 (80) | PAG-1 (4.4) | Base-1 (0.94) | PGMEA (560) | CyHO (240) |
| Example 3-15 | R-15 | P-15 (80) | PAG-1 (4.4) | Base-1 (0.94) | PGMEA (560) | CyHO (240) |
| Example 3-16 | R-16 | P-16 (80) | PAG-1 (4.4) | Base-1 (0.94) | PGMEA (560) | CyHO (240) |
| Example 3-17 | R-17 | P-17 (80) | PAG-1 (4.4) | Base-1 (0.94) | PGMEA (560) | CyHO (240) |
| Example 3-18 | R-18 | P-18 (80) | PAG-1 (4.4) | Base-1 (0.94) | PGMEA (560) | CyHO (240) |
| Example 3-19 | R-19 | P-19 (80) | PAG-1 (4.4) | Base-1 (0.94) | PGMEA (560) | CyHO (240) |
| Example 3-20 | R-20 | P-20 (80) | PAG-1 (4.4) | Base-1 (0.94) | PGMEA (560) | CyHO (240) |
| Example 3-21 | R-21 | P-21 (80) | PAG-1 (4.4) | Base-1 (0.94) | PGMEA (560) | CyHO (240) |
| Example 3-22 | R-22 | P-22 (80) | PAG-1 (4.4) | Base-1 (0.94) | PGMEA (560) | CyHO (240) |
| Example 3-23 | R-23 | P-23 (80) | PAG-1 (4.4) | Base-1 (0.94) | PGMEA (560) | CyHO (240) |
| Example 3-24 | R-24 | P-24 (80) | PAG-1 (4.4) | Base-1 (0.94) | PGMEA (560) | CyHO (240) |
| Example 3-25 | R-25 | P-25 (80) | PAG-1 (4.4) | Base-1 (0.94) | PGMEA (560) | CyHO (240) |
| Example 3-26 | R-26 | P-26 (80) | PAG-1 (4.4) | Base-1 (0.94) | PGMEA (560) | CyHO (240) |
| Example 3-27 | R-27 | P-27 (80) | PAG-1 (4.4) | Base-1 (0.94) | PGMEA (560) | CyHO (240) |
| Example 3-28 | R-28 | P-28 (80) | PAG-1 (4.4) | Base-1 (0.94) | PGMEA (560) | CyHO (240) |
| Example 3-29 | R-29 | P-29 (80) | PAG-1 (4.4) | Base-1 (0.94) | PGMEA (560) | CyHO (240) |
| Example 3-30 | R-30 | P-30 (80) | PAG-1 (4.4) | Base-1 (0.94) | PGMEA (560) | CyHO (240) |
| Example 3-31 | R-31 | P-31 (80) | PAG-1 (4.4) | Base-1 (0.94) | PGMEA (560) | CyHO (240) |
| Example 3-32 | R-32 | P-32 (80) | PAG-1 (4.4) | Base-1 (0.94) | PGMEA (560) | CyHO (240) |
| Example 3-33 | R-33 | P-33 (80) | PAG-1 (4.4) | Base-1 (0.94) | PGMEA (560) | CyHO (240) |
| Example 3-34 | R-34 | P-34 (80) | PAG-1 (4.4) | Base-1 (0.94) | PGMEA (560) | CyHO (240) |
| Example 3-35 | R-35 | P-05 (80) | PAG-2 (4.9) | Base-1 (0.94) | PGMEA (560) | CyHO (240) |

TABLE 6-continued

|  | Resist | Resin (pbw) | PAG (pbw) | Base (pbw) | Solvent 1 (pbw) | Solvent 2 (pbw) |
|---|---|---|---|---|---|---|
| Example 3-36 | R-36 | P-11 (80) | PAG-2 (4.9) | Base-1 (0.94) | PGMEA (560) | CyHO (240) |
| Example 3-37 | R-37 | P-22 (80) | PAG-2 (4.9) | Base-1 (0.94) | PGMEA (560) | CyHO (240) |
| Example 3-38 | R-38 | P-24 (80) | PAG-2 (4.9) | Base-1 (0.94) | PGMEA (560) | CyHO (240) |
| Example 3-39 | R-39 | P-33 (80) | PAG-2 (4.9) | Base-1 (0.94) | PGMEA (560) | CyHO (240) |
| Example 3-40 | R-40 | P-34 (80) | PAG-2 (4.9) | Base-1 (0.94) | PGMEA (560) | CyHO (240) |

TABLE 7

|  | Resist | Resin (pbw) | PAG (pbw) | Base (pbw) | Solvent 1 (pbw) | Solvent 2 (pbw) |
|---|---|---|---|---|---|---|
| Example 3-41 | R-41 | P-05 (80) | PAG-3 (4.7) | Base-1 (0.94) | PGMEA (560) | CyHO (240) |
| Example 3-42 | R-42 | P-11 (80) | PAG-3 (4.7) | Base-1 (0.94) | PGMEA (560) | CyHO (240) |
| Example 3-43 | R-43 | P-22 (80) | PAG-3 (4.7) | Base-1 (0.94) | PGMEA (560) | CyHO (240) |
| Example 3-44 | R-44 | P-24 (80) | PAG-3 (4.7) | Base-1 (0.94) | PGMEA (560) | CyHO (240) |
| Example 3-45 | R-45 | P-33 (80) | PAG-3 (4.7) | Base-1 (0.94) | PGMEA (560) | CyHO (240) |
| Example 3-46 | R-46 | P-34 (80) | PAG-3 (4.7) | Base-1 (0.94) | PGMEA (560) | CyHO (240) |
| Example 3-47 | R-47 | P-05 (80) | PAG-1 (2.2) PAG-3 (2.3) | Base-1 (0.94) | PGMEA (560) | CyHO (240) |
| Example 3-48 | R-48 | P-11 (80) | PAG-1 (2.2) PAG-3 (2.3) | Base-1 (0.94) | PGMEA (560) | CyHO (240) |
| Example 3-49 | R-49 | P-22 (80) | PAG-1 (2.2) PAG-3 (2.3) | Base-1 (0.94) | PGMEA (560) | CyHO (240) |
| Example 3-50 | R-50 | P-24 (80) | PAG-1 (2.2) PAG-3 (2.3) | Base-1 (0.94) | PGMEA (560) | CyHO (240) |
| Example 3-51 | R-51 | P-33 (80) | PAG-1 (2.2) PAG-3 (2.3) | Base-1 (0.94) | PGMEA (560) | CyHO (240) |
| Example 3-52 | R-52 | P-34 (80) | PAG-1 (2.2) PAG-3 (2.3) | Base-1 (0.94) | PGMEA (560) | CyHO (240) |
| Example 3-53 | R-53 | P-05 (80) | PAG-1 (4.4) | Base-2 (0.74) | PGMEA (560) | CyHO (240) |
| Example 3-54 | R-54 | P-11 (80) | PAG-1 (4.4) | Base-2 (0.74) | PGMEA (560) | CyHO (240) |
| Example 3-55 | R-55 | P-22 (80) | PAG-1 (4.4) | Base-2 (0.74) | PGMEA (560) | CyHO (240) |
| Example 3-56 | R-56 | P-24 (80) | PAG-1 (4.4) | Base-2 (0.74) | PGMEA (560) | CyHO (240) |
| Example 3-57 | R-57 | P-33 (80) | PAG-1 (4.4) | Base-2 (0.74) | PGMEA (560) | CyHO (240) |
| Example 3-58 | R-58 | P-34 (80) | PAG-1 (4.4) | Base-2 (0.74) | PGMEA (560) | CyHO (240) |
| Comparative Example 2-1 | R-59 | P-35 (80) | PAG-1 (4.4) | Base-1 (0.94) | PGMEA (560) | CyHO (240) |
| Comparative Example 2-2 | R-60 | P-36 (80) | PAG-1 (4.4) | Base-1 (0.94) | PGMEA (560) | CyHO (240) |

The acid generator, quencher (base) and solvent shown in Tables 6 and 7 have the following meanings.

PAG-1: triphenylsulfonium nonafluorobutanesulfonate
PAG-2: 4-t-butoxyphenyldiphenylsulfonium nonafluorobutane-sulfonate
PAG-3: triphenylsulfonium 1,1,3,3,3-pentafluoro-2-cyclo-hexylcarboxypropanesulfonate
Base-1: tri(2-methoxymethoxyethyl)amine
Base-2: 2-(2-methoxyethoxymethoxy)ethylmorpholine
PGMEA: 1-methoxyisopropyl acetate
CyHO: cyclohexanone Evaluation of Resolution and Line Edge Roughness Examples 4-1 to 4-58 & Comparative Examples 3-1 to 3-2

Each of inventive resist compositions (R-01 to 58) and comparative resist compositions (R-59 to 60) was spin coated on a silicon wafer having an antireflective coating (ARC-29A, Nissan Chemical Co., Ltd.) of 78 nm thick and baked at 110° C. for 60 seconds, forming a resist film of 170 nm thick. The wafer was exposed by means of an ArF excimer laser stepper (Nikon Corp., NA 0.85), post-exposure baked (PEB) for 60 seconds, and puddle developed with a 2.38 wt % tetramethylammonium hydroxide aqueous solution for 30 seconds, forming a 1:1 line-and-space pattern and a 1:10 isolated line pattern. During the PEB, an optimum temperature for each resist composition was employed.

The patterned wafer was observed under a top-down scanning electron microscope (TDSEM). The optimum exposure (Eop) was defined as the exposure dose (mJ/cm$^2$) which provided a 1:1 resolution at the top and bottom of a 90-nm 1:1 line-and-space pattern. The maximum resolution of the resist was defined as the minimum line width (on-mask size, in increments of 5 nm) of a 1:1 line-and-space pattern that was resolved and separated at the optimum exposure, with smaller values indicating better resolution. The 1:10 isolated line pattern at the optimum exposure was also observed for determining an actual on-wafer size of the isolated line pattern with an on-mask size of 140 nm, which was reported as mask fidelity (on-wafer size, a larger size being better). Further, a line portion of the 90-nm 1:1 line-and-space pattern was examined for line edge roughness (LER). For each of left and right edges of a line, measurement was made at 16 points along a measurement region of 300 nm long. Provided that L and R represent averages of deviations of measurement points from the center line along the left and right edges, respectively, a square root of $(L^2+R^2)$ is reported as LER (in nm, smaller deviation being better).

Table 8 tabulates the test results (maximum resolution, mask fidelity and LER) of the inventive and comparative resist compositions.

TABLE 8

|  | Resist | PEB temp. (°C.) | Eop (mJ/cm$^2$) | Maximum resolution (nm) | Mask fidelity (nm) | LER (nm) |
|---|---|---|---|---|---|---|
| Example 4-1 | R-01 | 95 | 39.0 | 75 | 85 | 5.2 |
| Example 4-2 | R-02 | 95 | 41.0 | 75 | 88 | 5.5 |
| Example 4-3 | R-03 | 95 | 37.0 | 75 | 84 | 5.1 |
| Example 4-4 | R-04 | 95 | 34.0 | 80 | 83 | 4.9 |
| Example 4-5 | R-05 | 105 | 38.0 | 70 | 84 | 4.8 |
| Example 4-6 | R-06 | 120 | 40.0 | 75 | 85 | 5.3 |
| Example 4-7 | R-07 | 105 | 40.0 | 70 | 85 | 5.0 |
| Example 4-8 | R-08 | 120 | 39.0 | 75 | 83 | 5.2 |
| Example 4-9 | R-09 | 105 | 41.0 | 70 | 80 | 4.8 |
| Example 4-10 | R-10 | 105 | 41.0 | 70 | 86 | 4.7 |
| Example 4-11 | R-11 | 105 | 40.0 | 70 | 87 | 5.0 |
| Example 4-12 | R-12 | 120 | 43.0 | 70 | 87 | 5.4 |
| Example 4-13 | R-13 | 105 | 42.0 | 70 | 89 | 5.2 |
| Example 4-14 | R-14 | 120 | 41.0 | 70 | 86 | 5.3 |
| Example 4-15 | R-15 | 105 | 43.0 | 70 | 84 | 5.0 |
| Example 4-16 | R-16 | 105 | 43.0 | 70 | 90 | 4.8 |
| Example 4-17 | R-17 | 105 | 39.0 | 70 | 86 | 5.0 |
| Example 4-18 | R-18 | 100 | 40.0 | 75 | 80 | 4.9 |
| Example 4-19 | R-19 | 105 | 42.0 | 70 | 92 | 5.0 |
| Example 4-20 | R-20 | 105 | 39.0 | 70 | 89 | 5.0 |
| Example 4-21 | R-21 | 100 | 40.0 | 70 | 90 | 4.8 |
| Example 4-22 | R-22 | 100 | 38.0 | 70 | 86 | 4.6 |
| Example 4-23 | R-23 | 115 | 39.0 | 70 | 87 | 5.2 |
| Example 4-24 | R-24 | 100 | 41.0 | 70 | 89 | 4.9 |
| Example 4-25 | R-25 | 115 | 40.0 | 70 | 85 | 5.0 |
| Example 4-26 | R-26 | 100 | 41.0 | 70 | 84 | 4.6 |
| Example 4-27 | R-27 | 105 | 41.0 | 70 | 89 | 4.5 |
| Example 4-28 | R-28 | 105 | 43.0 | 70 | 86 | 5.2 |
| Example 4-29 | R-29 | 105 | 38.0 | 70 | 84 | 4.9 |
| Example 4-30 | R-30 | 105 | 39.0 | 70 | 85 | 5.0 |
| Example 4-31 | R-31 | 105 | 38.0 | 70 | 84 | 4.8 |
| Example 4-32 | R-32 | 100 | 39.0 | 70 | 85 | 4.8 |
| Example 4-33 | R-33 | 100 | 41.0 | 70 | 89 | 4.8 |
| Example 4-34 | R-34 | 105 | 44.0 | 70 | 92 | 5.0 |
| Example 4-35 | R-35 | 105 | 43.0 | 70 | 86 | 4.9 |
| Example 4-36 | R-36 | 105 | 44.0 | 70 | 88 | 5.0 |
| Example 4-37 | R-37 | 105 | 42.0 | 70 | 88 | 4.7 |
| Example 4-38 | R-38 | 105 | 45.0 | 70 | 92 | 5.0 |
| Example 4-39 | R-39 | 105 | 45.0 | 70 | 92 | 4.9 |
| Example 4-40 | R-40 | 105 | 48.0 | 70 | 94 | 5.0 |
| Example 4-41 | R-41 | 105 | 40.0 | 70 | 88 | 4.8 |
| Example 4-42 | R-42 | 105 | 42.0 | 70 | 90 | 4.9 |
| Example 4-43 | R-43 | 105 | 39.0 | 70 | 90 | 4.6 |
| Example 4-44 | R-44 | 105 | 43.0 | 70 | 92 | 4.8 |
| Example 4-45 | R-45 | 105 | 43.0 | 70 | 93 | 4.8 |
| Example 4-46 | R-46 | 105 | 46.0 | 70 | 96 | 4.9 |
| Example 4-47 | R-47 | 105 | 39.0 | 70 | 86 | 4.8 |
| Example 4-48 | R-48 | 100 | 40.0 | 70 | 89 | 5.0 |
| Example 4-49 | R-49 | 100 | 38.0 | 70 | 88 | 4.7 |
| Example 4-50 | R-50 | 100 | 42.0 | 70 | 91 | 5.0 |
| Example 4-51 | R-51 | 100 | 41.0 | 70 | 92 | 4.9 |
| Example 4-52 | R-52 | 105 | 45.0 | 70 | 94 | 5.0 |
| Example 4-53 | R-53 | 105 | 38.0 | 70 | 85 | 4.6 |
| Example 4-54 | R-54 | 100 | 39.0 | 70 | 88 | 4.8 |
| Example 4-55 | R-55 | 100 | 37.0 | 70 | 88 | 4.4 |
| Example 4-56 | R-56 | 100 | 40.0 | 70 | 90 | 4.6 |
| Example 4-57 | R-57 | 100 | 40.0 | 70 | 90 | 4.6 |
| Example 4-58 | R-58 | 100 | 42.0 | 70 | 90 | 4.5 |
| Comparative Example 3-1 | R-59 | 110 | 36.0 | 80 | 78 | 7.4 |
| Comparative Example 3-2 | R-60 | 105 | 43.0 | 75 | 79 | 5.8 |

It is seen from the results of Table 8 that the resist compositions within the scope of the invention have improved resolution and minimized LER when processed by ArF excimer laser lithography. The data of Comparative Examples in Table 8 reveal that prior art resist compositions satisfy either one or none of resolution and LER. It has been demonstrated that resist compositions comprising polymers comprising recurring units derived from the lactone-containing compounds of the invention are improved in resist properties over the prior art resist compositions.

Solubility of Polymers in Solvent

Examples 5-1, 5-2 and Comparative Examples 4-1, 4-2

A 1.0 g sample of the inventive resins (P-35 and P-36) or comparative resins (P-39 and P-40) was weighed and added to 5.0 g of 1-methoxyisopropyl acetate. The mixture was stirred at room temperature for one hour. It was visually inspected for solubility, with the results shown in Table 9.

TABLE 9

|  | Resin | Solvent solubility |
|---|---|---|
| Example 5-1 | P-35 | Fully dissolved |
| Example 5-2 | P-36 | Fully dissolved |
| Comparative Example 4-1 | P-39 | White turbid |
| Comparative Example 4-2 | P-40 | Slightly turbid |

The data of Table 9 demonstrate that the polymers within the scope of the invention are fully soluble in organic solvents.

Japanese Patent Application No. 2008-064337 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A lactone-containing compound having the general formula (1):

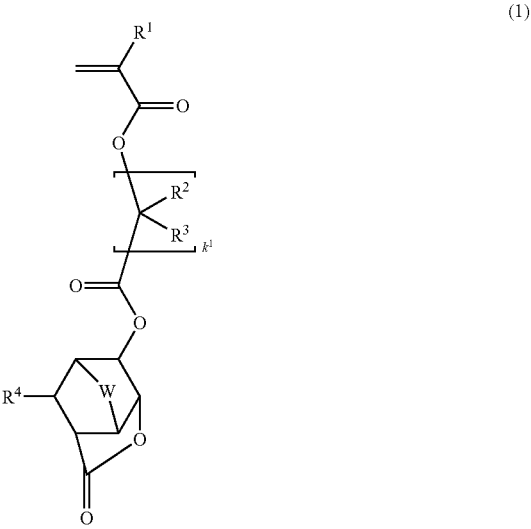

wherein $R^1$ is hydrogen, fluorine, methyl or trifluoromethyl, $R^2$ and $R^3$ are each independently hydrogen or a straight, branched or cyclic monovalent hydrocarbon group of 1 to 10 carbon atoms, or $R^2$ and $R^3$ may bond together to form an aliphatic hydrocarbon ring with the carbon atom to which they are attached, $R^4$ is hydrogen or $CO_2R^5$, $R^5$ is a straight, branched or cyclic monovalent hydrocarbon group of 1 to 15 carbon atoms which may have a halogen or oxygen atom, W is $CH_2$, O or S, with the proviso that $R^4$ is $CO_2R^5$ when W is $CH_2$, and $R^4$ is hydrogen or $CO_2R^5$ when W is O or S, and $k^1$ is an integer of 3 to 5.

2. A polymer comprising recurring units derived from the lactone-containing compound of claim 1.

3. A polymer comprising recurring units having the general formula (2):

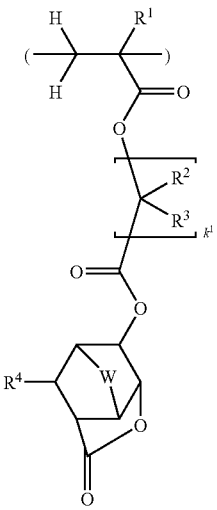

(2)

wherein $R^1$ is hydrogen, fluorine, methyl or trifluoromethyl, $R^2$ and $R^3$ are each independently hydrogen or a straight, branched or cyclic monovalent hydrocarbon group of 1 to 10 carbon atoms, or $R^2$ and $R^3$ may bond together to form an aliphatic hydrocarbon ring with the carbon atom to which they are attached, $R^4$ is hydrogen or $CO_2R^5$, $R^5$ is a straight, branched or cyclic monovalent hydrocarbon group of 1 to 15 carbon atoms which may have a halogen or oxygen atom, W is $CH_2$, O or S, with the proviso that $R^4$ is $CO_2R^5$ when W is $CH_2$, and $R^4$ is hydrogen or $CO_2R^5$ when W is O or S, and $k^1$ is an integer of 3 to 5.

4. The polymer of claim 2, further comprising recurring units having at least one of the general formulas (3) to (6):

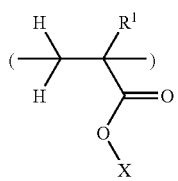

(3)

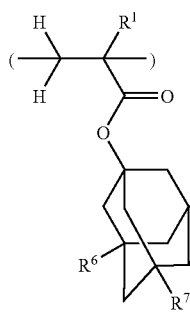

(4)

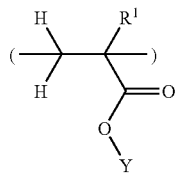

(5)

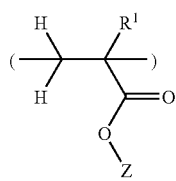

(6)

wherein $R^1$ is as defined above, $R^6$ and $R^7$ are each independently hydrogen or hydroxyl, X is an acid labile group, Y is a substituent group having a lactone structure different from formula (1), and Z is hydrogen, a fluoroalkyl group of 1 to 15 carbon atoms or a fluoroalcohol-containing substituent group of 1 to 15 carbon atoms.

5. A resist composition comprising the polymer of claim 2 as a base resin.

6. A process for forming a pattern comprising the steps of applying the resist composition of claim 5 onto a substrate to form a resist coating, heat treating the resist coating, exposing the resist coating to high-energy radiation or electron beam through a photomask, optionally heat treating the exposed coating, and developing it with a developer.

7. A process for forming a pattern comprising the steps of applying the resist composition of claim 5 onto a substrate to form a resist coating, heat treating the resist coating, exposing the resist coating to high-energy radiation or electron beam through a photomask, heat treating the exposed coating, and developing it with a developer, said exposing step being performed by immersion lithography including holding a liquid having a refractive index of at least 1.0 between the resist coating and a projection lens.

8. A process for forming a pattern comprising the steps of applying the resist composition of claim 5 onto a substrate to form a resist coating, heat treating the resist coating, forming a protective film on the resist coating, exposing the resist coating to high-energy radiation or electron beam through a photomask, heat treating the exposed coating, and developing it with a developer, said exposing step being performed by immersion lithography including holding a liquid having a refractive index of at least 1.0 between the protective film and a projection lens.

* * * * *